US012653357B2

(12) United States Patent
Kolekar et al.

(10) Patent No.: US 12,653,357 B2
(45) Date of Patent: Jun. 16, 2026

(54) TOILET SEAT ASSEMBLY WITH UV LIGHT

(71) Applicant: AS America, Inc., Piscataway, NJ (US)

(72) Inventors: Nitin S. Kolekar, Piscataway, NJ (US);
Christophe Bucher, Hillsborough, NJ
(US); Ki Bok Song, Plainview, NY
(US); Ronald D. Barndt, Bethlehem,
PA (US); Behnam Heydari,
Ridgewood, NJ (US); **Douglas Fornell
Leavitt, Bethlehem, PA (US); Zachary
Robert Sweitzer**, Green Pond, NJ (US)

(73) Assignee: AS America, Inc., Piscataway, NJ (US)

( * ) Notice: Subject to any disclaimer, the term of this
patent is extended or adjusted under 35
U.S.C. 154(b) by 166 days.

(21) Appl. No.: 18/286,478

(22) PCT Filed: Apr. 20, 2022

(86) PCT No.: PCT/US2022/025633
§ 371 (c)(1),
(2) Date: Oct. 11, 2023

(87) PCT Pub. No.: WO2022/226115
PCT Pub. Date: Nov. 27, 2022

(65) Prior Publication Data
US 2024/0197123 A1 Jun. 20, 2024

Related U.S. Application Data

(60) Provisional application No. 63/304,215, filed on Jan.
28, 2022, provisional application No. 63/177,631,
filed on Apr. 21, 2021.

(51) Int. Cl.
*A47K 13/30* (2006.01)
*A47K 13/10* (2006.01)
(Continued)

(52) U.S. Cl.
CPC ............ *A47K 13/302* (2013.01); *A47K 13/10*
(2013.01); *A47K 13/14* (2013.01); *A47K*
*13/307* (2013.01);
(Continued)

(58) Field of Classification Search
CPC ...... A47K 13/12; A47K 13/307; A47K 13/24;
A47K 13/302
See application file for complete search history.

(56) References Cited

U.S. PATENT DOCUMENTS 3,689,944 A 9/1972 Clayton
4,819,276 A * 4/1989 Stevens .................. A47K 13/12
4/236
(Continued)

FOREIGN PATENT DOCUMENTS

JP 2005-137822 A 6/2005
KR 10-1796266 B1 11/2017
(Continued)

OTHER PUBLICATIONS

Grover et al., U.S. Office Action dated Jul. 8, 2025, directed to U.S.
Appl. No. 18/286,477; 13 pages.

*Primary Examiner* — Christine J Skubinna
(74) *Attorney, Agent, or Firm* — Morrison & Foerster
LLP

(57) ABSTRACT

A toilet seat assembly includes a toilet seat and a lid hinged
to the toilet seat; wherein the lid comprises an inner liner that
comprises a shaped surface portion and a core portion, the
shaped surface portion is shaped to correspond to the
contoured upper seat surface of the toilet seat, and the core
portion is joined to the shaped surface portion, and in the
closed lid position the shaped surface portion of the lid
covers the upper seat surface of the toilet seat, and the core
portion of the lid covers the central opening of the toilet seat;
a plurality of UV-C lamps positioned in one or more
(Continued)

recessed portions of the shaped surface portion of the inner liner of the lid and configured to direct UV-C light towards the seat surface when the lid is in the closed lid position.

18 Claims, 41 Drawing Sheets

(51) Int. Cl.

| | | |
|---|---|---|
| *A47K 13/14* | (2006.01) | |
| *A61L 2/10* | (2026.01) | |
| *A61L 2/24* | (2006.01) | |
| *E03D 5/04* | (2006.01) | |
| *E03D 9/00* | (2006.01) | |

(52) U.S. Cl.
    CPC ................... *A61L 2/10* (2013.01); *A61L 2/24* (2013.01); *A61L 2202/11* (2013.01); *A61L 2202/14* (2013.01); *E03D 5/04* (2013.01); *E03D 9/002* (2013.01)

(56) References Cited

U.S. PATENT DOCUMENTS

| | | | |
|---|---|---|---|
| 4,873,729 | A | 10/1989 | Micallef |
| 6,189,159 | B1 | 2/2001 | Bailey et al. |

| | | | |
|---|---|---|---|
| 2003/0172448 | A1 | 9/2003 | Courtney |
| 2005/0283887 | A1 | 12/2005 | Park |
| 2006/0162301 | A1 | 7/2006 | Safuto |
| 2006/0206997 | A1 | 9/2006 | Chiang et al. |
| 2007/0017012 | A1 | 1/2007 | Greenspon |
| 2014/0115764 | A1* | 5/2014 | Cheng ................... A47K 13/302<br>4/222 |
| 2017/0290474 | A1 | 10/2017 | Kim |
| 2018/0325336 | A1* | 11/2018 | Chang ................... A47K 13/302 |
| 2020/0015642 | A1 | 1/2020 | Yu |
| 2020/0375416 | A1* | 12/2020 | Hand ...................... A47K 13/02 |
| 2020/0375417 | A1 | 12/2020 | Thorne |
| 2021/0353116 | A1 | 11/2021 | Dorra |
| 2022/0110492 | A1 | 4/2022 | Nakamura et al. |
| 2022/0125969 | A1* | 4/2022 | Gaska ........................ A61L 2/26 |
| 2022/0408988 | A1 | 12/2022 | Baines |
| 2024/0188770 | A1 | 6/2024 | Grover |
| 2025/0215679 | A1* | 7/2025 | Garrels ..................... A61L 9/20 |

FOREIGN PATENT DOCUMENTS

| | | | |
|---|---|---|---|
| TW | 201306778 | A1 | 2/2013 |
| WO | 2016/091055 | A1 | 6/2016 |
| WO | 2021/029736 | A1 | 2/2021 |

* cited by examiner

400

426

422

425     424

395

390

426

420

422

421          424          410

411

425

413

780

800

802

804

50cm

806

① Microwave Sensor on @standby

① Auto Open Lid When Detect Movement Signal in Sensing Area

② Sitting IR Sensor On

Original

① No Sitting, Just Standing

② IR Sensor Keep Detecting

New

① Auto Open Lid When Detect User Coming From Far to Near

② Sitting IR Sensor On

Figure 13:
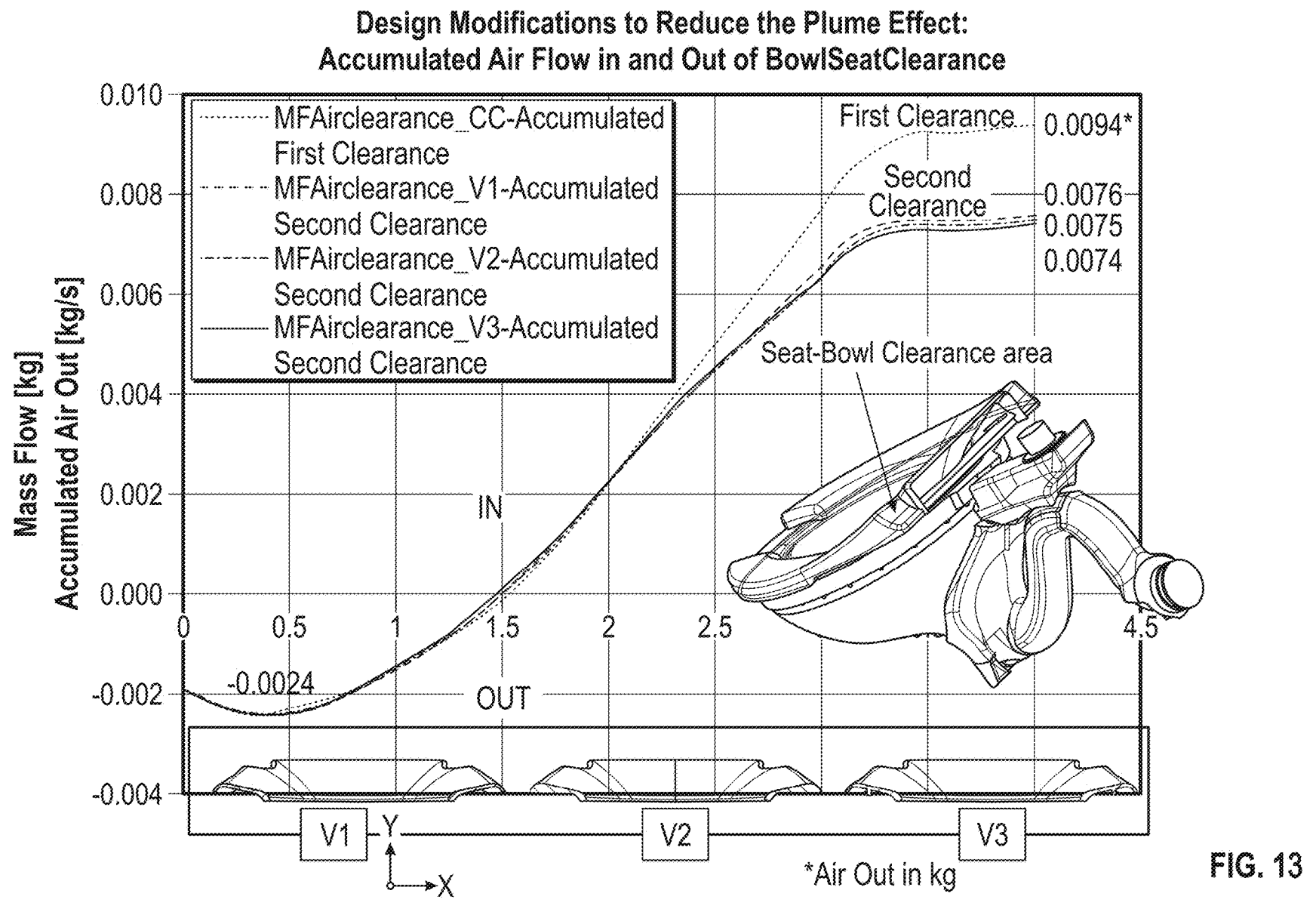

Design Modifications to Reduce the Plume Effect:
Accumulated Air Flow in and Out of BowlSeatClearance First Clearance.    0.0094*

Second          0.0076
Clearance       0.0075
                0.0074

Seat-Bowl Clearance area

------- MFAirclearance_CC-Accumulated
        First Clearance
------- MFAirclearance_V1-Accumulated
        Second Clearance
------- MFAirclearance_V2-Accumulated
        Second Clearance
------- MFAirclearance_V3-Accumulated
        Second Clearance Mass Flow [kg]
Accumulated Air Out [kg/s]

*Air Out in kg

1900

1701

1741

1751          1761

1731

1702

1742

1752     1772          1770     1762

1731

1888

1889

1888

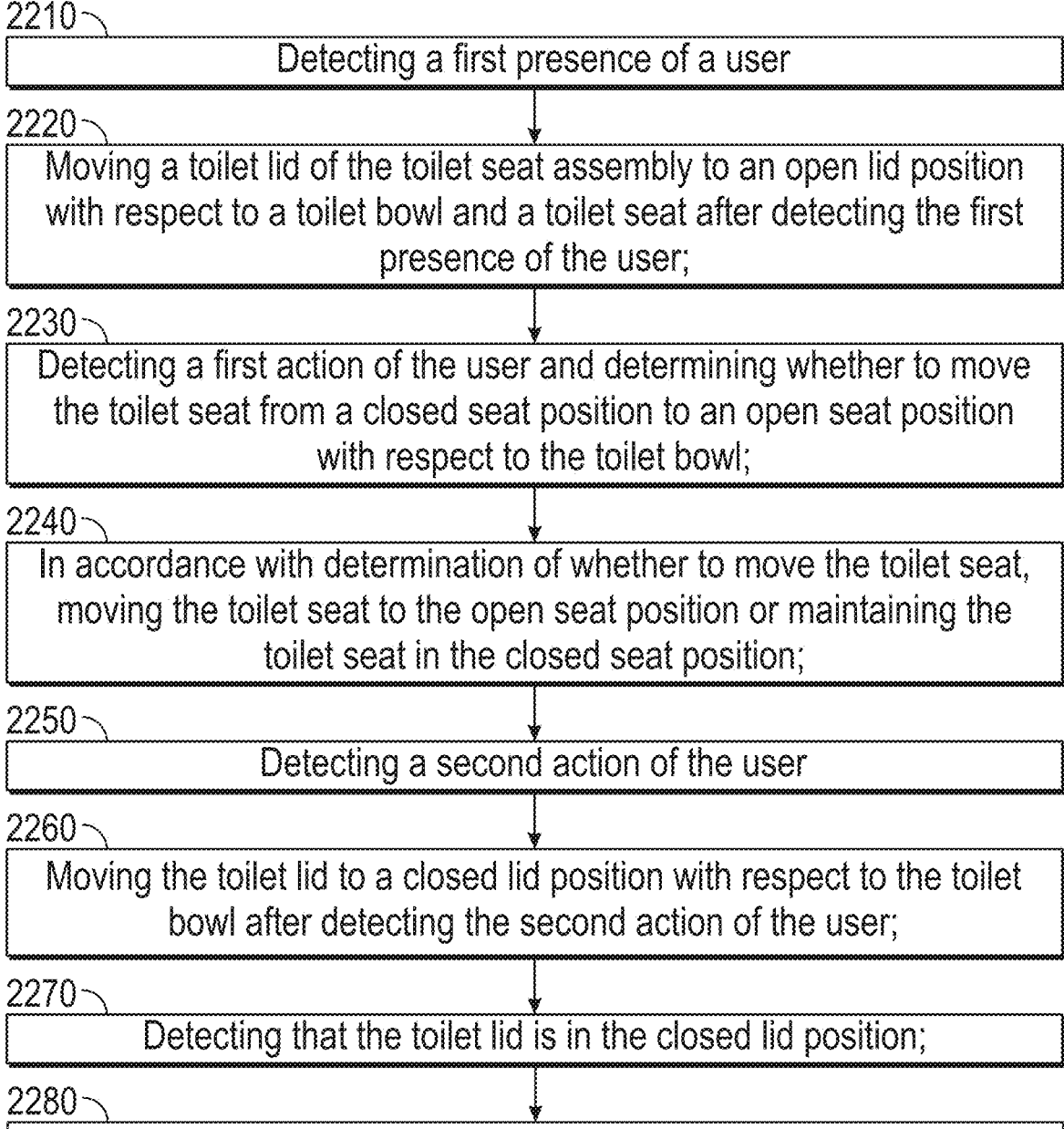

2200

2210
Detecting a first presence of a user

2220
Moving a toilet lid of the toilet seat assembly to an open lid position with respect to a toilet bowl and a toilet seat after detecting the first presence of the user;

2230
Detecting a first action of the user and determining whether to move the toilet seat from a closed seat position to an open seat position with respect to the toilet bowl;

2240
In accordance with determination of whether to move the toilet seat, moving the toilet seat to the open seat position or maintaining the toilet seat in the closed seat position;

2250
Detecting a second action of the user

2260
Moving the toilet lid to a closed lid position with respect to the toilet bowl after detecting the second action of the user;

2270
Detecting that the toilet lid is in the closed lid position;

2280
Automatically flushing the toilet when the toilet lid is in the closed lid position, wherein the amount of toilet plume entering air outside of the toilet during the automatic flushing is reduced compared a toilet with a conventional lid in the closed position

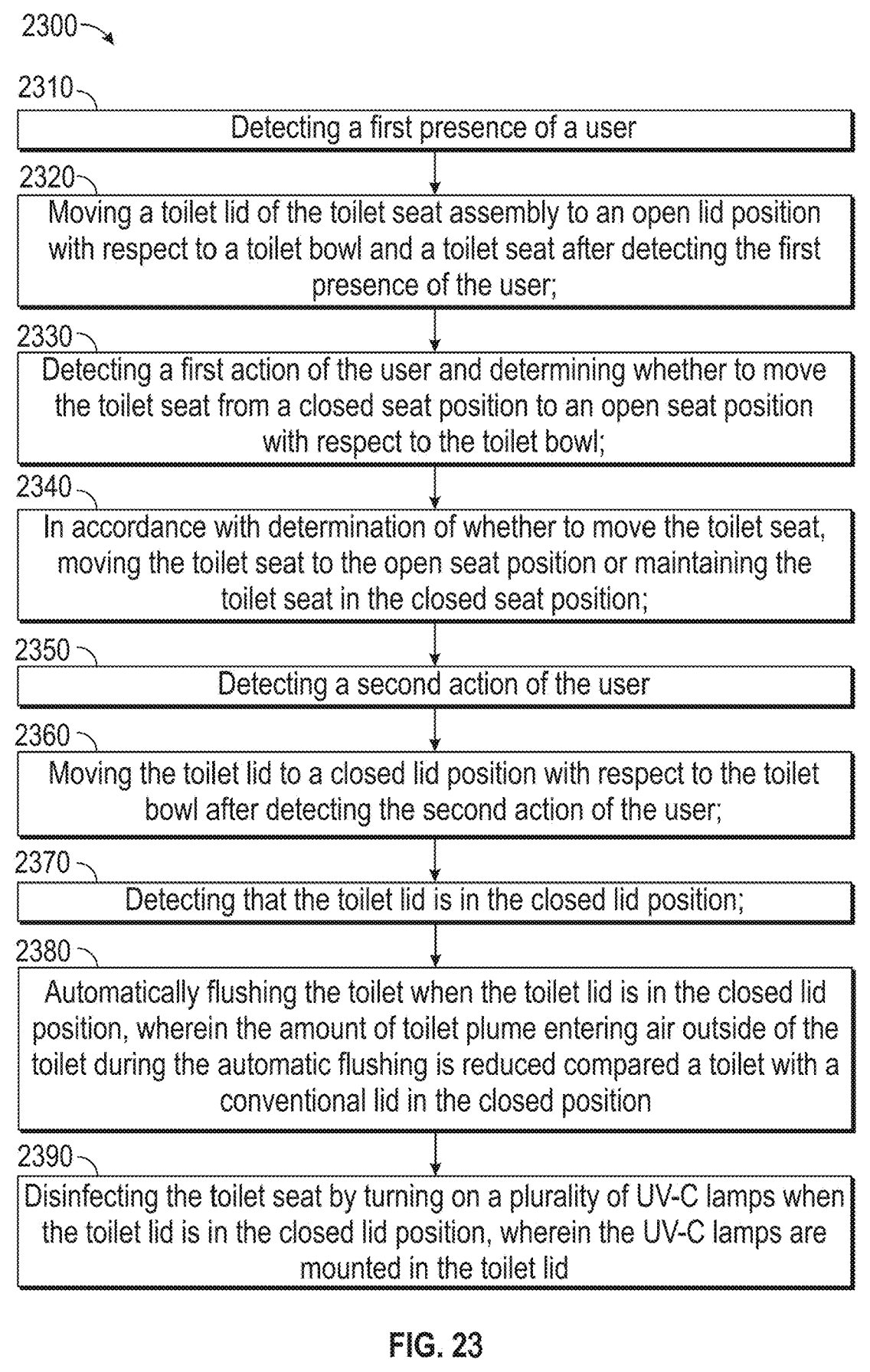

Detecting a first presence of a user

2320 —

Moving a toilet lid of the toilet seat assembly to an open lid position with respect to a toilet bowl and a toilet seat after detecting the first presence of the user;

2330 —

Detecting a first action of the user and determining whether to move the toilet seat from a closed seat position to an open seat position with respect to the toilet bowl;

2340 —

In accordance with determination of whether to move the toilet seat, moving the toilet seat to the open seat position or maintaining the toilet seat in the closed seat position;

2350 —

Detecting a second action of the user

2360 —

Moving the toilet lid to a closed lid position with respect to the toilet bowl after detecting the second action of the user;

2370 —

Detecting that the toilet lid is in the closed lid position;

2380 —

Automatically flushing the toilet when the toilet lid is in the closed lid position, wherein the amount of toilet plume entering air outside of the toilet during the automatic flushing is reduced compared a toilet with a conventional lid in the closed position

2390 —

Disinfecting the toilet seat by turning on a plurality of UV-C lamps when the toilet lid is in the closed lid position, wherein the UV-C lamps are mounted in the toilet lid

FIG. 23

TOILET SEAT ASSEMBLY WITH UV LIGHT

CROSS-REFERENCE TO RELATED APPLICATIONS

This application is a U.S. national stage application under 35 U.S.C. § 371 of International Application No. PCT/US2022/025633, filed Apr. 20, 2022, which claims the benefit of U.S. Provisional Application No. 63/177,631, filed Apr. 21, 2021, and U.S. Provisional Application No. 63/304,215 filed Jan. 28, 2022. The entire contents of each priority application is incorporated herein by reference.

FIELD OF THE DISCLOSURE

This disclosure generally relates to toilets and more specifically to toilet seat assemblies for reducing toilet plume contamination.

BACKGROUND OF THE DISCLOSURE

Flushing a toilet generates toilet plume. Toilet plume may pose health concerns as it can contaminate air around the toilet and surfaces of and around the toilet with particles derived from waste and germs associated with toilet use. Toilet plume enters into ambient air outside of the toilet bowl when water flows from the toilet tank, to the toilet bowl, out through the toilet trap outlet, and again back into the bowl as a toilet flushes. This movement of water pushes air from inside the toilet bowl to outside the toilet bowl as water flows to the toilet bowl and sucks air from outside of the toilet bowl into the toilet bowl, and as water flows from the toilet bowl out through the toilet trap outlet. In this way, the flowing water and air cause turbulent flows of toilet plume.

Covering the toilet bowl with a toilet lid during flushing can help block some air from flowing in and out of the toilet bowl, and thus reduce an amount of toilet plume from entering the ambient air around a user of the toilet. However, most public toilets do not include a toilet lid. When public toilets do include a toilet lid, most users may be uncomfortable with touching the toilet lid due to potential contamination with toilet plume from previous users or from lack of routine cleaning. This can result in users leaving the toilet lid up during flushing to avoid touching the lid.

Flushing a toilet with its lid up (or similarly, a lidless toilet) allows toilet plume to enter the atmosphere in various directions around the toilet including, for example, in a direction towards the user. Even if a user were to move a typical lid to cover an opening of the toilet seat prior to flushing, the toilet plume exiting the toilet is primarily directed to the user. Therefore, toilet plume, particularly in public bathrooms, remains a potential health concern.

SUMMARY OF THE DISCLOSURE

Disclosed herein is a toilet lid shaped to correspond to a toilet seat for reducing toilet plume that enters an atmosphere outside of the toilet into a user area during flushing. The lid includes a UV-C disinfection system in or on the lid that is configured to disinfect the seat when the lid is closed over the seat. The lid is shaped to have a conformal fit over a user surface of the seat and a planar fit over the opening of the seat. When the lid is closed over the seat, the lid covers the user surface of the seat and the opening of the seat. A conformal fit over the seat is configured to limit toilet plume from entering the user area and limit light from the UV-C disinfection system from entering the user area. According to some embodiments a toilet seat assembly includes the lid, the seat, and the UV-C disinfection system.

In some embodiments, when the lid is closed over the seat, the lid extends into the opening of the seat. The conformal fit and the extension of the lid into the opening of the seat is configured to limit deposits of toilet plume or toilet water on the seat during flushing.

The lid is movable between an open lid position and a closed lid position with respect to the toilet seat and bowl. According to some embodiments, the lid includes an edge portion configured to extend past an edge and a sidewall of the seat when the lid is in the closed lid position. In this way, when the lid is closed over the seat, the lid covers the edge and the sidewall of the seat. The edge portion is configured to direct the toilet plume that does enter the atmosphere around the user area and downward.

The seat includes a seat surface for a user to sit and the seat surface has a seat geometry around the opening of the toilet seat. In some embodiments, the lid includes an inner liner that is contoured to correspond to the seat geometry to minimize toilet plume settling on the seat surface and toilet water from wetting the seat surface when the lid is in the closed position during flushing. In some embodiments, the seat surface of the toilet seat may be made from one or more materials that inhibit the growth of bacteria on the toilet seat. In some embodiments, the one or more materials may include zinc oxide (ZnO). In some embodiments, the seat surface may include a first glaze that may include one or more of ZnO, Feldspar, Whiting, Talc, Frit, Silica, Opacifier, Clay, and other materials. In some embodiments, ZnO in the first glaze may be up to about 16 wt %. In some embodiments, the first glaze may have a post-fire thickness from about 200 microns to about 600 microns. In some embodiments, the seat surface may include a second glaze after firing that may include one or more of $SiO_2$, $Al_2O_3$, $ZRO_2$, ZnO, and CaO. In some embodiments, the ZnO in the second glaze may be from about 3 wt % to about 40 wt %. In some embodiments, the second glaze may have a post-fire thickness from about 50 microns to 500 microns.

In some embodiments, the lid may include a controller configured to automatically open and close the lid so that a user does not have to touch the lid during operation of the toilet. In some embodiments, the controller may be configured to automatically flush the toilet so that the user does not have to touch the flushing mechanism to flush the toilet. The controller may include one or more sensors configured to detect a user and an action of a user. In some embodiments, based on detection of the one or more sensors, the controller is configured to determine an action of the user and automatically open, automatically close, or automatically flush based on the detected user and the action of the user. For example, the one or more sensors may detect that a user has left the toilet and then the controller may automatically close the lid (and the seat if applicable) and subsequently automatically flush after the seat and the lid are closed to minimize the effects of toilet plume. In some embodiments, when a user approaches a toilet while the seat is in the closed seat position and the lid in the closed lid position, the one or more sensors are configured to detect the presence of the user and the controller is configured to automatically open one or more of the lid and seat based on the detected presence of the user.

The lid may be used in buildings where bathrooms are cleaned and maintained on a regular basis. For example, the lid may be used in Grade A and B office buildings and public spaces, public areas of hospitality, airports, and residential areas. The toilet seat assembly may be EPA and UL certified.

In an embodiment a "flush" or "flushing" may refer to a "flush cycle", comprising actuation of a flush valve, delivery of water to a rim and/or sump of a bowl, initiation of a siphon to direct bowl contents through the trapway to a waste pipe, and refill of the bowl to restore a water seal.

In some embodiments, the lid includes a disinfection system and when the lid is closed over the seat and the seat closed over the toilet bowl, the disinfection system is configured to disinfect the user surface of the seat. The disinfection system may automatically clean the lid is the closed lid position. In particular for public toilets, the disinfection system may help users feel more comfortable knowing that the toilet can be or has been cleaned between users. In some embodiments, an edge portion of the lid is configured to block at least some of the light from a disinfection system mounted onto the lid of the seat assembly.

The disinfection system may include one or more UV light sources to disinfect the one or more of the seat and toilet bowl after each use. In some embodiments, disinfection system may be configured to kill at least about 90%, about 95%, or about 99% of one or more of the following germs: *Escherichia Coli (E-Coli), Pseudomonas aeruginosa, Staphylococcus aureus, Klebsiella pneumonia,* MRSA, *Salmonella typhimurium, Bacillus subtillis, Vibrio parahaemolyticus,* Human Corona Virus, Influenza A virus (H3N2), and Human Rino virus.

In some embodiments, the one or more UV light sources may include a plurality of UV-C lamps or chip sets with one or more user-safe coatings. The plurality of UV-C lamps or chips may use an energy wavelength and output rate configured to kill germs in a predetermined amount of time. In some embodiments, the energy wavelength may be at least about 200 nm, about 220 nm, or about 240 nm. In some embodiments, the energy wavelength may be at most about 290 nm, about 280 nm, or about 270 nm. In some embodiments, the energy wavelength may about 200 nm-290 nm, about 220 nm-280 nm, or about 240 nm-270 nm. In some embodiments, the plurality UV-C lamps or chips may be configured to operate at a predetermined distance away from target surface to maximize disinfection and user safety. In some embodiments, the disinfection system may include a predetermined number of the plurality UV-C lamps or chips configured to kill germs. In some embodiments, the disinfection system may be configured to generate ozone gas to clean one or more of the toilet seat and the toilet bowl.

In some embodiments, the lid may include a UV-C transparent layer shaped to conform a shape of the lid and the seat. The UV-C transparent layer may be configured to cover the one or more UV-C lamps or chip sets. In some embodiments, the UV-C transparent layer may include silicone-containing plastics or rubbers. In some embodiments, the UV-C transparent layer may be configured to be prevent breakage during installation and during operation of a toilet seat assembly. In some embodiments, the UV-C transparent layer may be configured to protect lens of the UV-C transparent layer from UV-C light. In some embodiments, the UV-C transparent layer may include one or more of the following materials: ABS flame retardant, ABS/PC Blend—Acrylonitrile Butadiene Styrene/Polycarbonate Blend, ABS/PC Blend 20% Glass Fiber, ASA—Acrylonitrile Styrene Acrylate, ASA/PC Blend—Acrylonitrile Styrene Acrylate/Polycarbonate Blend, ASA/PVC Blend—Acrylonitrile Styrene Acrylate/Polyvinyl Chloride Blend, CPVC—Chlorinated Polyvinyl Chloride, ECTFE—Ethylene Chlorotrifluoroethylene, ETFE—Ethylene Tetrafluoroethylene, FEP—Fluorinated Ethylene Propylene, Ionomer (Ethylene-Methyl Acrylate Copolymer), LCP—Liquid Crystal Polymer, LCP Carbon Fiber-reinforced, LCP Glass Fiber-reinforced, LCP Mineral-filled, LDPE—Low Density Polyethylene, LLDPE—Linear Low Density Polyethylene, MABS—Transparent Acrylonitrile Butadiene Styrene, PA 11—(Polyamide 11) 30% Glass fiber reinforced, PA 11 Conductive, PA 11 Flexible, PA 11 Rigid, PA 11 or 12, PA 12 (Polyamide 12), Conductive, PA 12, Fiber-reinforced, PA 12 Flexible, PA 12, Glass Filled, PA 12 Rigid, PA 46—Polyamide 46, PA 46, 30% Glass Fiber; PA 6—Polyamide 6; PA 6-10—Polyamide 6-10; Polyamide semi-aromatic; PAI—Polyamide-Imide; PAI, 30% Glass Fiber; PARA (Polyarylamide), 30-60% glass fiber; PBT—Polybutylene Terephthalate; PBT, 30% Glass Fiber; PC—Polycarbonate; PC (Polycarbonate) 20-40% Glass Fiber; PC—Polycarbonate, high heat; PC/PBT Blend—Polycarbonate/Polybutylene Terephthalate Blend; PC/PBT blend, Glass Filled; PCTFE—Polymonochlorotrifluoroethylene; PE—Polyethylene 30% Glass Fiber; PEEK—Polyetheretherketone; PEEK 30% Carbon Fiber-reinforced; PEEK 30% Glass Fiber-reinforced; PEI—Polyetherimide; PEI, 30% Glass Fiber-reinforced; PEI, Mineral Filled; PESU—Polyethersulfone; PESU 10-30% glass fiber; PET—Polyethylene Terephthalate; PET, 30% Glass Fiber-reinforced; PETG—Polyethylene Terephthalate Glycol; PE-UHMW—Polyethylene-Ultra High Molecular Weight; PFA—Perfluoroalkoxy; PI—Polyimide; PMMA—Polymethylmethacrylate/Acrylic; PMMA (Acrylic) High Heat; PMMA (Acrylic) Impact Modified; PMP—Polymethylpentene; PMP 30% Glass Fiber-reinforced; PMP Mineral Filled; PP—Polypropylene; PP—Polypropylene 10-20% Glass Fiber; PP, 10-40% Mineral Filled; PP, 10-40% Talc Filled; PP, 30-40% Glass Fiber-reinforced; PP (Polypropylene) Copolymer; PP (Polypropylene) Homopolymer; PPE—Polyphenylene Ether; PPE, 30% Glass Fiber-reinforced; PPE, Mineral Filled; PPS—Polyphenylene Sulfide; PPS, 20-30% Glass Fiber-reinforced; PPS, 40% Glass Fiber-reinforced; PPS, Conductive; PPS, Glass fiber & Mineral-filled; PPSU—Polyphenylene Sulfone; PSU—Polysulfone; PSU, 30% Glass fiber-reinforced; PSU Mineral Filled; PTFE—Polytetrafluoroethylene; PTFE, 25% Glass Fiber-reinforced; PVC (Polyvinyl Chloride); PVC (Polyvinyl Chloride), 20% Glass Fiber-reinforced; PVC, Plasticized; PVC, Plasticized Filled; PVC Rigid; PVDC—Polyvinylidene Chloride; PVDF—Polyvinylidene Fluoride; SRP—Self-reinforced Polyphenylene; XLPE—Crosslinked Polyethylene.

In some embodiments, a toilet seat assembly includes a toilet seat comprising an inner rim around a central opening of the toilet seat and a contoured upper seat surface that extends between the inner rim and an outer rim of the toilet seat; and a lid hinged to the toilet seat and movable between an open lid position and a closed lid position with respect to a toilet bowl and the toilet seat; wherein the lid comprises an inner liner that comprises a shaped surface portion and a core portion, the shaped surface portion is shaped to correspond to the contoured upper seat surface of the toilet seat, and the core portion is joined to the shaped surface portion, and in the closed lid position the shaped surface portion of the lid covers the upper seat surface of the toilet seat, and the core portion of the lid covers the central opening of the toilet seat; a plurality of UV-C lamps positioned in one or more recessed portions of the shaped surface portion of the inner liner of the lid and configured to direct UV-C light towards the seat surface when the lid is in the closed lid position.

In any of these embodiments, the lid may be hollow between an outer liner and the inner liner, and the outer liner may cover the shaped surface portion and the core portion of the inner liner forming a hollow portion of the lid.

In any of these embodiments, the lid may include one or more support liners mounted between the outer liner and the inner liner on an internal surface of the inner liner, and walls of the one or more recessed portions may be formed by the one or more support liners, and the plurality of UV-C lamps may be mounted to the one or more support liners in the one or more recessed portions.

In any of these embodiments, the one or more recessed portions of the shaped portion of the inner liner may extend into the hollow portion of the lid towards the outer liner, and the inner liner may include a UV-C light transparent layer configured to cover the one or more recessed portions and enclose the one or more support liners in the hollow portion of the lid.

In any of these embodiments, the UV-C transparent layer may be spaced from about 0.05 to about 0.5 inches away from the seat surface.

In any of these embodiments, the UV-C light transparent layer may include a plurality of lenses.

In any of these embodiments, each lens of the plurality of lenses may include diamond shaped cuts.

In any of these embodiments, the one or more support liners may include one or more reflective pockets between the plurality of UV-C lamps.

In any of these embodiments, the lid may include an edge portion configured for covering a sidewall of the toilet seat, covering a front opening in the toilet seat, and blocking at least a portion of light from the plurality of UV-C lamps when the lid is in the closed lid position.

In any of these embodiments, when the lid is in the closed lid position, the edge portion of the inner liner may direct at least a portion of toilet plume leaving the toilet bowl and entering air outside of the toilet bowl in a downward direction.

In any of these embodiments, the plurality of UV-C lamps may be integrated circuit chips.

In any of these embodiments, the plurality of UV-C lamps may be integrated circuit chips connected via a harness of printed film circuit.

In any of these embodiments, the plurality of UV-C lamps may be integrated circuit chips, and a first set of the plurality of UV-C lamps may include a first circuit board that contacts the shaped surface portion of the inner liner and a second set of the plurality of UV-C lamps may include a second circuit board that contacts the shaped surface portion of the inner liner.

In any of these embodiments, the plurality of UV-C lamps may include a set of UV-C lamps configured to provide an illumination cone from about 90 degrees to about 150 degrees directed towards the upper seat surface.

In any of these embodiments, the lid may be a two-component lid comprising an outer liner and the inner liner, the outer liner is joined to the inner liner.

In any of these embodiments, the lid may include a hollow portion between the outer liner and the inner liner.

In any of these embodiments, the upper seat surface may be inclined downward from the outer rim of the toilet seat to the inner rim of the toilet seat towards the central opening.

In any of these embodiments, a lid-to-seat clearance between the shaped surface portion of the lid and the upper seat surface of the toilet seat may be on average from about 0.05 to about 0.5 inches when the lid is in the closed lid position.

In any of these embodiments, a seat-to-bowl clearance between a bottom surface of the toilet seat and an upper rim of the toilet bowl may be on average from about 0.05 to about 0.5 inches when the lid is in the closed lid position and the toilet seat is in the closed seat position.

In any of these embodiments, the lid in the closed position may be configured to allow a reduced mass of air that enters the toilet during a flush by from about 20% to about 80% compared to a conventional mass of air that enters a conventional toilet during a flush when a conventional lid of the conventional toilet is in an open position, wherein the conventional toilet may be configured to flush from 0.8 gallons to 1.6 gallons per flush.

In any of these embodiments, the reduced mass of air may be from about 3 grams to about 18 grams of air.

In any of these embodiments, the reduced mass of air may be configured to reduce an amount of toilet plume that leaves the toilet bowl and enters air outside of the toilet bowl after flushing.

In any of these embodiments, the inner rim of the seat may extend completely around the central opening of the seat.

In any of these embodiments, a toilet seat system may include the toilet seat assembly; a first control system comprising one or more first sensors configured to detect a user and a position of the lid; and a controller configured to determine an action of the user, automatically move the lid between the open lid position and the closed lid position based on the action of the user determined by the controller, automatically flush the toilet when the lid is in detected to be in the closed lid position; and automatically disinfect the toilet seat by turning on a plurality of UV-C lamps when the lid is in the closed lid position; wherein an amount of toilet plume entering air outside of the toilet bowl during the automatic flushing is reduced compared a toilet with a conventional lid in the closed position.

In any of these embodiments, the controller may be configured to automatically flush the toilet only when the lid is in the closed lid position.

In any of these embodiments, the lid may include an outer liner configured to cover the shaped surface portion and the core portion of the inner liner, and the one or more sensors may be positioned on one or more of the outer liner and the inner liner.

In any of these embodiments, a method of controlling the toilet seat assembly of a toilet to reduce an amount of toilet plume entering air outside of the toilet may include detecting a fist presence of a user; moving a toilet lid of the toilet seat assembly from a closed lid position to an open lid position with respect to a toilet bowl after detecting the first presence of the user; detecting a first action of the user and determining whether to move the toilet seat from a closed seat position to an open seat position with respect to the toilet bowl; in accordance with determination of whether to move the toilet seat, moving the toilet seat to the open seat position or maintaining the toilet seat in the closed seat position; detecting a second action of the user; moving the toilet lid to a closed lid position with respect to the toilet bowl after detecting the second action of the user; detecting that the toilet lid is in the closed lid position; automatically flushing the toilet when the toilet lid is in the closed lid position, wherein the amount of toilet plume entering air outside of the toilet during the automatic flushing is reduced compared a toilet with a conventional lid in the closed position; and disinfecting the toilet seat by turning on a plurality of UV-C lamps when the toilet lid is in the closed lid position, wherein the UV-C lamps are mounted in the toilet lid.

In any of these embodiments, the toilet seat may include an inner rim around a central opening of the toilet seat and a contoured upper seat surface that extends between the inner rim and an outer rim of the toilet seat and the toilet lid comprises an inner liner that comprises a shaped surface portion and a core portion, the shaped surface portion of the lid is shaped to correspond to the contoured upper seat surface of the toilet seat, wherein in the closed lid position the shaped surface portion of the lid covers the upper seat surface of the toilet seat, and the core portion of the lid covers the central opening of the toilet seat, and wherein the plurality of UV-C lamps are positioned in one or more recessed portions of the shaped surface portion of the inner liner of the lid and configured to direct UV-C light towards the seat surface when the lid is in the closed lid position.

In any of these embodiments, the lid may include an outer liner and the lid is hollow between the outer liner and the inner liner, and the outer liner may cover the shaped surface portion and the core portion of the inner liner forming a hollow portion of the lid.

In any of these embodiments, the lid may include one or more support liners mounted between the outer liner and the inner liner on an internal surface of the inner liner, and the walls of the one or more recessed portions may be formed by the one or more support liners, and the plurality of UV-C lamps may be mounted to the one or more support liners in the one or more recessed portions.

In any of these embodiments, the one or more recessed portions of the shaped portion of the inner liner may extend into the hollow portion of the lid towards the outer liner, and the inner liner may include a UV-C light transparent layer configured to cover the one or more recessed portions and enclose the one or more support liners in the hollow portion of the lid.

In any of these embodiments, the UV-C transparent layer may be spaced from about 0.05 to about 0.5 inches away from the seat surface.

In any of these embodiments, the UV-C light transparent layer may include a plurality of lenses.

In any of these embodiments, each lens of the plurality of lenses may include diamond shaped cuts.

In any of these embodiments, the one or more support liners may include one or more reflective pockets between the plurality of UV-C lamps.

In any of these embodiments, the lid may include an edge portion configured for covering a sidewall of the toilet seat, covering a front opening in the toilet seat, and blocking at least a portion of light from the plurality of UV-C lamps when the lid is in the closed lid position.

In any of these embodiments, when the lid is in the closed lid position, the edge portion of the inner liner may direct at least a portion of toilet plume leaving the toilet bowl and entering air outside of the toilet bowl in a downward direction.

In any of these embodiments, the plurality of UV-C lamps may be integrated circuit chips, and a first set of the plurality of UV-C lamps may include a first circuit board that contacts the shaped surface portion of the inner liner and a second set of the plurality of UV-C lamps may include a second circuit board that contacts the shaped surface portion of the inner liner.

In any of these embodiments, the plurality of UV-C lamps may include a set of UV-C lamps configured to provide an illumination cone from about 90 degrees to about 150 degrees directed towards the upper seat surface.

In any of these embodiments, the upper seat surface may be inclined downward from the outer rim of the toilet seat to the inner rim of the toilet seat towards the central opening.

In any of these embodiments, a lid-to-seat clearance between the shaped surface portion of the lid and the upper seat surface of the toilet seat may be on average from about 0.05 to about 0.5 inches when the lid is in the closed lid position.

In any of these embodiments, a seat-to-bowl clearance between a bottom surface of the toilet seat and an upper rim of the toilet bowl may be on average from about 0.05 to about 0.5 inches when the lid is in the closed lid position and the toilet seat is in the closed seat position.

In any of these embodiments, the lid in the closed position may be configured to allow a reduced mass of air that enters the toilet during a flush by from about 20% to about 80% compared to a conventional mass of air that enters a conventional toilet during a flush when a conventional lid of the conventional toilet is in an open position, wherein the conventional toilet may be configured to flush from 0.8 gallons to 1.6 gallons per flush.

In any of these embodiments, the reduced mass of air may be from about 3 grams to about 18 grams of air.

In any of these embodiments, the reduced mass of air may be configured to reduce an amount of toilet plume that leaves the toilet bowl and enters air outside of the toilet bowl after flushing.

In any of these embodiments, the plurality of UV-C lamps may be integrated circuit chips.

In any of these embodiments, the plurality of UV-C lamps may be integrated circuit chips connected via a harness of printed film circuit.

In any of these embodiments, the method may include detecting a second presence of a user, and after detecting the second presence of the user, repeating moving the toilet lid, detecting the first action, moving the toilet to the open seat position or maintaining the toilet seat in the closed seat position, detecting the second action of the user, moving the toilet lid to the closed lid position, detecting the toilet lid in the closed lid position, automatically flushing the toilet, and disinfecting the toilet seat.

In any of these embodiments, the detecting the second presence of the user during disinfection of the toilet seat may be configured to stop disinfection of the toilet seat prior to moving the toilet lid from the closed lid position to the open lid position.

In any of these embodiments, the second action of the user may include the user moving away from the toilet.

In some embodiments, a toilet lid is configured to cover a contoured upper seat surface of a toilet seat and a central opening of the toilet seat, the contoured upper seat surface extends between an inner rim and an outer rim of the toilet seat, the lid includes: an inner liner that comprises a shaped surface portion and a core portion, the shaped surface portion is shaped to correspond to the contoured upper seat surface of the toilet seat, and the core portion is joined to the shaped surface portion; and a plurality of UV-C lamps positioned in one or more recessed portions of the shaped surface portion of the inner liner of the lid and configured to direct UV-C light towards the seat surface when the lid is in the closed lid position; wherein in the closed lid position the shaped surface portion of the lid covers the upper seat surface of the toilet seat, and the core portion of the lid covers the central opening of the toilet seat; and wherein the lid is hinged to the toilet seat and movable between an open lid position and a closed lid position with respect to a toilet bowl and the toilet seat.

In any of these embodiments, the lid may be hollow between an outer liner and the inner liner, and the outer liner may cover the shaped surface portion and the core portion of the inner liner forming a hollow portion of the lid.

In any of these embodiments, the lid may include one or more support liners mounted between the outer liner and the inner liner on an internal surface of the inner liner, and walls of the one or more recessed portions may be formed by the one or more support liners, and the plurality of UV-C lamps may be mounted to the one or more support liners in the one or more recessed portions.

In any of these embodiments, wherein the one or more recessed portions of the shaped portion of the inner liner extends into the hollow portion of the lid towards the outer liner, and the inner liner comprises a UV-C light transparent layer configured to cover the one or more recessed portions and enclose the one or more support liners in the hollow portion of the lid.

In any of these embodiments, the UV-C transparent layer may be spaced from about 0.05 to about 0.5 inches away from the seat surface.

In any of these embodiments, the UV-C light transparent layer may include a plurality of lenses.

In any of these embodiments, each lens of the plurality of lenses may include diamond shaped cuts.

In any of these embodiments, the one or more support liners may include one or more reflective pockets between the plurality of UV-C lamps.

In any of these embodiments, the lid may include an edge portion configured for covering a sidewall of the toilet seat, covering a front opening in the toilet seat, and blocking at least a portion of light from the plurality of UV-C lamps when the lid is in the closed lid position.

In any of these embodiments, when the lid is in the closed lid position, the edge portion of the inner liner may direct at least a portion of toilet plume leaving the toilet bowl and entering air outside of the toilet bowl in a downward direction.

In any of these embodiments, the plurality of UV-C lamps may be integrated circuit chips.

In any of these embodiments, the plurality of UV-C lamps may be integrated circuit chips connected via a harness of printed film circuit.

In any of these embodiments, the plurality of UV-C lamps may be integrated circuit chips, and a first set of the plurality of UV-C lamps may include a first circuit board that contacts the shaped surface portion of the inner liner and a second set of the plurality of UV-C lamps may include a second circuit board that contacts the shaped surface portion of the inner liner.

In any of these embodiments, the plurality of UV-C lamps may include a set of UV-C lamps configured to provide an illumination cone from about 90 degrees to about 150 degrees directed towards the upper seat surface.

In any of these embodiments, the lid may be a two-component lid comprising an outer liner and the inner liner, the outer liner is joined to the inner liner.

In any of these embodiments, the lid may include a hollow portion between the outer liner and the inner liner.

In any of these embodiments, the upper seat surface may be inclined downward from the outer rim of the toilet seat to the inner rim of the toilet seat towards the central opening.

In any of these embodiments, a lid-to-seat clearance between the shaped surface portion of the lid and the upper seat surface of the toilet seat may be on average from about 0.05 to about 0.5 inches when the lid is in the closed lid position.

In any of these embodiments, a seat-to-bowl clearance between a bottom surface of the toilet seat and an upper rim of the toilet bowl may be on average from about 0.05 to about 0.5 inches when the lid is in the closed lid position and the toilet seat is in the closed seat position.

In any of these embodiments, the lid in the closed position may be configured to allow a reduced mass of air that enters the toilet during a flush by from about 20% to about 80% compared to a conventional mass of air that enters a conventional toilet during a flush when a conventional lid of the conventional toilet is in an open position, wherein the conventional toilet is configured to flush from 0.8 gallons to 1.6 gallons per flush.

In any of these embodiments, the reduced mass of air may be from about 3 grams to about 18 grams of air.

In any of these embodiments, the reduced mass of air may be configured to reduce an amount of toilet plume that leaves the toilet bowl and enters air outside of the toilet bowl after flushing.

In any of these embodiments, the inner rim of the seat may extend completely around the central opening of the seat.

In any of these embodiments, a toilet seat system may include the lid; a first control system comprising one or more first sensors configured to detect a user and a position of the lid; and a controller configured to determine an action of the user, automatically move the lid between the open lid position and the closed lid position based on the action of the user determined by the controller, automatically flush the toilet when the lid is in detected to be in the closed lid position; and automatically disinfect the toilet seat by turning on a plurality of UV-C lamps when the lid is in the closed lid position; wherein an amount of toilet plume entering air outside of the toilet bowl during the automatic flushing is reduced compared a toilet with a conventional lid in the closed position.

In any of these embodiments, the controller may be configured to automatically flush the toilet only when the lid is in the closed lid position.

In any of these embodiments, the lid may include an outer liner configured to cover the shaped surface portion and the core portion of the inner liner, and the one or more sensors may be positioned on one or more of the outer liner and the inner liner.

In some embodiments, provided is a toilet seat assembly, the toilet seat assembly comprising: a toilet seat comprising an inner rim around a central opening of the toilet seat and a contoured upper seat surface that extends between the inner rim and an outer rim of the toilet seat; a lid hinged to the toilet seat and movable between an open lid position and a closed lid position with respect to a toilet bowl and the toilet seat; and a dynamic UV-C light mechanism comprising: a track complementary in shape to the upper seat surface of the toilet seat and positioned on an underside of the lid, such that the track faces the upper seat surface of the toilet seat when the lid is in the closed lid position; one or more UV-C lamps configured to travel around a perimeter of the track and configured to direct light towards the seat surface when the lid is in a closed lid position.

In some embodiments of the toilet seat assembly, the dynamic UV-C light mechanism comprises one or more arms, each arm of the one or more arms configured to pivot at a proximal end from a central location within the track, wherein each arm extends from its proximal end at the central location to a distal end, the distal end in contact with the track and configured to move 360 degrees around the track.

In some embodiments of the toilet seat assembly, the one or more UV-C lamps are located at the distal end of each of the one or more arms.

In some embodiments of the toilet seat assembly, the one or more arms is configured to couple to the track using a pin.

In some embodiments of the toilet seat assembly, the one or more arms is configured to couple to the track using a roller bearing mechanism.

In some embodiments of the toilet seat assembly, the one or more arms comprises a wheel at the distal end of each arm that is configured to roll along an interior surface of the track.

In some embodiments of the toilet seat assembly, the one or more arms is telescoping.

In some embodiments of the toilet seat assembly, the one or more arms is spring-loaded.

In some embodiments of the toilet seat assembly, a cleaning cycle of the dynamic UV-C light mechanism is automatically initiated when the toilet lid assumes its closed lid position.

In some embodiments of the toilet seat assembly, a cleaning cycle of the dynamic UV-C light mechanism is manually initiated by a user.

In some embodiments of the toilet seat assembly, the dynamic UV-C light mechanism comprises a motor configured to cause the one or more UV-C lamps to rotate around the track.

In some embodiments of the toilet seat assembly, the one or more UV-C lamps are integrated circuit chips.

In some embodiments of the toilet seat assembly, the one or more UV-C lamps are integrated circuit chips connected via a harness of printed film circuit.

In addition, it is also to be understood that the singular forms "a", "an," and "the" used in the following description are intended to include the plural forms as well, unless the context clearly indicates otherwise. It is also to be understood that the term "and/or," as used herein, refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

In the following description of the disclosure and embodiments, reference is made to the accompanying drawings in which are shown, by way of illustration, specific embodiments that can be practiced. It is to be understood that other embodiments and examples can be practiced, and changes can be made, without departing from the scope of the disclosure.

BRIEF DESCRIPTION OF THE DRAWINGS

The disclosure will now be described, by way of example only, with reference to the accompanying drawings, in which:

FIG. 13 shows an example of mass flow data for different seat assemblies, according to some embodiments;

FIG. 22 illustrates a flowchart of an exemplary method for controlling an automatic toilet seat assembly of a toilet and reducing an amount of toilet plume entering air outside of the toilet, according to some embodiments;

FIG. 23 illustrates a flowchart of an exemplary method for controlling an automatic toilet seat assembly of a toilet and reducing an amount of toilet plume entering air outside of the toilet, according to some embodiments.

DETAILED DESCRIPTION OF THE DISCLOSURE

Disclosed herein is a lid hinged to a seat and movable to a closed lid position in which the lid is closed over the seat and toilet bowl to minimize toilet plume during flushing. The lid includes a plurality of UV-C lamps in or on the lid configured to disinfect the seat when the lid is closed over the seat. According to some embodiments, a toilet seat assembly may include the lid, the seat, and the plurality of UV-C lamps.

Figure 1A:
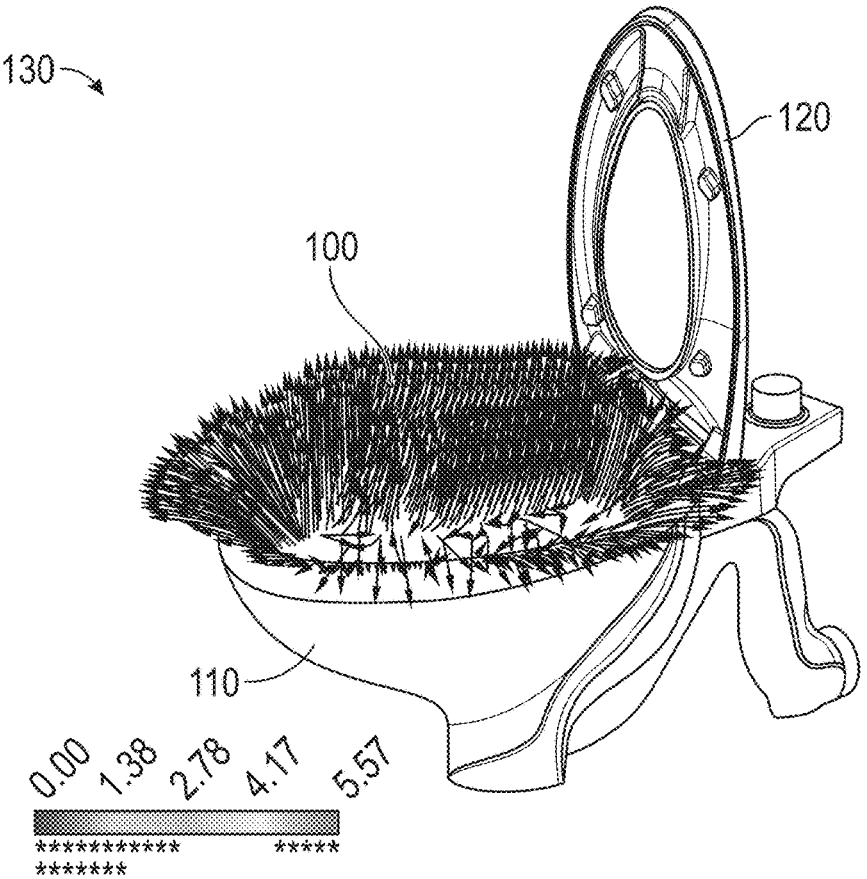
FIGS. 1A and 1B respectively show exemplary air vector fields 100 from the toilet bowl 110 during flushing when a lid 120 of a toilet seat assembly is in an open lid positon and a closed lid position, according to some embodiments.
Figure 1B:
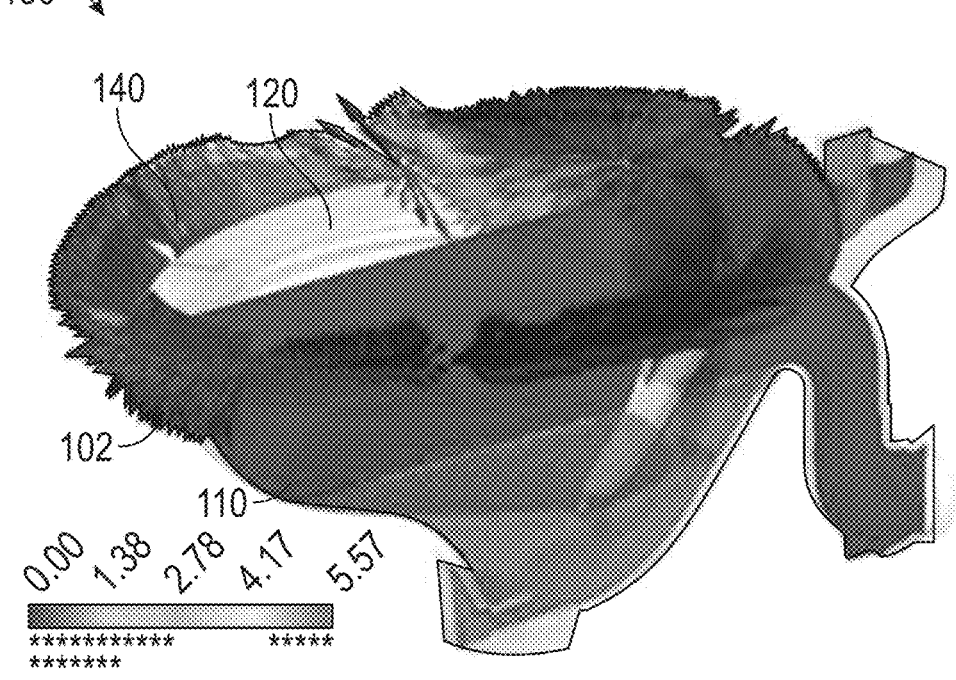

According to some embodiments, air moved between a toilet bowl and a user area during flushing may be dependent on a structure of the lid and a position of the lid. FIGS. 1A and 1B respectively show exemplary air vector fields 100 from the toilet bowl 110 during flushing when a lid 120 of a toilet seat assembly is in an open lid positon and a closed lid position, according to some embodiments. The lid is movable between the open lid position and the closed lid position with respect to a toilet bowl. As shown in FIG. 1A, when the lid 120 is in the open lid position during flushing, the air vector fields 100 indicate that air from inside the toilet bowl 110 (referred to as toilet plume) travels in various directions out of the toilet bowl 110 into a user area 130 of the toilet. For example, the air vector fields 100 show that the toilet plume travels from inside the toilet bowl 110 to outside of the toilet bowl 110 in upward, sideways, and downward directions. The lid 110 in the closed lid position is configured to block toilet plume leaving from a topside of the toilet bowl 110 and redirect toilet plume that does leave the toilet bowl 110 into the user area in a downward direction. For example, FIG. 1B shows when the lid 120 is in the closed lid position during flushing, the air vector fields 140 show that toilet plume does not leave the toilet bowl 110 from a topside of the toilet bowl 110 and more of the toilet plume leaving the toilet bowl 110 into the user area 130 is directed downwards 102 compared to the open lid position configuration in FIG. 1A. According to some embodiments, the toilet plume that leaves the toilet bowl 110 is directed downward at the out and back towards a rear of the toilet in the user area.

Figure 2A:
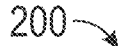
FIG. 2A shows an example of a toilet seat assembly, according to some embodiments.

FIG. 2A shows an example of a toilet seat assembly, according to some embodiments. The toilet seat assembly 200 of FIG. 2A is configured to reduce toilet plume from entering a user area outside of a toilet bowl during flushing when the lid is closed over the seat and toilet bowl. The toilet seat assembly 200 includes a seat 210 and a lid 220. The seat 210 may include a contoured upper seat surface 230 around a central opening 240 of the seat. In some embodiments, front ends 250a, 250b of the contoured upper seat surface 230 seat 210 may be spaced apart to form a front opening 260. The upper seat surface 230 extends from an inner rim 270 to an outer rim 280. A shape of the upper seat surface 230 may be configured to provide a seat for a user to sit. The shape of the upper seat surface 230 may be contoured towards the inner rim 270 and the central opening 240. When the seat 210 is in a closed seat position, the contoured upper seat surface is inclined in a downward direction towards the inner rim 270 and an interior of the toilet bowl. According to some embodiments, a downward incline (for example, such as incline B in FIG. 5) of the contoured upper seat surface may be at least about 15 degrees, 30 degrees, or 45 degrees from a horizontal (for example, horizontal line A in FIG. 5). According to some embodiments, a downward incline (for example, such as incline B in FIG. 5) of the contoured upper seat surface may be at most about 85 degrees, 65 degrees, or 55 degrees from a horizontal (for example, horizontal line A in FIG. 5). According to some embodiments, a downward incline (for example, such as incline B in FIG. 5) of the contoured upper seat surface may be about 15-85 degrees, 30-65 degrees, or 45-55 degrees from a horizontal (for example, horizontal line A in FIG. 5).

According to some embodiments, the lid 220 may include an inner liner 221 configured to cover the seat 210. The inner liner may include a shaped surface portion 222 and a core portion 224 configured to respectively cover the upper seat surface 230 and the central opening 240 of the seat 210. The shaped surface portion 222 of the inner liner 221 is shaped to correspond to the contoured upper seat surface 230 of the seat 210. For example, the shaped surface portion 222 may be shaped to correspond to a contour of the upper seat surface 230 from the inner rim 270 to the outer rim 280 of the seat 210. The shaped surface portion 222 may include a sidewall 227 that is configured to extend over at least a portion of the sidewall 284 of the seat when the lid 220 is in a closed lid position over the seat 210 and the toilet bowl.

According to some embodiments, the shaped surface portion 222 of the inner liner 221 includes a front cover 228. The front cover 228 is configured to cover the front opening 260 of the seat 210 when the lid 220 in the closed lid position over the seat 210 and the toilet bowl. When the front cover 228 covers the front opening 260 of the seat 210, air travel between the toilet bowl and the user area is restricted. For example, at least a portion of toilet plume from inside the toilet bowl is blocked from entering the user area through the front opening 260 and air in the user area is blocked from entering the toilet bowl. The front cover 228 may include a first edge 229a and a second edge 229b. The first edge 229a may be configured to extend along the first edge 250a of the seat 210 and the second edge 229b may be configured to extend along with the second edge 250b of the seat 210. When the lid 220 is in its closed lid position over the seat 210, the edges 229a, 229b extend along the edges 250a, 250b of the seat to provide a conformal cover over the seat 210 and the front opening 260 of the seat 210. According to some embodiments, the front cover 228 may include a front edge 229c. The front edge 229c may be part of the sidewall 227 of the shaped surface portion 222. The edges 229a, 229b, 229c of the front cover 228 of the shaped surface portion 222 of the inner lid 221 help to block air travel between the toilet bowl and the user area when the lid 220 is closed over the seat 210 during flushing.

The core portion 224 of the inner liner 221 may be positioned radially inward of the shaped surface portion 222 of the inner liner 221. According to some embodiments, the core portion 224 and the surface portion 222 may be joined as a single piece. An outer perimeter of the core portion 224 and an inner perimeter of the shaped surface portion 222 of the inner liner 221 may be joined at a rim 225. When the lid 220 is in a closed lid position over the seat 210, the shaped surface portion 222 of the inner liner 221 covers the upper seat surface 230 of the seat 210 and the core portion 224 of the inner liner 221 covers the central opening 240 of the seat 210.

According to some embodiments, the lid 220 may be a two-component lid that includes the inner liner 221 and an outer liner 226. The two-component lid may form a one-piece lid. The outer liner 226 may be configured to cover the inner liner 221. According to some embodiments, the outer liner 226 covers a surface of the shaped surface portion 222 and a surface of the core portion 224 of the inner liner 221 that face away from the toilet bowl when the lid is in the closed lid position. According to some embodiments, the outer liner 226 covers a surface of the front cover 228 that faces away from the toilet bowl when the lid is in the closed lid position. According embodiments, the outer liner 226 covers at least a portion of the sidewall 227 of the inner liner 221.

Figures 2B, 2C:
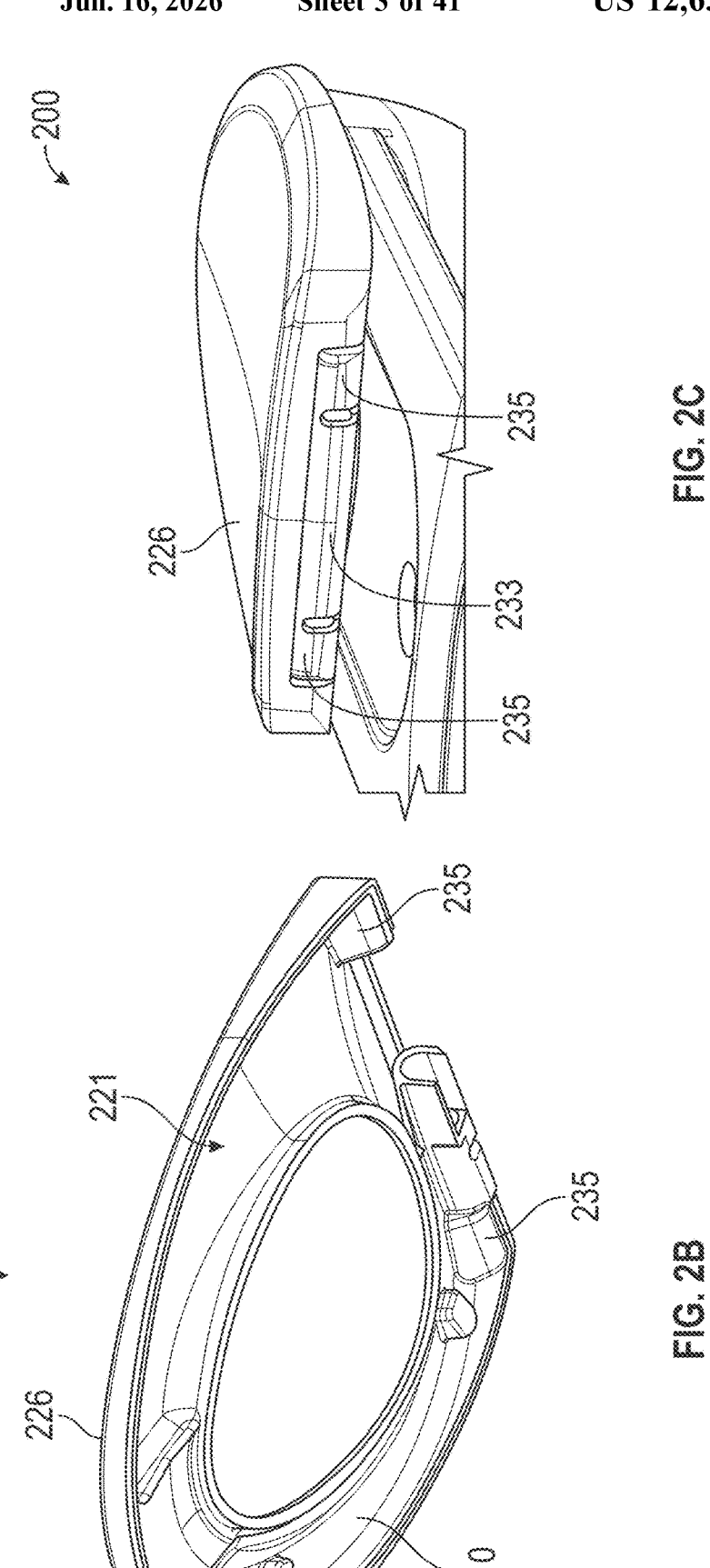
FIGS. 2B and 2C show examples of a seat and a lid in their respective closed positions with respect to a toilet bowl, according to some embodiments.
Figure 2D:
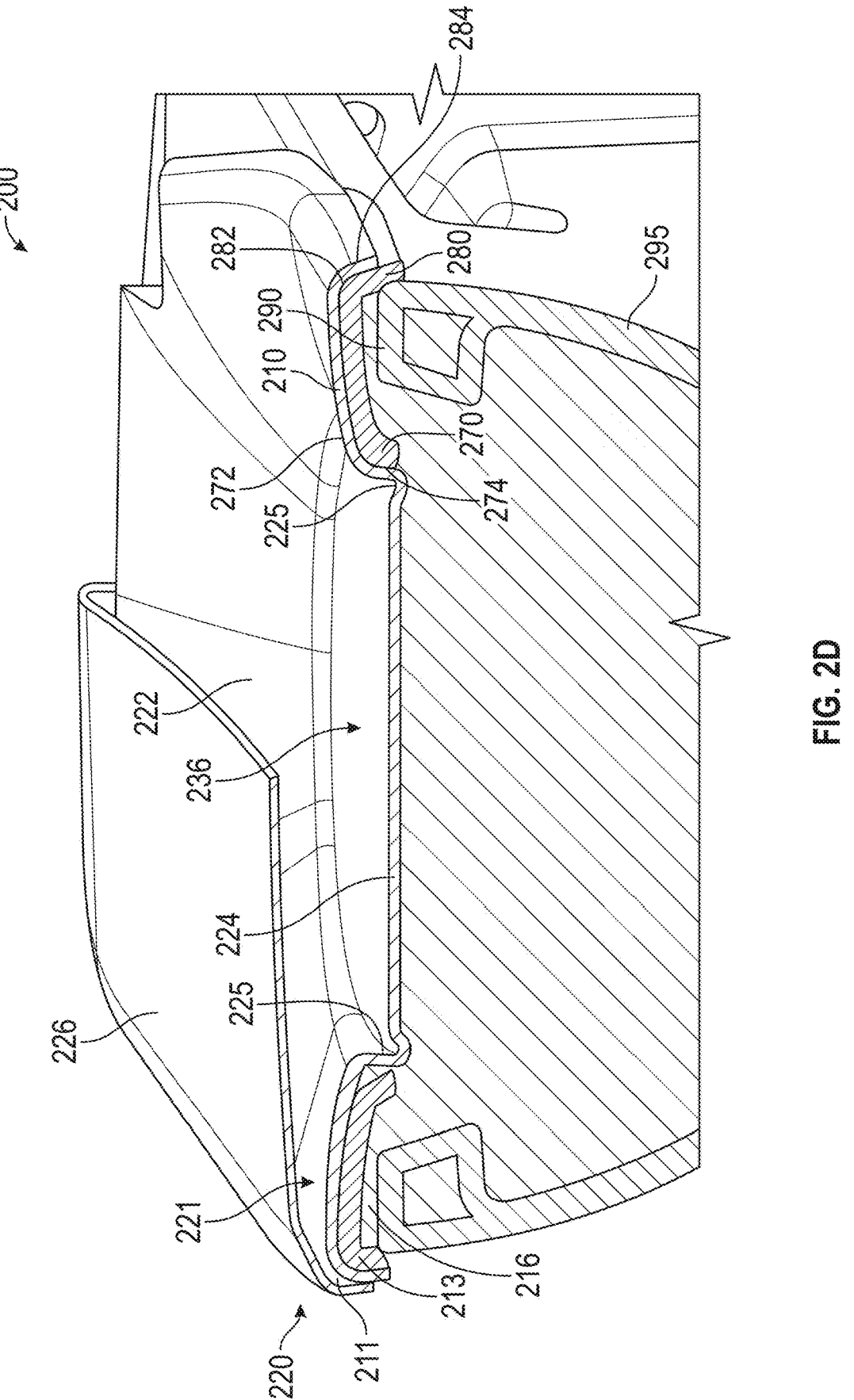
FIG. 2D shows a cross-sectional view of an exemplary seat assembly, according to some embodiments.

A lid of the seat assembly may be compatible with a plurality of seats. FIGS. 2D, 3C, and 4C each shows an example of a seat, according to some embodiments. According to some embodiments, the seat assembly 200 may be attached to a toilet via a hinge assembly 233. The seat assembly may include hinge joints 235 that allows the lid 220 and the seat 210 to move relative to other and a toilet. The seat of the seat assembly is movable between an open seat position and closed seat position and the lid of the seat assembly is movable between an open lid position and a closed lid position. When the seat is in its open seat position, the lid is in its open lid position. When the lid is in its closed lid position, the seat is in its closed lid position. FIG. 2B and FIG. 2C show examples of a seat and a lid in their respective closed positions with respect to a toilet bowl, according to some embodiments (the toilet bowl is not shown in FIG. 2B). FIG. 2B shows an underside view of the seat and the lid of the seat assembly 200 in their respective closed positions. As shown in FIG. 2B and FIG. 2C, the outer liner 226 covers the inner liner 221 when the lid 220 is in the closed lid position over the seat 210. FIG. 2C shows an example of a rearview of the seat and the lid in their respective closed positions.

FIG. 2D shows a cross-sectional view of an exemplary seat assembly on a toilet, according to some embodiments. In the example of FIG. 2D, the seat 210 includes a cored-out geometry on a bottom side 216 of the seat 210 that faces an upper rim 290 of a toilet bowl 295. The bottom side 216 of the seat 210 may be configured to cover at least a portion of a perimeter of the upper rim 290 of the toilet bowl 295. The lid 220 of the seat assembly 200 may be a two-component lid that includes the inner liner 221 and the outer liner 226 configured to cover the inner liner 221. The core portion 224 and the shaped surface portion 222 may be joined adjacent to an upper edge 272 of an inner rim 270 of the seat 210. According to some embodiments, the core portion 224 and the shaped surface portion 222 may be joined at a rim 225 of the inner liner 221. According to some embodiments, the rim 225 may be a recessed rim between the core portion 224 and the shaped surface portion 222. In the closed lid position, as shown in FIG. 2D, the rim 225 is recessed in a downward direction towards the toilet bowl 295. According to some embodiments, in the closed lid position, one or more of the rim 225, the shaped surface portion 222, and the core portion 224 may extend down to the inner rim 270 of the seat 210 or past the inner rim 270 of the seat 210. According to some embodiments, in the closed lid position, one or more of the rim 225, the shaped surface portion 222, and the core portion 224 may extend down past the inner rim 270 of the seat 210 to a bottom edge 274 of the inner rim 270 of the seat 210.

According to some embodiments, in the closed lid position, the inner liner 221 may be spaced from the seat 210 by a lid-to-seat clearance 211. In some embodiments, the lid-to-seat clearance 211 may be configured to block a portion of toilet plume from flowing over the seat and into the user area during flushing. In some embodiments, the lid-to-seat clearance 211 may be configured to block a portion of air in the user area from flowing over the seat 211 and into the toilet bowl during flushing. In some embodiments, an average lid-to-seat clearance may be at least any of about 0.05 inches, about 0.10 inches, about 0.15 inches, about 0.20 inches, about 0.25 inches, or about 0.30 inches. In some embodiments, the average lid-to-seat clearance may be at most any of about 0.50 inches, about 0.45 inches, about 0.40 inches, or about 0.35 inches. In some embodiments, the average lid-to-seat clearance may be any of about 0.05-0.50 inches, about 0.10-0.45 inches, about 0.15-0.40 inches, about 0.20-0.35 inches, or about 0.25-0.30 inches. In some embodiments, the term "shaped to correspond" may mean wherein an average lid-to-seat clearance is within these ranges; or may mean clearance at any point is within these ranges.

According to some embodiments, in the closed lid position, the seat 210 may be spaced from the upper rim 290 of the toilet bowl 295 by a seat-to-bowl clearance 213. In some embodiments, the seat-to-bowl clearance 213 may be configured to block a portion of toilet plume from flowing over the upper rim 290 of the toilet bowl 295 and into the user area during flushing. In some embodiments, the seat-to-bowl clearance 213 may be configured to block a portion of air in the user area from flowing over upper rim 290 of the toilet bowl 295 and into the toilet bowl during flushing. In some embodiments, an average seat-to-bowl clearance may be at least any of about 0.05 inches, about 0.10 inches, about 0.15 inches, about 0.20 inches, about 0.25 inches, or about 0.30 inches. In some embodiments, the average seat-to-bowl clearance may be at most any of about 0.50 inches, about 0.45 inches, about 0.40 inches, or about 0.35 inches. In some embodiments, the average seat-to-bowl clearance may be any of about 0.05-0.50 inches, about 0.10-0.45 inches, about 0.15-0.40 inches, about 0.20-0.35 inches, or about 0.25-0.30 inches. In some embodiments, the term "shaped to correspond" may mean wherein an average seat-to-bowl clearance is within these ranges; or may mean clearance at any point is within these ranges.

According to some embodiments, the shaped surface portion 222 of the inner liner 221 may include an edge portion 223 that is configured to extend from an upper edge 282 of the outer rim 280 of the seat 210 when the lid 220 is in a closed lid position over the seat 210 and the toilet bowl 295. In the closed lid position, the edge portion 223 extends over the upper edge 282 of the outer rim 280 of the seat 210 covering a side wall of the outer rim 280 of the seat 210. According to some embodiments, the edge portion 223 of the inner liner 221 is configured to direct at least a portion of toilet plume leaving the toilet bowl 295 and entering air outside of the toilet bowl 295 in a downward direction (for example, as shown by air vector fields 102 in FIG. 1). According to some embodiments, the outer rim 280 of the seat 210 is configured to direct at least a portion of toilet plume leaving the toilet bowl 295 and entering air outside of the toilet bowl 295 in a downward direction (for example, as shown by air vector fields 102 in FIG. 1).

In some embodiments, the lid may be hollow and an inner liner and an outer liner of the lid form a hollow portion of the lid. For example, the inner liner 221 and the outer liner 226 may be joined to form a hollow lid structure of the lid 220. FIG. 2D shows an example of a hollow lid structure of lid 220 comprising a hollow portion 236. The inner liner 221 and the outer liner 226 may be spaced a distance apart that varies with the shaped surface portion 222 and the core portion 224. According to some embodiments, the outer liner 226 of the lid 220 is configured to direct at least a portion of toilet plume leaving the toilet bowl 295 and entering air outside of the toilet bowl 295 in a downward direction (for example, as shown by air vector fields 102 in FIG. 1B).

Figure 3A:
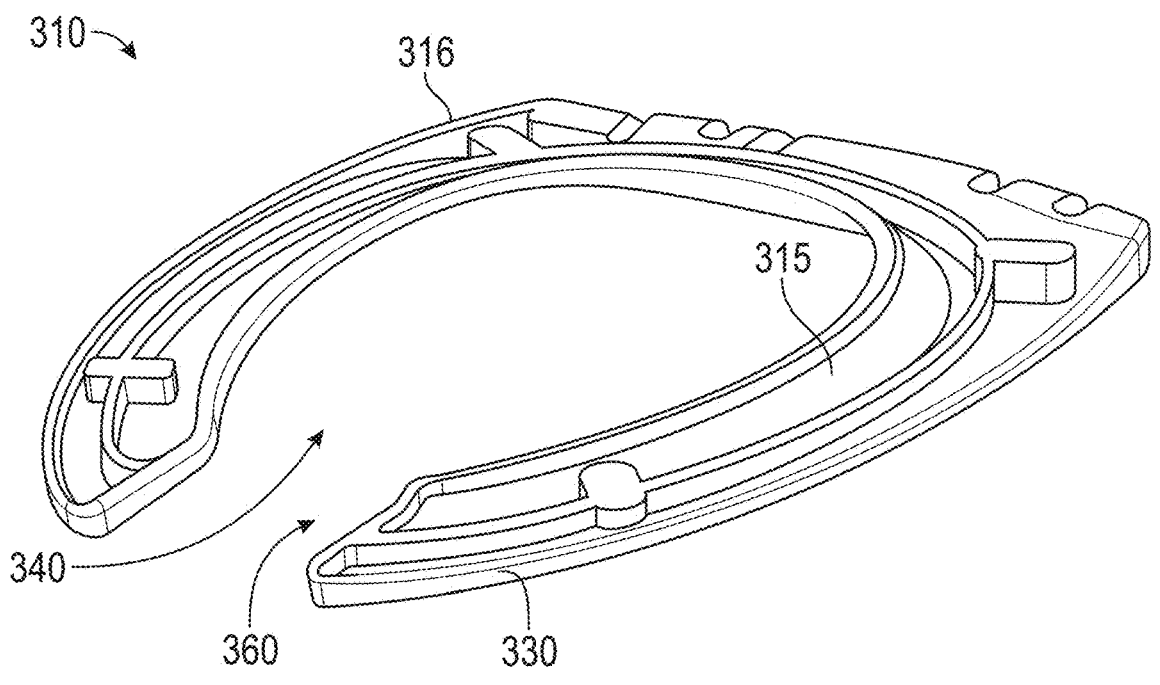
FIG. 3A shows an example of a seat of a seat assembly, according to some embodiments.
Figure 3B:
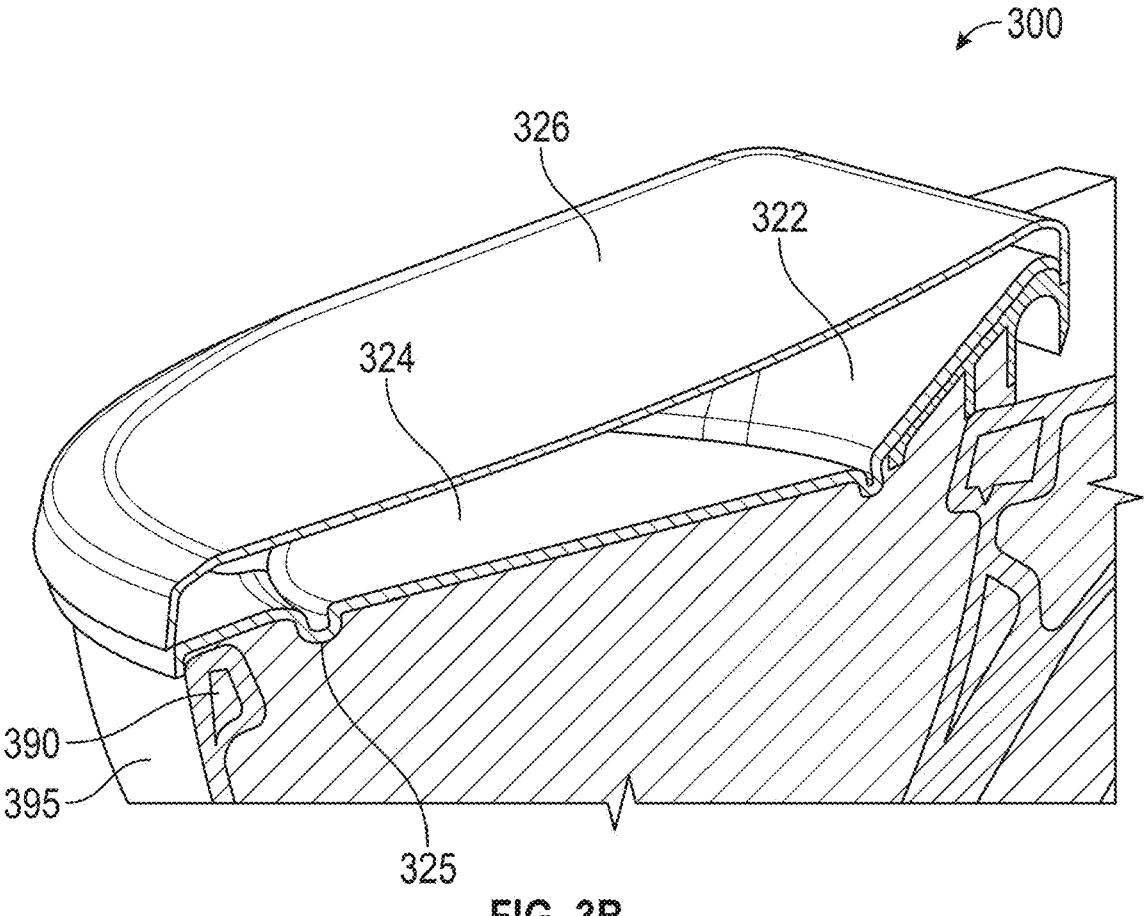
FIGS. 3B and 3C show cross-sectional views of exemplary seat assemblies, according to some embodiments.
Figure 3C:
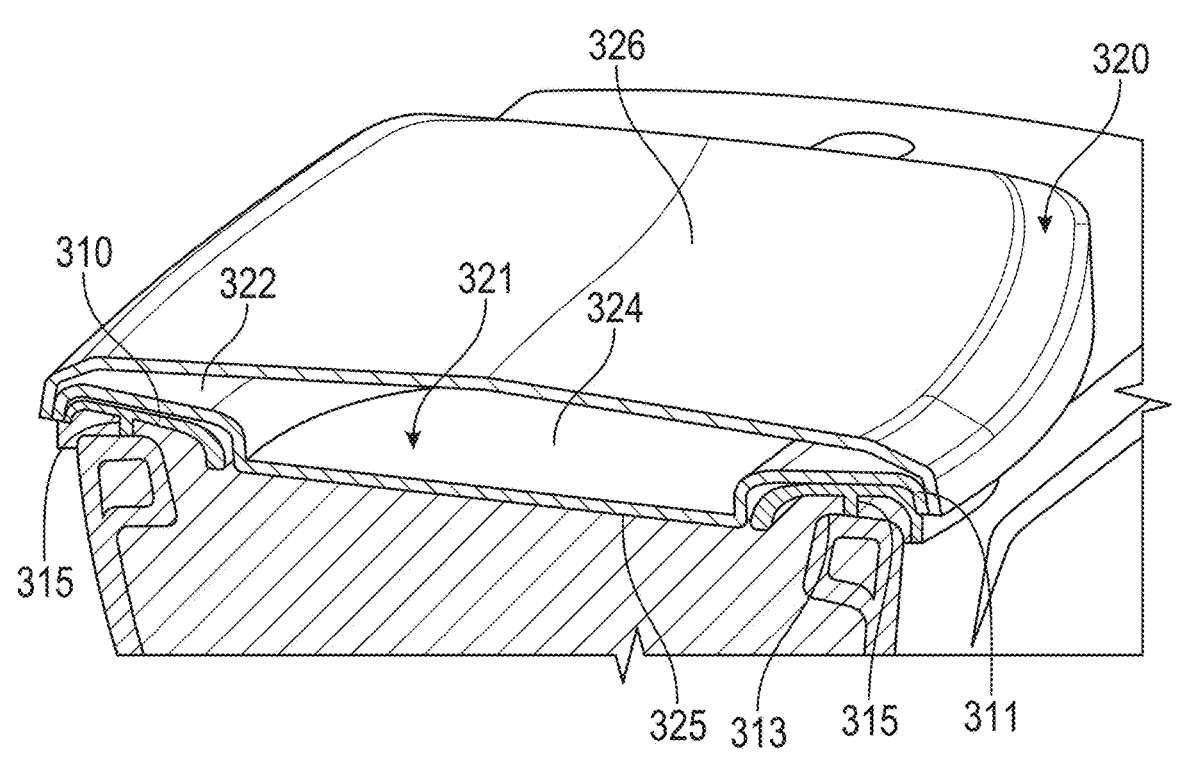

FIG. 3A shows a bottom side of an exemplary seat of a seat assembly, according to some embodiments. The seat 310 includes a central rib 315 on a bottom side 316 of the seat 310 that faces an upper rim 390 of a toilet 395 (toilet shown in FIGS. 3B and 3C). The seat 310 includes a central opening 340 and a front opening 360. A contoured upper seat surface 330 of the seat 310 is around the central opening 340 of the seat 310. FIGS. 3B and 3C show cross-sectional views of exemplary seat assemblies, according to some embodiments. FIGS. 3B and 3C show a seat assembly 300 that includes a seat 310 and a lid 320 configured to cover the seat 310. According to some embodiments, the lid 320 may include an inner liner 321 and an outer liner 326. The inner liner 321 may be configured to cover the seat 310, the central opening 340 of the seat 310, and the front opening 260 of the seat 310. The outer liner 326 may be configured to cover the inner liner 321. The inner liner may include a shaped surface portion 322 and a core portion 324 joined to the shaped surface portion 322 at a rim 325. The lid 320 is similar to lid 220, and thus for brevity, reader is referred to the above description of the lid 220 for the lid features of 320. The lid-to-seat clearance 311 and the seat-to-bowl clearance 313 regarding the seat 310 is similar to lid-to-seat clearance 211 and the seat-to-bowl clearance 213 regarding the seat 210. Thus, for brevity, the reader is referred to the above description regarding clearance features of seat 210 for clearance features of seat 310.

Figure 4A:
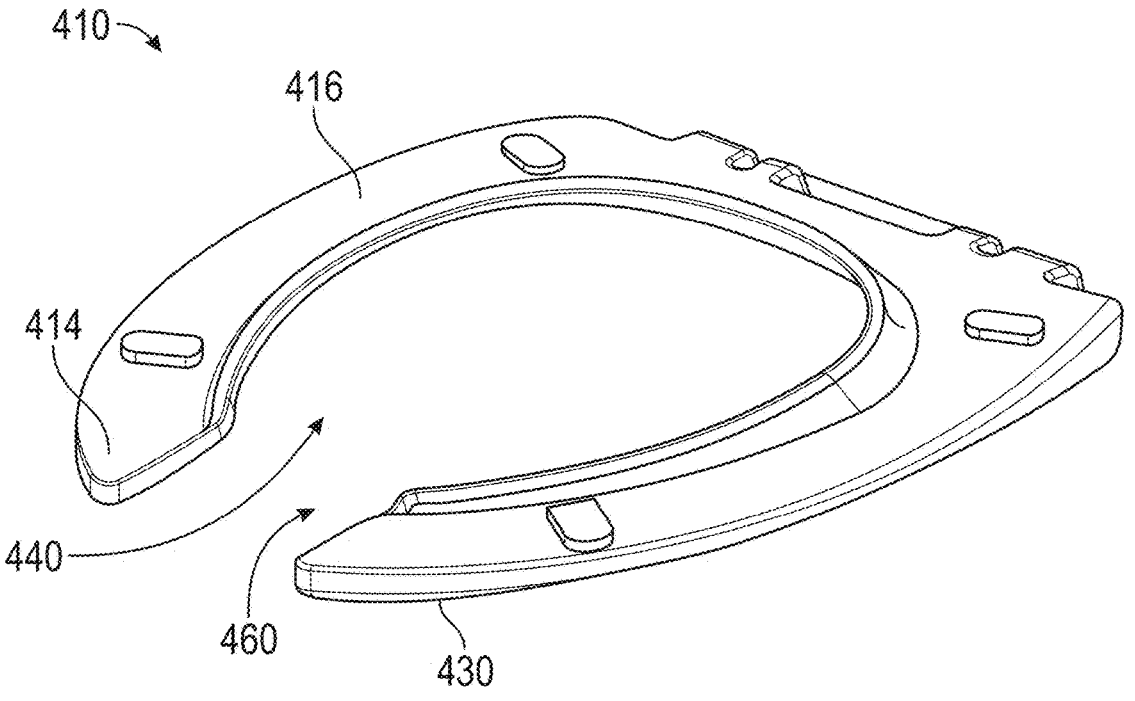
FIG. 4A shows an example of a seat of a seat assembly, according to some embodiments.
Figure 4B:
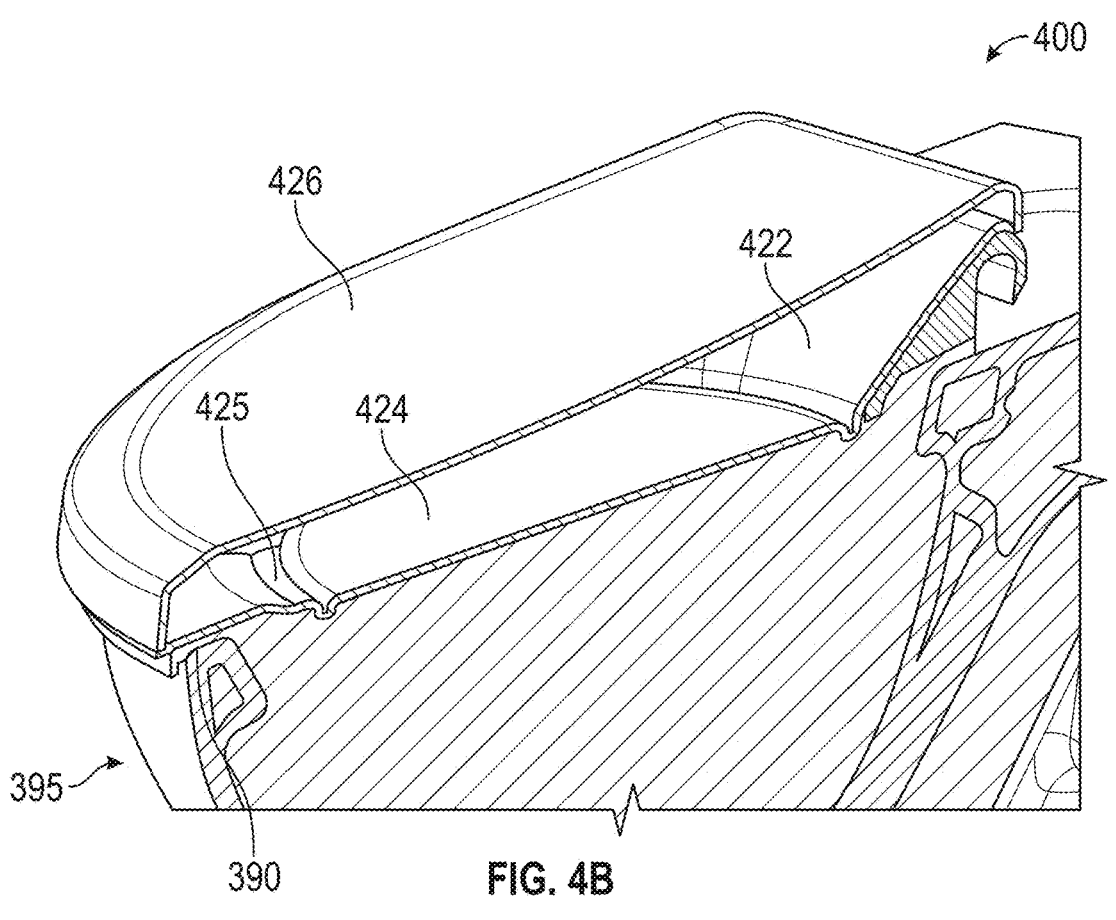
FIGS. 4B and 4C show cross-sectional views of exemplary seat assemblies, according to some embodiments.
Figure 4C:
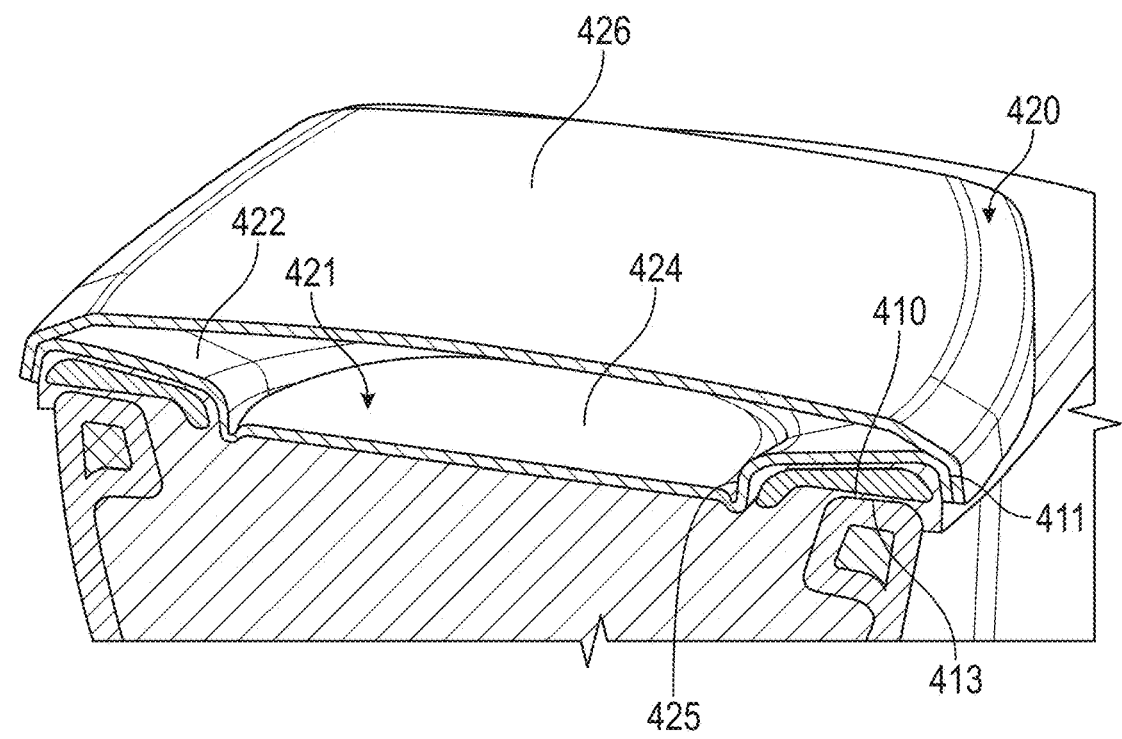

FIG. 4A shows a bottom side of an exemplary seat of a seat assembly, according to some embodiments. The seat 410 includes a bottom side 416 of the seat 410 that faces an upper rim 490 of a toilet 495 (toilet shown in FIGS. 4B and 4C) and an upper contoured seat surface 440 for a user to sit. The seat 410 includes a solid seat that includes a wedge portion 414. The wedge portion 414 makes seat 410 thicker than seat 210 and seat 310. The seat 410 includes a central opening 440 and a front opening 460. The contoured upper seat surface 430 of the seat 410 is around the central opening 440 of the seat 410. FIGS. 4B and 4C show cross-sectional views of exemplary seat assemblies, according to some embodiments. FIGS. 4B and 4C show a seat assembly 400 includes a seat 410 and a lid 420 configured to cover the seat 410. According to some embodiments, the lid 420 may include an inner liner 421 and an outer liner 426. The inner liner 421 may be configured to cover the seat 410, the central opening 440 of the seat 410, and the front opening 460 of the seat 410. The outer liner 426 may be configured to cover the inner liner 421. The inner liner may include a shaped surface portion 422 and a core portion 424 joined to the shaped surface portion 422 at a rim 425. The lid 420 is similar to lid 220, and thus for brevity, reader is referred to the above description of the lid 220 for the lid features of 420. The lid-to-seat clearance 411 and the seat-to-bowl clearance 413 regarding the seat 410 is similar to lid-to-seat clearance 211 and the seat-to-bowl clearance 213 regarding the seat 210. Thus, for brevity, the reader is referred to the above description regarding clearance features of seat 210 for clearance features of seat 410. According to some embodiments, the seat 210, 310, 410 may be compatible for one or more of residential and commercial toilets.

Figure 5:
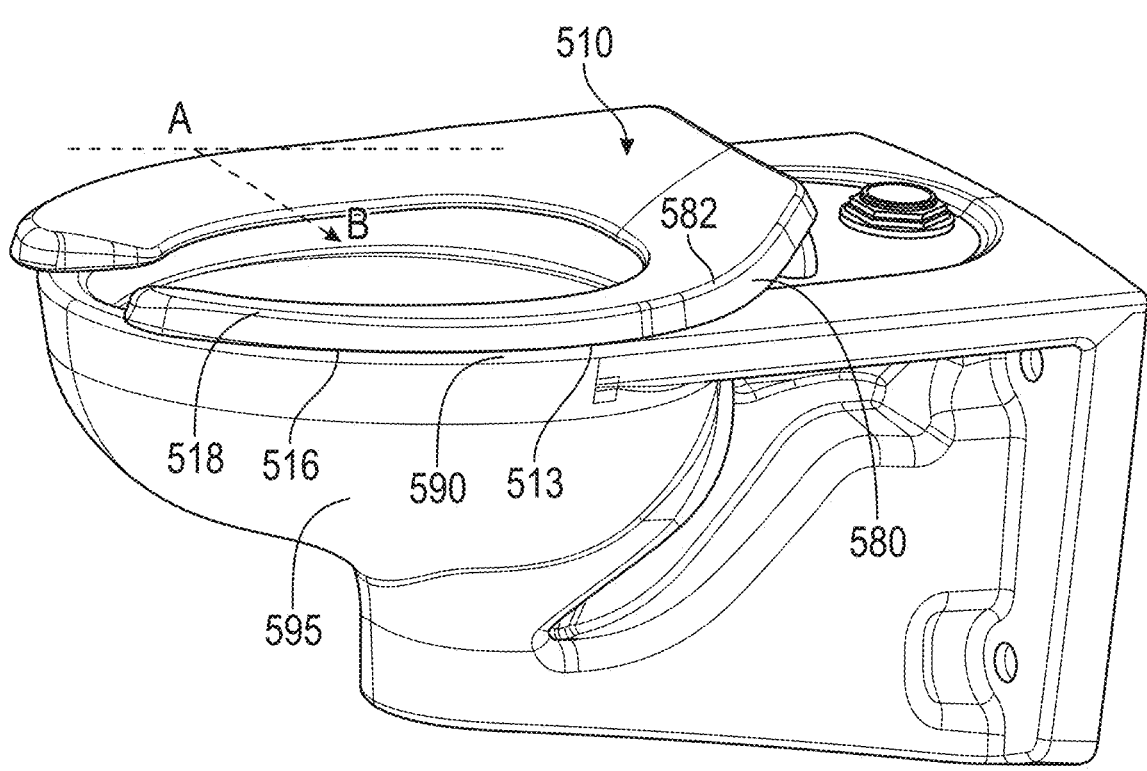
FIG. 5 shows an example of the seat in a closed seat position over a toilet bowl, according to some embodiments.

FIG. 5 shows an example of the seat in a closed seat position over a toilet bowl, according to some embodiments. In the example of FIG. 5, the lid of the seat assembly 500 is not shown. As shown in the example of FIG. 5, the seat 510 may include a sidewall 518 that extends from an upper edge 582 of the outer rim 580 to a bottom surface 516 of the seat 510. The bottom surface 516 is covered to contact an upper rim 590 of a toilet bowl 595. In the closed seat position, the seat 510 and the upper rim 590 of the toilet bowl 595 may be spaced by a seat-bowl clearance 513.

During flushing, when water enters the toilet bowl from a toilet tank toilet plume may be pushed out of the toilet bowl into the user area. During flushing, when water exits the toilet bowl through toilet plumbing (such as toilet trapway), air from the user area may be sucked into the toilet bowl. The amount of toilet plume during flushing may be dependent on an amount of air entering and leaving the toilet bowl and associated level of turbulent flow. Increased turbulent flow may result from one or more of air entering the toilet bowl during flushing and air entering the user area. The seat-to-bowl clearance 513 regarding the seat 510 is similar to the seat-to-bowl clearance 213 regarding the seat 210. Thus, for brevity, the reader is referred to the above description regarding clearance features of seat 210 for clearance features of seat 510. According to some embodiments, the seat 510 may be compatible for one or more of residential and commercial toilets.

According to some embodiments, the seat assembly may include one or more sensors configured to detect a presence of a user and an action of the user. The one or more sensors may include one or more of a motion sensor, a proximity sensor, and a pressure sensor. For example, one or more of a motion sensor and a proximity sensor may be configured to detect when a user approaches the seat assembly and when a user moves away from the seat assembly. The one or more of a motion sensor and a proximity sensor may be configured to detect an action of a user for example, the user may move to gesture that the user intends to use the toilet with the seat in an open seat position. One or more of a motion sensor, a proximity sensor, and pressure sensor may be configured to detect when a user sits on the seat of the toilet assembly or is positioned over the seat of the toilet seat assembly. Based on detection through the one or more sensors, a controller may be configured to allow automatic opening and closing of one or more of a seat and a lid of a seat assembly. In some embodiments, the controller may be configured to automatically flush the toilet when the lid is in a closed lid position. In this way, a user may use the toilet without having to manually open or close the lid or manually flush the toilet. Additionally, this allows the toilet to be flushed when the lid is in a closed lid position, thus reducing toilet plume entering the user area of the toilet.

According to some embodiments, the one or more sensors may be placed on the seat assembly at one or more locations on the seat assembly. According to some embodiments, the one or more sensors may be mounted onto one or more of a lid and a seat of the seat assembly. The one or more sensors may be positioned to sense a user or an action of a user. According to some embodiments, a seat assembly may include one or more first sensors mounted on an outer liner of a lid and include one or more second sensors mounted on an inner liner of the lid. In this, the one or more first sensors may be configured sense presence of a user and an action of the user when the lid is in a closed lid position and the one or more second sensors may be configured to sense presence of a user and an action of the user when the lid is in an open lid position.

Figure 6B:
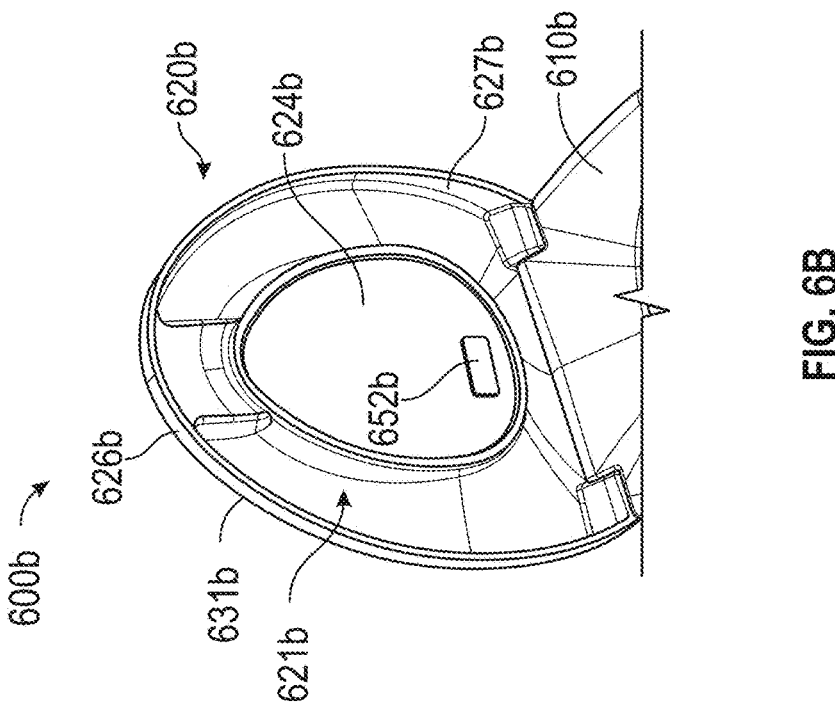
FIGS. 6A and 6B show example locations where the one or more sensors may be positioned on the seat assembly, according to some embodiments.
Figure 6A:
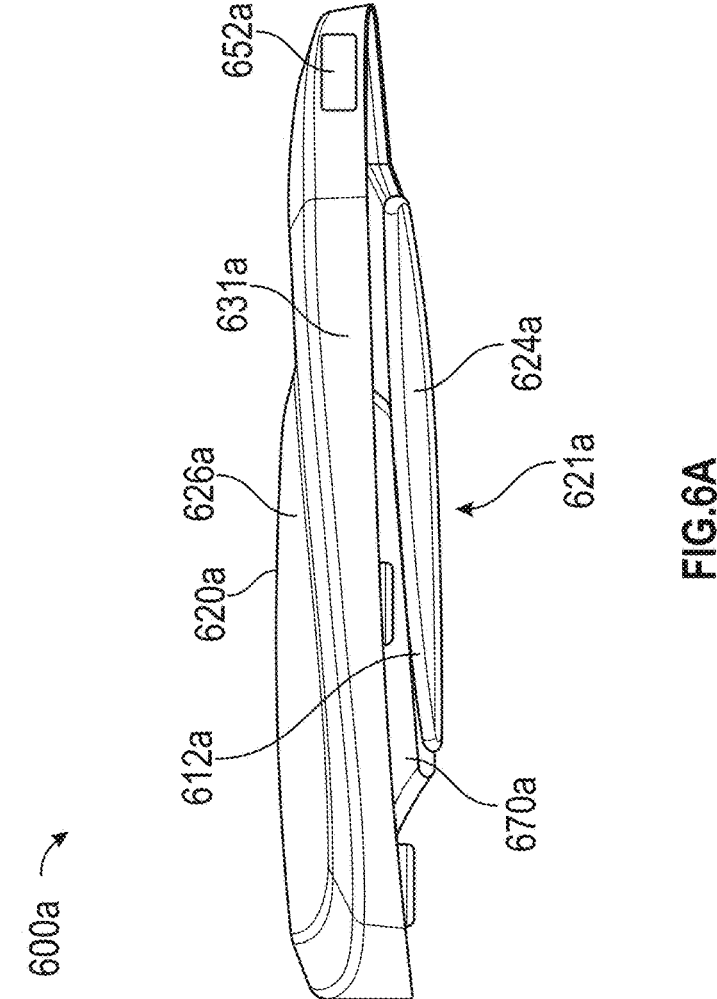

FIGS. 6A and 6B show example locations where the one or more sensors may be positioned on the seat assembly, according to some embodiments. The seat assemblies shown in FIGS. 6A and 6B may include a lid such as lid 220, 320, 420 and a seat such as seat 210, 310, 410, or 510. According to some embodiments, a seat assembly may include one or more sensors positioned as shown in FIG. 6A, FIG. 6B, or a combination thereof. FIG. 6A shows a seat assembly 600*a* that includes a seat 610*a* in a closed seat position (toilet not shown) and a lid 620*a* in a closed lid position. The lid 620*a* includes an outer liner 626*a* and an inner liner 621*a*. The outer liner 626*a* includes an edge portion 631*a* that is configured to extend over a sidewall (not shown in FIG. 6A, but 627*b* in FIG. 6B) of the inner liner 621*a*. In the example of FIG. 6A, one or more sensors 252*a* may be mounted on the edge portion 631*a* of the outer liner 626*a*. In the example of FIG. 6A, a core portion 624*a* of the inner liner 621*a* of the lid 620*a* extends past an inner rim 670*a* of the seat 610*a*.

FIG. 6B shows a seat assembly 600*b* that includes a seat 610*b* in a closed seat position (toilet not shown) and a lid 620*b* in an open lid position. The lid 620*b* includes an outer liner 626*b* and an inner liner 621*b*. The outer liner 626*b* includes an edge portion 631*b* that is configured to extend over a sidewall 627*b* of the inner liner 621*b*. In the example of FIG. 6B, one or more sensors 652*b* may be mounted on a core portion 624*b* of the inner liner 621*b*.

Figure 7A:
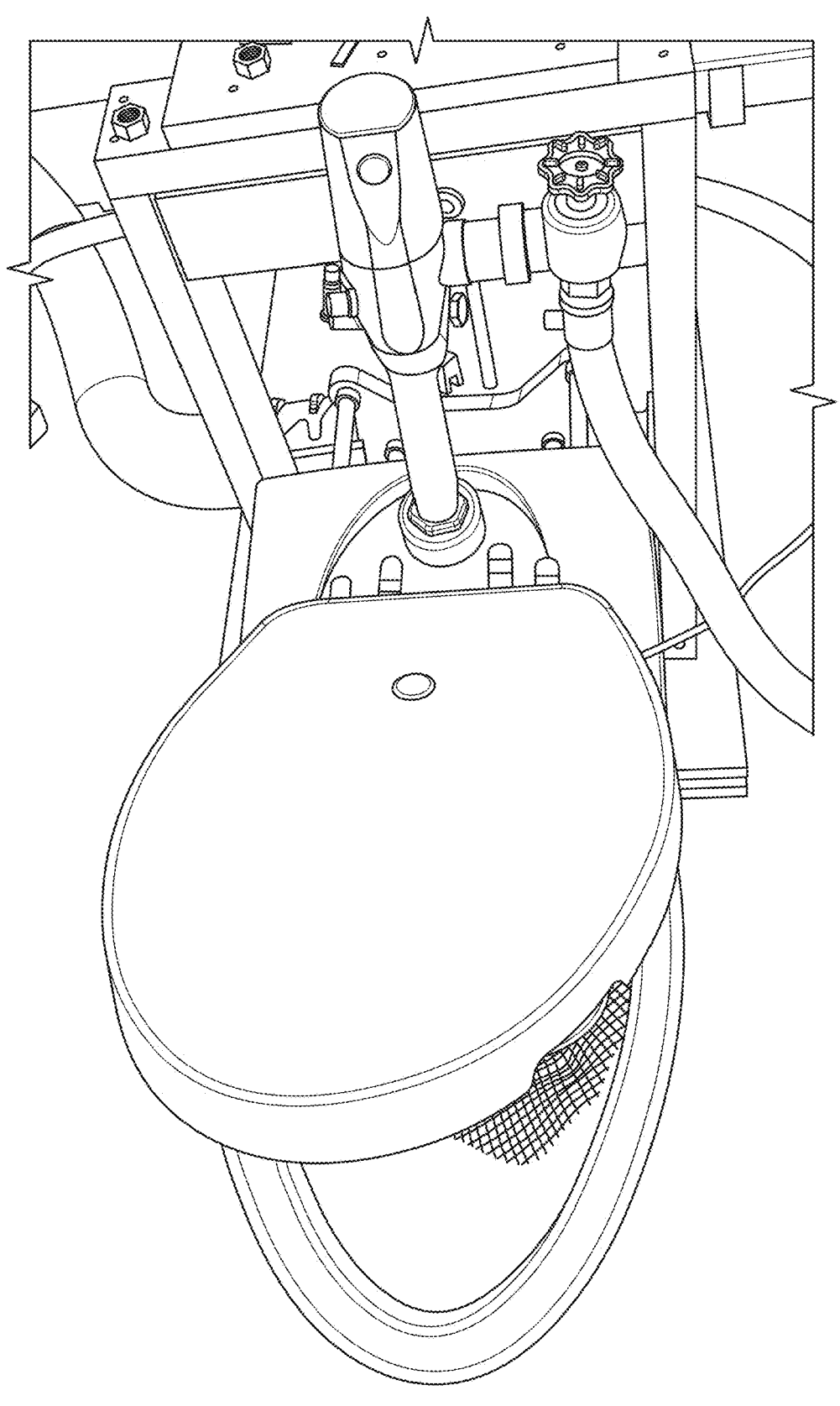
FIGS. 7A and 7B show sensor positions in a toilet assembly with a partially closed toilet lid and sensor positions in a toilet assembly with a fully open toilet lid, respectively, according to some embodiments.
Figure 7B:
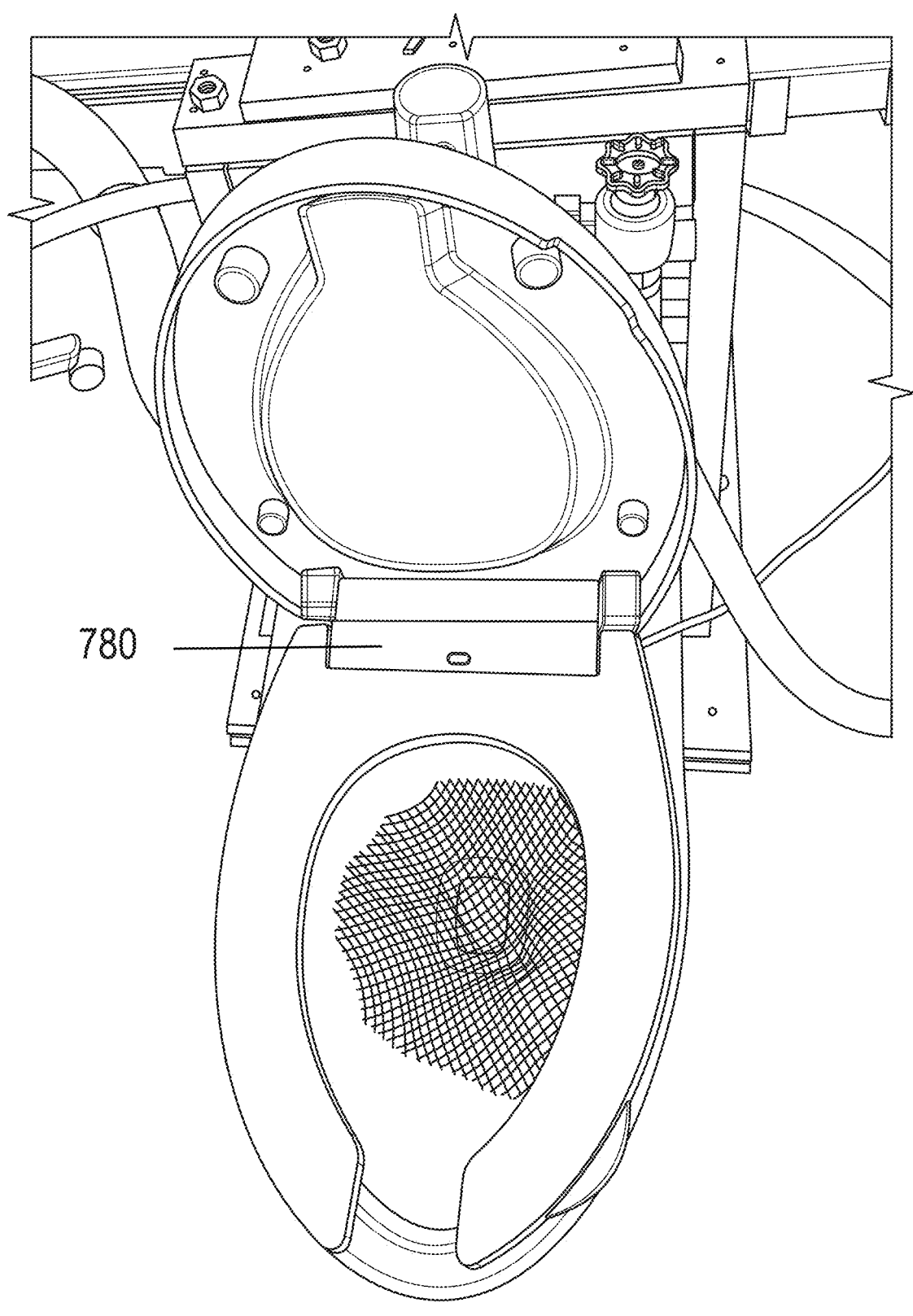

FIG. 7A shows sensor positions in a toilet assembly with a partially closed toilet lid, and FIG. 7B shows sensor positions in a toilet assembly with a fully open toilet lid. As shown in both FIGS. 7A and 7B, an IR sensor is positioned within the flush valve. A flush valve IR sensor can be triggered in a typical fashion by a user to initiate an automatic flush cycle. This sensor can also be used to detect when the toilet lid is raised (such that the toilet assembly does not initiate a flush cycle when the toilet lid is raised) and when the toilet lid is lowered (such that the toilet assembly may initiate a flush cycle). In some embodiments, a flush cycle is prevented from initiating when the lid of the toilet assembly is in a fully open position. In some embodiments, a flush cycle is prevented from initiating when the lid of the toilet assembly is in a partially open position.

Also included in toilet assemblies provided herein is a microwave sensor positioned at a base of a toilet seat, for example in a housing coupled to a seat, lid, and bowl. The microwave sensor detects when a user is approaching or present, and instructs the toilet lid to open such that the user may use the toilet.

Finally, a second IR sensor may be located at a base of the toilet seat in a position that allows the IR sensor to detect the presence of a user. When the toilet lid is closed, this IR sensor is covered by the toilet seat. However, when the toilet seat is fully open, as shown in FIG. 7B, the IR sensor is exposed such that it can detect the presence of a user as the user is using the toilet assembly, for example. As shown, the IR sensor is provided within a housing 780 at the pivoting base of the toilet seat.

Figure 8A:
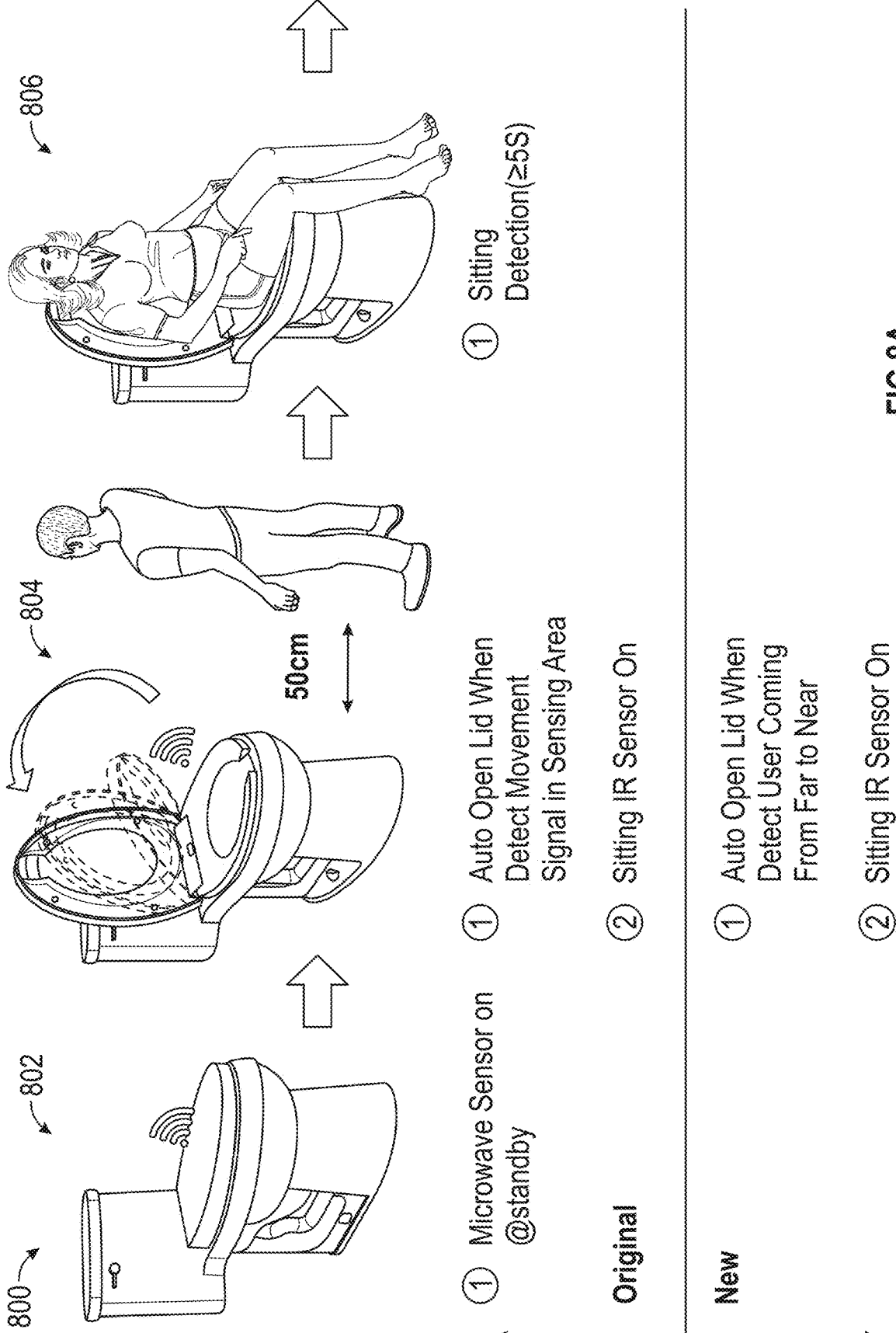
FIGS. 8A and 8B show methods of operation of a toilet assembly for a sitting user and a standing user, respectively, according to some embodiments.
Figure 8A:
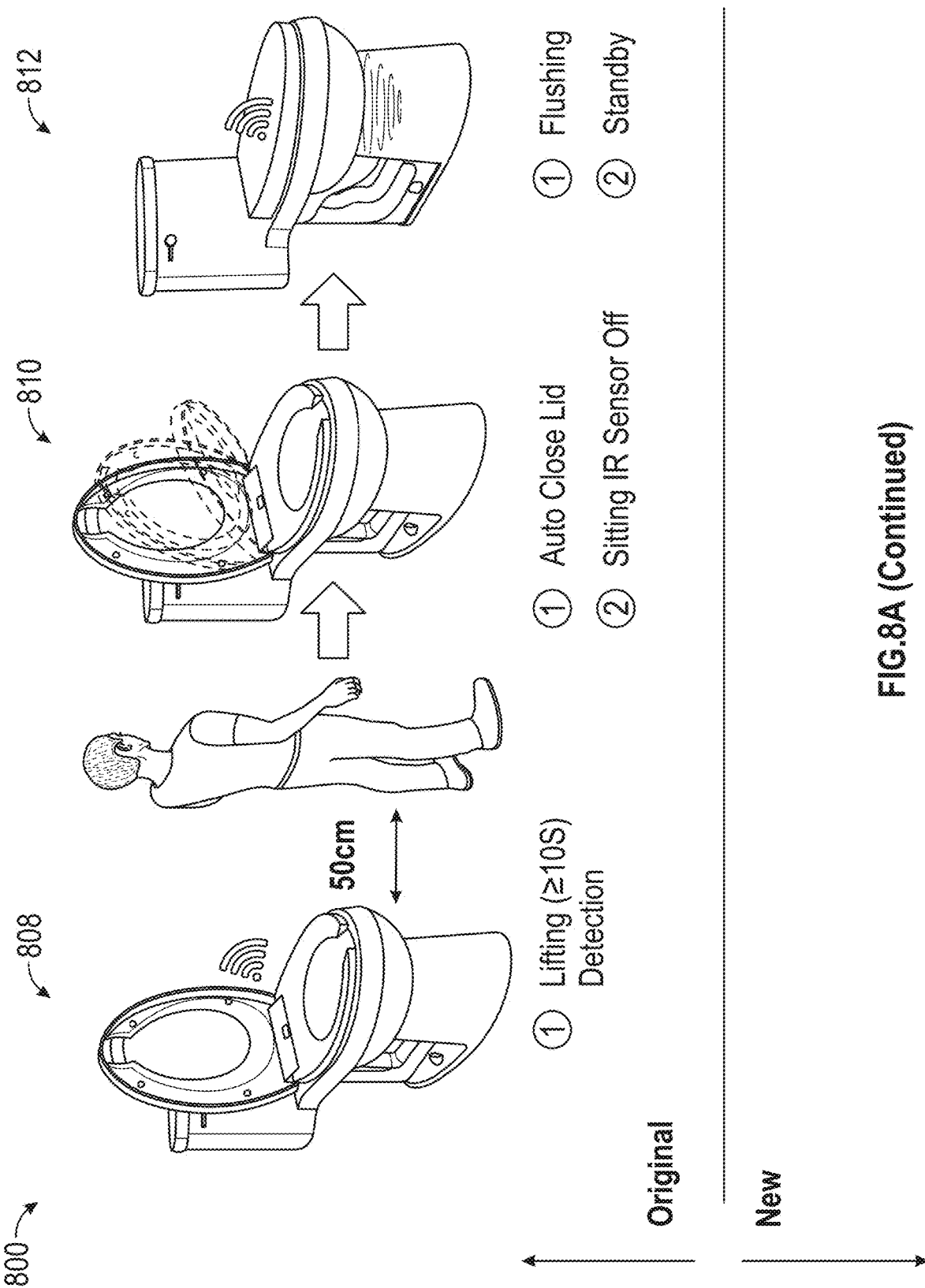

FIG. 8A shows a method 800 of operation of a commercial toilet assembly for a sitting user, according to some embodiments.

Method 800 can utilize microwave sensor and one or more infrared (IR) sensors. At step 802, a microwave sensor may be on standby (e.g., when the toilet assembly is at rest and no user is within proximity). When the microwave sensor detects movement (i.e., from a user), it can instruct the toilet lid to open. At step 804, the toilet lid opens and blocks (activates) a first IR sensor in the flush valve. In some embodiments, a microwave sensor may be configured to detect a user approaching the toilet assembly (i.e., coming to the toilet assembly from a position far from the toilet assembly, to a position close to the toilet assembly). If the user sits to use the toilet assembly, a seat IR sensor remains "on". At step 806, as the user uses the toilet assembly in a sitting position, the IR sensor continues to detect the presence of the user.

At step 808, the IR sensor detects when a user moves from a sitting position on the toilet assembly to a standing position and leaves the proximity of the toilet assembly. The IR sensor may then generate a signal instructing the toilet lid to close at step 810. At this point, the seat IR sensor can shut off. Finally, at step 812, closing of the lid un-blocks the first flush valve IR sensor. The toilet assembly may automatically flush upon the first IR sensor being un-blocked. The microwave sensor may remain in a standby mode. In some embodiments, the flush valve includes a timer that initiates a flush cycle after a certain amount of time once the toilet seat lid is fully closed.

Figure 8B:
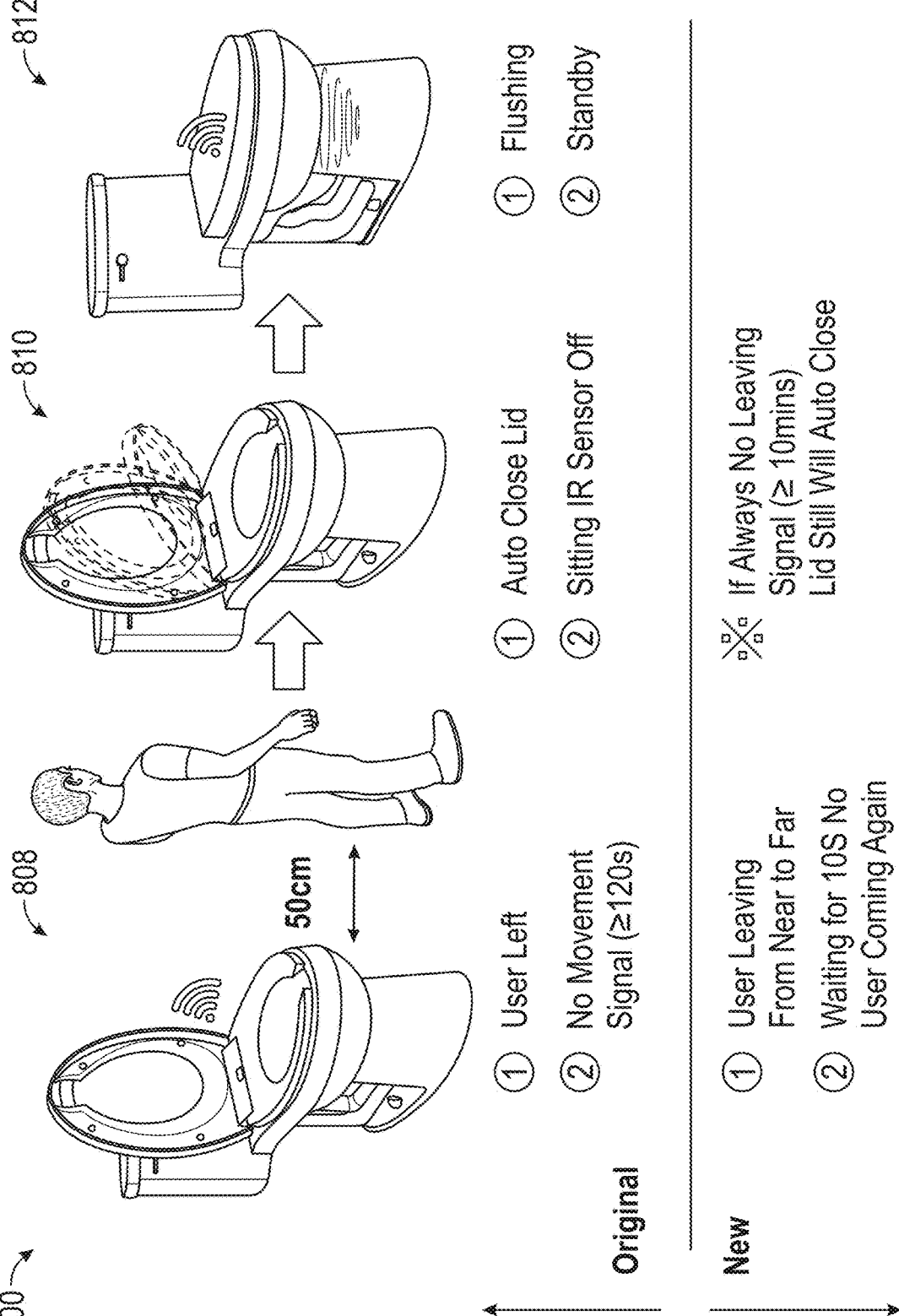

FIG. 8B shows a method 800 of operation of a commercial toilet assembly for a standing user, according to some embodiments.

Method 800 can utilize microwave sensor and one or more infrared (IR) sensors. At step 802, an microwave sensor may be on standby (e.g., when the toilet assembly is at rest and no user is within proximity). When the microwave sensor detects movement (i.e., from a user), it can instruct the toilet lid to open. At step 804, the toilet lid opens and blocks (activates) the first IR sensor in the flush valve. In some embodiments, a user may manually raise and lower the toilet seat to use the toilet assembly in a standing position. In some embodiments, the toilet assembly may be configured to determine that the user wishes to use the toilet assembly in a standing position, and may automatically raise the toilet seat for the user (and lower the toilet seat when the toilet assembly detects that the user is done using the toilet assembly.

In some embodiments, the microwave sensor may be configured to detect a user approaching the toilet assembly (i.e., coming to the toilet assembly from a position far from the toilet assembly, to a position close to the toilet assembly). If the user sits to use the toilet assembly, the second IR sensor remains "on." At step 806, if the user uses the toilet assembly in a standing position, the second IR sensor continues to detect the presence of the user.

At step 808, the second IR sensor detects when a user leaves the proximity of the toilet assembly. If no movement is detected for a predetermined amount of time (e.g., more than 120 seconds), the lid may be instructed to close. In some embodiments, the second IR sensor detects when a user leaves the proximity of the toilet assembly (i.e., moving from a position close to the toilet assembly, to a position further away from the toilet assembly), and can generate a signal after a predetermined amount of time has passed without a new user approaching the toilet assembly (e.g., 10 seconds) to instruct the toilet lid to close at step 810. At this point, the IR sensor can shut off. In some embodiments, if a predetermined amount of time has passed without a signal (e.g., 10 minutes), the lid may still automatically close after said predetermined amount of time. Finally, at step 812, the toilet assembly may automatically flush, and the microwave sensor may remain in a standby mode. In some embodiments, the flush valve includes a timer that initiates a flush cycle after a certain amount of time once the toilet seat is fully closed.

In some embodiments, the system of FIGS. 8A and 8B may also be implemented into a residential toilet assembly. A residential toilet assembly may not include a flush valve, but a flush cycle may otherwise be manually or automatically instructed. For example, a lever or a touchless sensor may be used to manually/automatically initiate a flush cycle. A touchless sensor may be located on the toilet assembly (e.g., on the water tank and/or behind the toilet bowl). A touchless sensor may also be located separate from the toilet assembly. For example, a touchless sensor may be located on a "puck" or removably mountable device that can be mounted and/or moved to different locations to suit a user's needs. In some embodiments, a "puck" may be mounted on a bathroom wall, on the side of the water tank of a toilet assembly, on a sink, etc.

In some embodiments, a commercial sensor system may be retro-fit to modify an existing commercial toilet assembly having an IR sensor in a flush valve. In such an embodiment, the IR sensor in the flush valve would not be electrically connected with the controller, a second IR sensor configured to detect a user's presence, and/or the microwave sensor at a toilet base. However, the IR sensor in the flush valve would still be able to appropriately initiate a flush cycle by detecting the presence/absence of the toilet lid. Specifically, the IR sensor in the flush valve would be blocked by the toilet lid when the toilet lid is up (and thus, the IR sensor will be able to detect the presence of the toilet lid and will not initiate a flush cycle). Similarly, once the toilet lid is lowered, the absence of the toilet lid blocking the IR sensor in the flush valve will trigger the flush valve to initiate a flush cycle.

Figure 9:
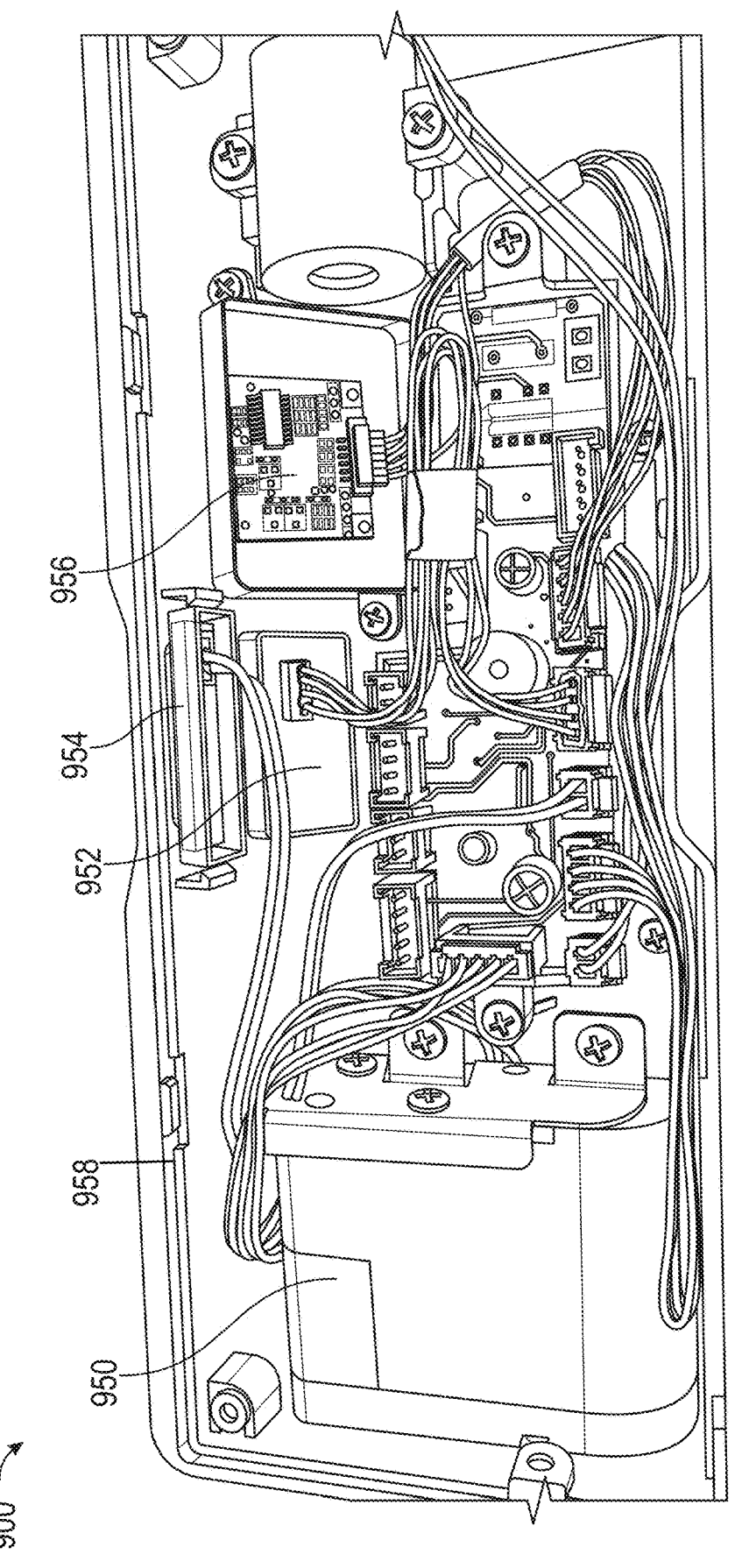
FIG. 9 shows an image of the circuitry and location of sensors of a toilet assembly, according to some embodiments.

FIG. 9 shows an image of the circuitry 900 of a toilet assembly according to some embodiments provided herein. Servomotor 950 controls the raising and lowering of the toilet seat lid. Infrared sensor 954 detects the presence of a user using the toilet assembly, and microwave sensor 952 detects the presence of a user in approaching, or in general proximity to the toilet assembly. Controller/microcontroller 956 controls may be in electrical communication with one or more of servomotor 950, infrared sensor 954, and/or microwave sensor 952. Each of the servomotor 950, infrared sensor 954, microwave sensor 952, and controller 956 are provided within a housing 958. The housing 928 may be located at the pivoting base of the toilet lid.

Figure 10:
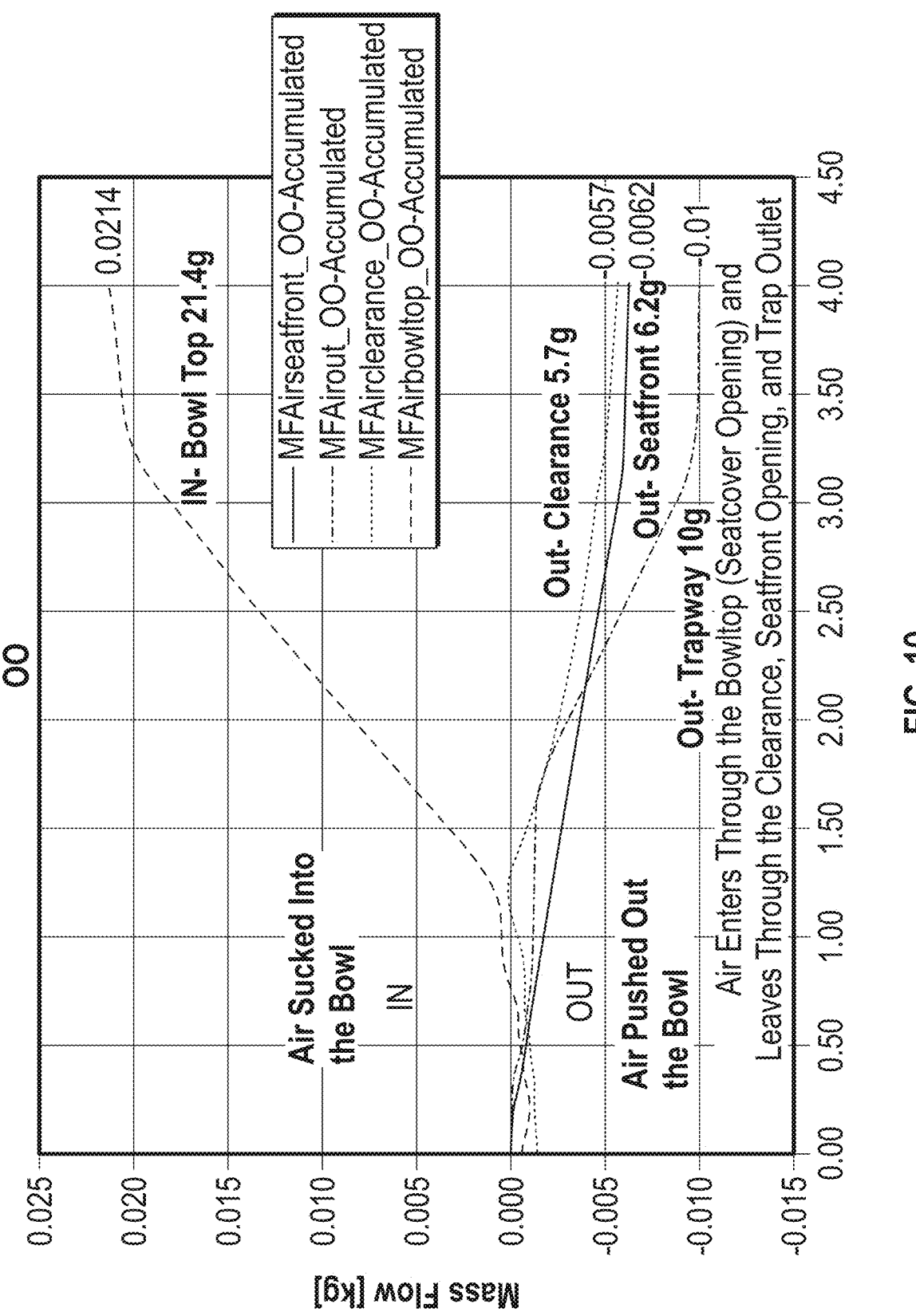
FIG. 10 shows mass flow data through a seat assembly when a lid of the seat assembly is in an open lid position, according to some embodiments.
Figure 11:
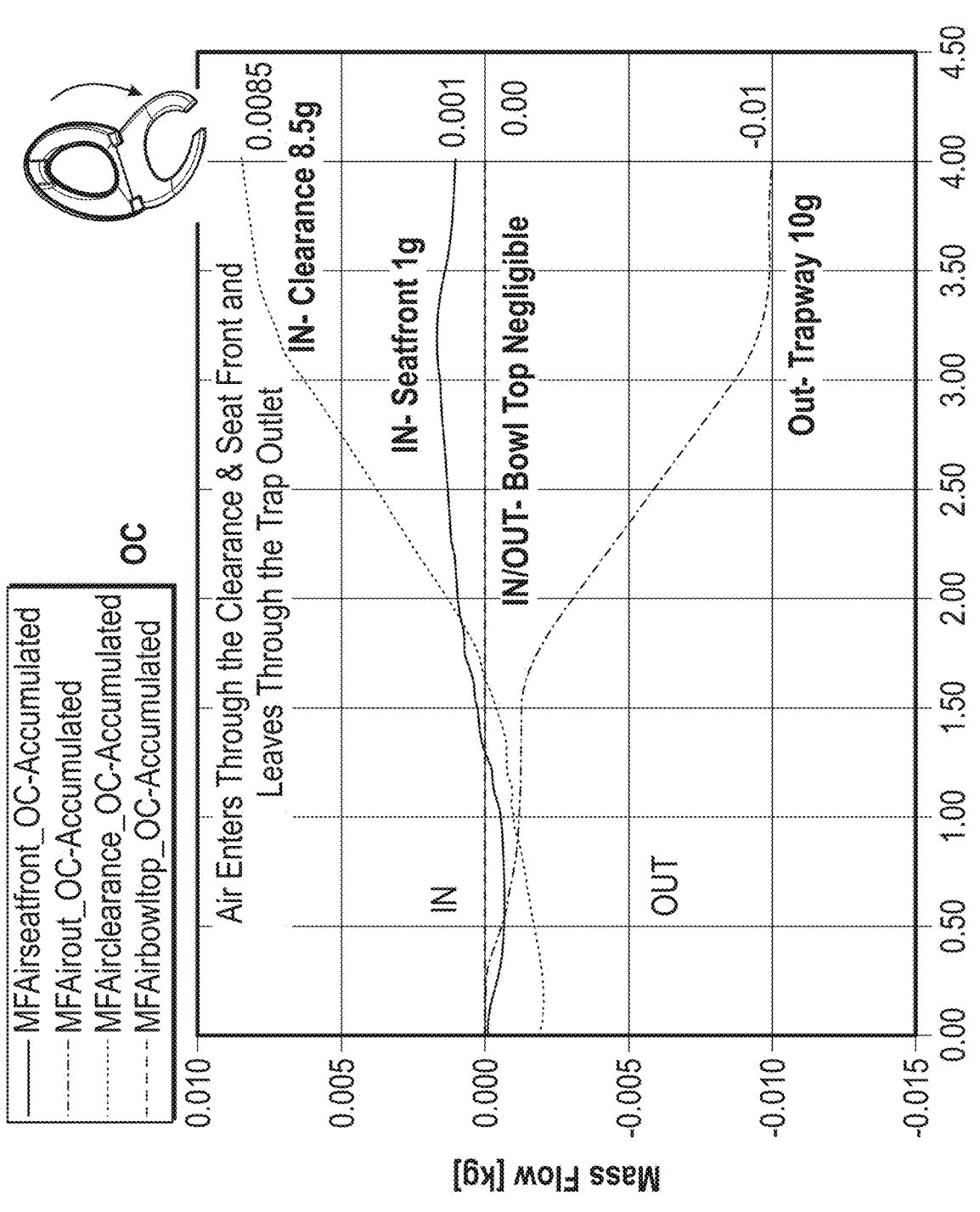
FIG. 11 shows mass flow data through a seat assembly when a lid of the seat assembly is in a closed lid position, according to some embodiments.
Figure 12:
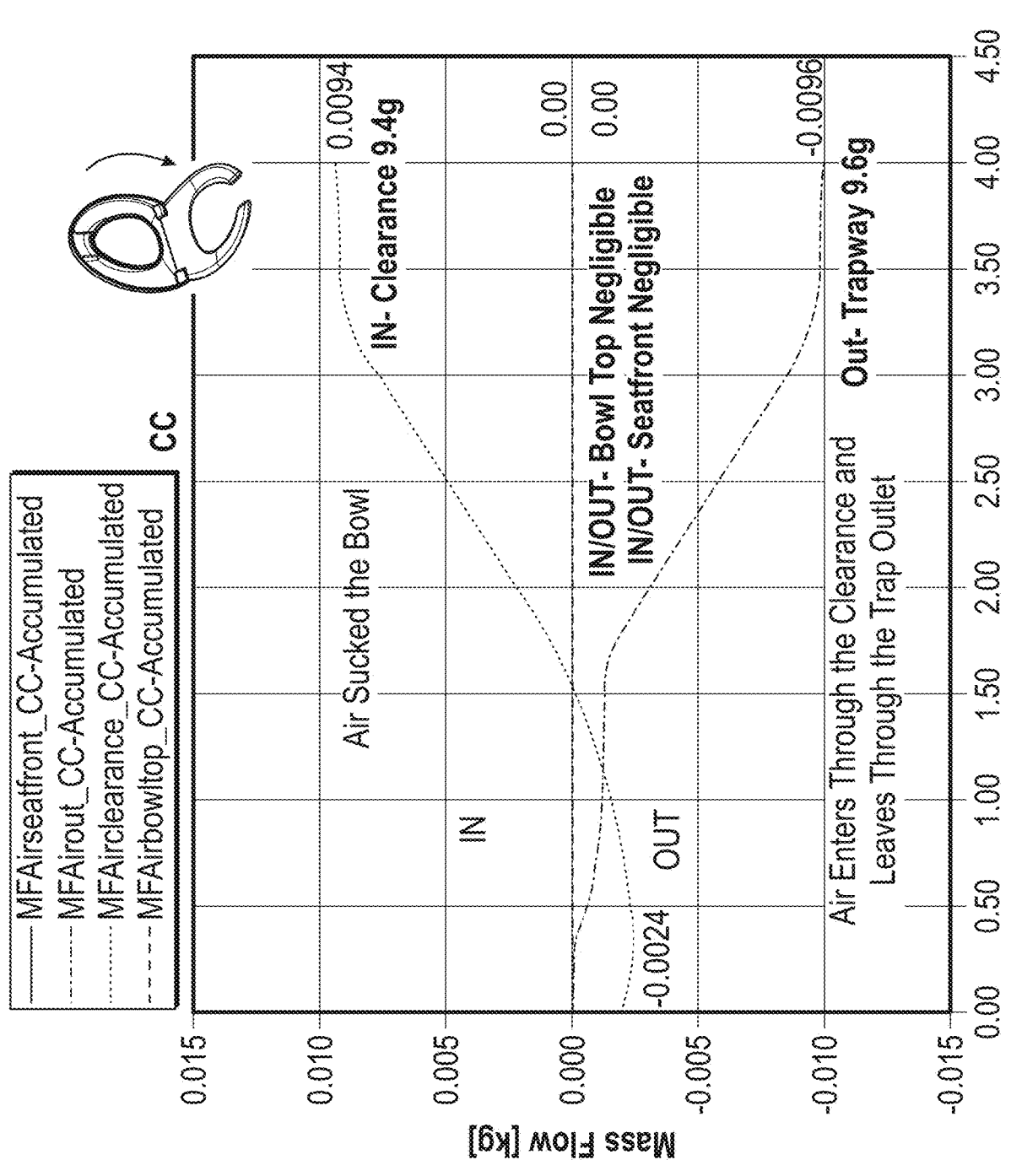
FIG. 12 shows mass flow data through a seat assembly when a lid of the seat assembly is in a closed lid position, according to some embodiments.

FIGS. 10-12 show examples of mass flow in and out of a toilet bowl through a seat assembly, according to some embodiments. The examples of mass flow data shown in FIGS. 10-12 may be simulated data based on the seat assembly and standard toilet flushing specifications associated with a toilet that flushes from about 0.8 gallons to about 1.6 gallons per flush. In FIGS. 10-13, negative mass flow values are indicative of mass flow into the toilet bowl and positive values are indicative of mass flow from the toilet bowl into a user area of the toilet (such as user area 130). In FIGS. 10-13, the following acronyms are used: MF (mass flow rate), OO (open seatfront, open lid), OC (open seatfront, closed lid), and CC (closed seatfront, closed lid). In some embodiments, the seat may include an open seatfront (such as in the OC configuration). FIGS. 2-4 show examples of seats with an open seatfront—that is, the seat includes a seatfront opening such as front opening 260, 360, 460. In some embodiments, the seat may include a closed seatfront (such as in the CC configuration)—that is, an inner rim of the seat extends completely around a central opening of the seat, and thus the seat does not have a front opening.

In the example of FIG. 10, the mass flow data corresponds to having a lid of a seat assembly in an open lid position. FIG. 10 shows mass flow data through a seat assembly when a lid of the seat assembly is in an open lid position and a seat has an open seat front. Specifically, the example of FIG. 10 shows data associated with mass flow through a bowl top (such as central opening 240, 340, 440), through a clearance (such as seat-to-bowl clearance 213, 313, 413, 513), through a seatfront opening (such as front opening 260, 360, 460), and through toilet plumbing (such as a trapway outlet of a toilet). As shown in the example of FIG. 10, air flow enters the toilet bowl through the bowl top, leaves the toilet bowl into a user area of the toilet through the clearance and the seatfront, and leaves the toilet bowl into toilet plumbing through the toilet trapway. In the example of FIG. 10, an amount of air that enters the user area of a toilet such as user area 130 would be an addition of the air that flows out of the clearance and out of the seatfront opening.

In the example of FIG. 11, the mass flow data corresponds to having a lid in a closed lid position over a seat that has an open seatfront. The inset in FIG. 11 shows an example of a seat assembly with a seat that has an open seatfront and the arrow indicates that the data shown in FIG. 11 corresponds to the lid in a closed lid position over the seat. Specifically, the example of FIG. 11 shows data associated with mass flow through a bowl top (such as central opening 240, 340, 440), through a clearance (such as seat-to-bowl clearance 213, 313, 413, 513), the seatfront opening (such as front opening 260, 360, 460), and the trapway of a toilet. As shown in the example of FIG. 11, air flows enters the toilet bowl through the clearance and the seatfront opening and leaves the toilet bowl through the trapway. In the example of FIG. 11, there is negligible air flow in and out of the toilet bowl through the bowl top covered by the lid of the seat assembly. According to some embodiments, the lid in the closed position configured to cover a bowl top (such as central opening 240, 340, 440) and cover a seat that has an open seatfront (such as front opening 260, 360, 460) allows a reduction in air flow that is sucked into the toilet bowl compared to a seat assembly configuration, for example, as shown in FIG. 10. In some embodiments, the reduction in air flow shown in FIG. 11 compared to a seat assembly configuration as shown in FIG. 10 is at least about 20%, about 30%, or about 40%. In some embodiments, the reduction in air flow shown in FIG. 11 compared to a seat assembly configuration as shown in FIG. 10 is at most about 80%, about 70%, or about 60%. In some embodiments, the reduction in air flow shown in FIG. 11 compared to a seat assembly configuration as shown in FIG. 10 is about 20%-80%, about 30%-70%, or about 40%-60%. According to some embodiments, the reduction in air flow shown in FIG. 11 compared to a seat assembly configuration as shown in FIG. 10 may be configured to create less turbulence in bowl resulting in reduced plume exiting the bowl.

In the example of FIG. 12, the mass flow data corresponds to having a lid in a closed lid position. In contrast to FIG. 10 and FIG. 11, in this example, the seat is configured to have a closed seatfront—that is, the seat does not include a seat front opening. The inset in FIG. 12 shows an example of a seat assembly with a seat that has a closed seatfront and the arrow indicates that the data shown in FIG. 12 corresponds to the lid in a closed lid position over the seat. Specifically, the example of FIG. 12 shows data associated with mass flow through a bowl top (such as central opening 240, 340, 440), through a clearance (such as seat-to-bowl clearance 213, 313, 413, 513), and the trapway of a toilet. As shown in the example of FIG. 12, air flows enters the toilet bowl through the clearance and leaves the toilet bowl through the trapway. In the example of FIG. 12, there is negligible air flow in and out of the toilet bowl through the bowl top covered by the lid of the seat assembly and through the closed seat front seat covered by the lid of the seat assembly. Therefore, FIG. 12 shows that closing the lid configured to cover a bowl top (such as central opening 240, 340, 440) and a seat that has a closed seatfront allows a reduction in air flow from the toilet bowl into the user area compared to the example of FIG. 10. In some embodiments, the reduction in air flow shown in FIG. 12 compared to a seat assembly configuration as shown in FIG. 10 is at least about 20%, about 30%, or about 40%. In some embodiments, the reduction in air flow shown in FIG. 12 compared to a seat assembly configuration as shown in FIG. 10 is at most about 80%, about 70%, or about 60%. In some embodiments, the reduction in air flow shown in FIG. 12 compared to a seat assembly configuration as shown in FIG. 10 is about 20%-80%, about 30%-70%, or about 40%-60%. According to some embodiments, the reduction in air flow shown in FIG. 12 compared to a seat assembly configuration as shown in FIG. 10 may be configured to create less turbulence in bowl resulting in reduced plume exiting the bowl.

According to some embodiments, the reduction in air flow may be due to a reduction of mass of air flowing. In turn, the reduction in mass of air may reduce an amount of toilet plume that leaves the toilet bowl and enters air outside of the toilet bowl after flushing. According to some embodiments, the reduction of mass flowing may be a reduction of at least about 3 grams, about 6 grams, or about 9 grams of air. According to some embodiments, the reduction of mass flowing may be a reduction of at most about 18 grams, about 15 grams, or about 12 grams of air. According to some embodiments, the reduction of mass flowing may be a reduction of about 3-18 grams, about 6-15 grams, or about 9-12 grams of air.

FIG. 13 shows an example of mass flow data for different seat assemblies, according to some embodiments. The different seat assemblies may differ in a geometry of a seat of the seat assembly. The bottom inset of FIG. 13 shows three seats V1, V2, and V3 each having a different seat geometry. An example of seat V1, V2, and V3 are shown respectively in FIGS. 2D, 3A-3C, and 4A-4C. The mass flow data shown in FIG. 13 shows mass flow out of a first clearance of the toilet bowl when a lid is in its closed lid position (as shown in FIG. 9) compared to mass flow out of a second clearance when the lid is in the closed lid position. The first clearance and the second clearance are seat-to-bowl clearances between a bottom surface of a seat and an upper rim of a toilet. In the example of FIG. 13, the second clearance is smaller than the first clearance. In some embodiments, the second clearance is configured to block a portion of toilet plume from entering the user area during flushing. In some embodiments, the second clearance may be configured to block a portion of air in the user area from entering the toilet bowl during flushing. In some embodiments, an average second clearance may be at least any of about 0.05 inches, about 0.10 inches, about 0.15 inches, about 0.20 inches, about 0.25 inches, or about 0.30 inches. In some embodiments, the average second clearance may be at most any of about 0.50 inches, about 0.45 inches, about 0.40 inches, or about 0.35 inches. In some embodiments, the average second clearance may be any of about 0.05-0.50 inches, about 0.10-0.45 inches, about 0.15-0.40 inches, about 0.20-0.35 inches, or about 0.25-0.30 inches. As shown in FIG. 13, an amount of air that enters the toilet bowl through the second clearance is lower than an amount of air that enters the toilet bowl through the first clearance. According to some embodiments, the lid in the closed lid position and the seat configured to be spaced the second clearance away from the toilet bowl, does not cause any appreciable reduction in water mass flow rate out of the trapway. Therefore, there would be no negative effect on flush performance.

According to some embodiments, the seat assemblies associated with FIG. 12 and FIG. 13 reduce an amount of toilet plume flowing from a toilet bowl into a user area of the toilet and increases an amount of toilet plume flowing into the toilet plumbing (such as toilet trapway). According to some embodiments, the lid of seat assemblies associated with FIG. 12 and FIG. 13 in the closed lid position can reduce an amount of reduce an amount of toilet plume entering the user area compared to a seat assembly configuration, for example as shown in FIG. 10, by at least about 50%, about 60%, or about 70%. According to some embodiments, the lid of seat assemblies associated with FIG. 12 and FIG. 13 in the closed lid position can reduce an amount of reduce an amount of toilet plume entering the user area compared to a seat assembly configuration, for example as shown in FIG. 10, by at most about 95%, about 90%, or about 85%. According to some embodiments, the lid of seat assemblies associated with FIG. 12 and FIG. 13 in the closed lid position can reduce an amount of reduce an amount of toilet plume entering the user area compared to a seat assembly configuration, for example as shown in FIG. 10, by about 50%-95%, about 60%-90%, or about 70%-85%.

Figure 14A:
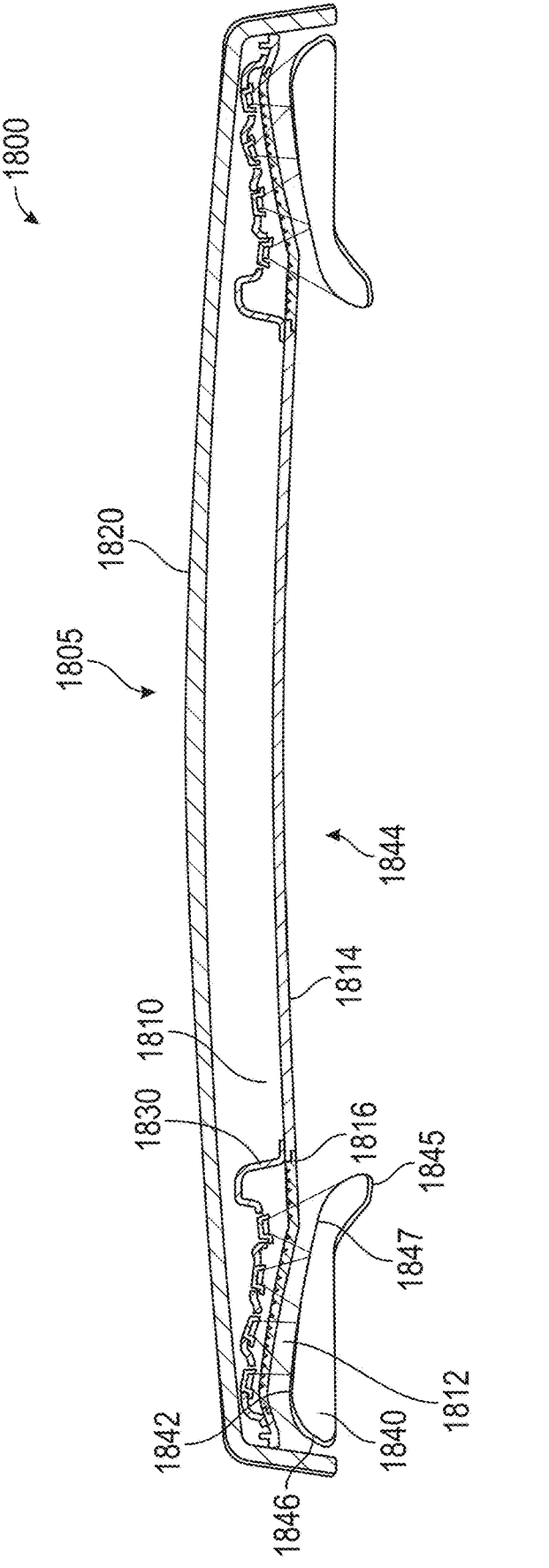
FIG. 14A shows an example of a seat assembly that includes a lid that includes an inner liner, an outer liner, and one or more support liners.

Disclosed herein is a toilet seat assembly comprising a seat and a lid hinged to the seat and movable to a closed lid position in which the lid is closed over the seat and toilet bowl to minimize toilet plume during flushing and disinfect the seat while the lid is closed over the seat. According to some embodiments, a seat assembly may include an inner liner, an outer liner, and one or more support liners. The one or more support liners may be configured to mount a plurality of UV-C lamps. FIG. 14A shows an example of a seat assembly 1400 that includes a lid 1405 that includes an inner liner 1410, an outer liner 1420, and one or more support liners 1430. The inner liner 1410 may include a shaped surface portion 1412 and a core portion 1414. The shaped surface portion 1412 may be shaped to correspond to a shape of seat 1440 of the seat assembly for covering an upper seat surface 1442 of the seat 1440 when the lid 1405 is in a closed lid position over the seat 1440 and toilet bowl. The shaped surface portion 1412 may extend from an inner rim 1445 to and an outer rim 1446 of the seat 1440. The core portion 1424 joined to the shaped surface portion 1412 may be configured to cover a central opening 1444 of the seat 1440. According to some embodiments, the shaped surface portion 1412 is joined to the core portion 1414 at a rim 1416. The rim 1416 may be located near an upper edge 1447 of an inner rim 1445 of the seat 1440. According to some embodiments, the rim 1416 may be flush with the shaped surface portion 1412 and the core portion 1414. The UV-C lamps may be directed towards an upper seat surface 1442 of the seat 1440 for disinfecting the upper seat surface 1442. According to some embodiments, the seat 1440 may be a seat type of seat V1, V2, or V3 (as shown in FIG. 13).

Figure 14B:
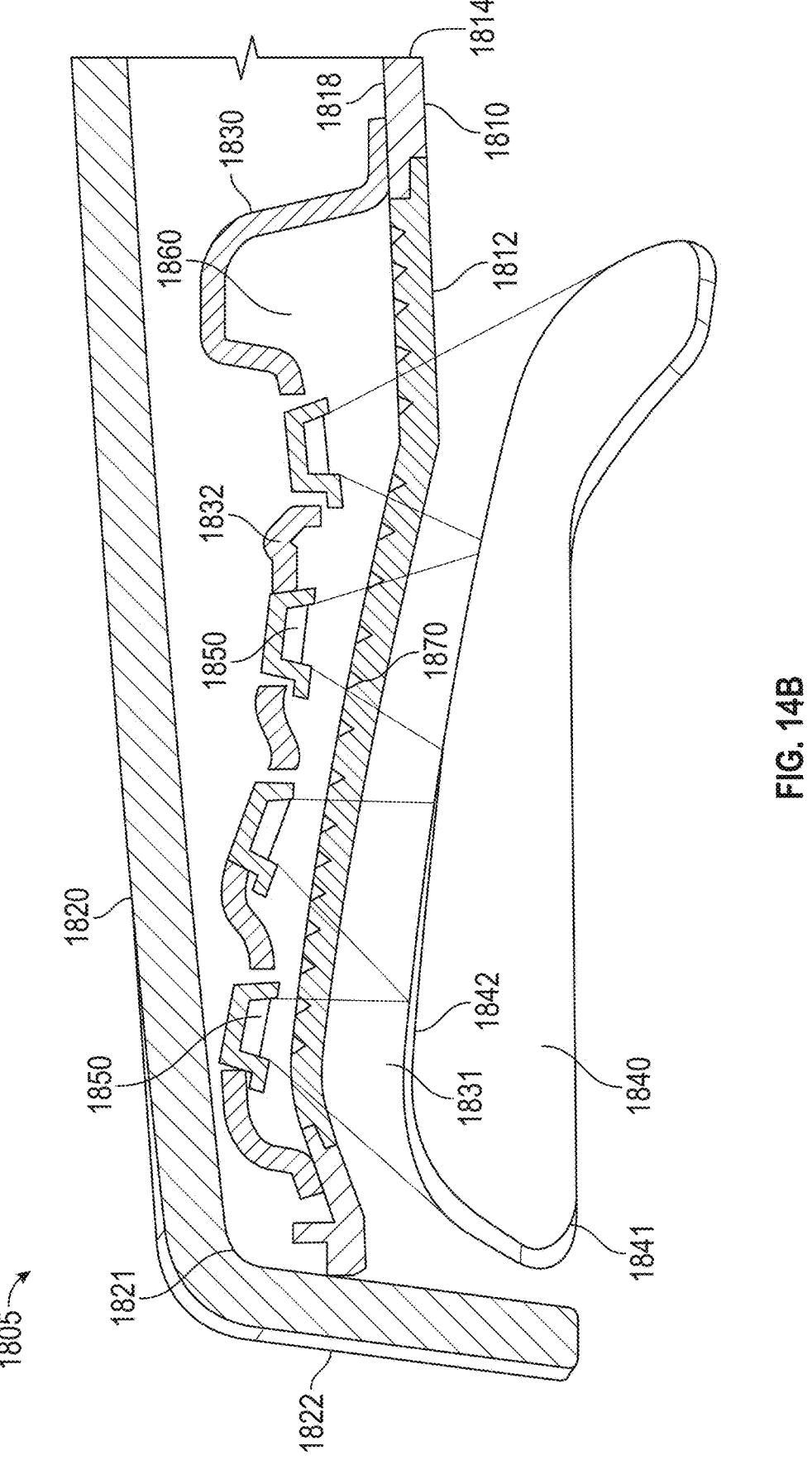
FIG. 14B shows a zoomed-in view of a portion of the lid in FIG. 14A.

FIG. 14B shows a zoomed-in view of a portion of the lid in FIG. 14A. According to some embodiments, the plurality of UV-C lamps 1450 may be positioned on an inner liner 1410 of a lid 1405. According to some embodiments, the plurality of UV-C lamps 1450 may be positioned on one or more support liners 1430 mounted on an internal surface

1418 of the inner liner 1410 of the lid 1405. The internal surface 1418 may be part of one or more of the shaped surface portion 1412 and the core portion 1414. The one or more support liners 1430 may be positioned between an outer liner 1420 and the inner liner 1410 in a hollow portion formed by the outer liner 1420 and the inner liner 1410. According to some embodiments, the inner liner 1410 may be joined to the outer liner 1420 at or near a shoulder of the outer liner 1420. The outer liner 1420 may include an edge portion 1422 configured to extend past the inner liner 1410. According to some embodiments, when the lid is in a closed lid position over the seat 1440 and the toilet bowl, the edge portion 1422 extends to or past a bottom surface 1441 of the seat 1440 to block at least a portion of light from the plurality of UV-C light from illuminating a user area outside of the toilet. The edge portion 1422 may block at least a portion of toilet plume from flowing in and out of the toilet. Light or toilet plume that travels between the edge portion 1422 and the seat 1440 into a user area of the toilet is directed downward (for example, as shown by air vector fields 102 in FIG. 1B) by the edge portion 1422.

According to some embodiments, the one or more support liners 1430 form one or more recessed portions 1460 recessed from the internal surface 1418 of the inner liner 1410. According to some embodiments, the one or more recessed portions 1460 of the shaped surface portion 1412 of the inner liner 1410 may be recessed into the hollow portion of the lid 1405 towards the outer liner 1420. The one or more recessed portions 1460 may include one or more UV-C lamps of the plurality of UV-C lamps 1450. According to some embodiments, the UV-C lamps 1450 may be directed to illuminate one or more an upper seat surface 1442 and the toilet bowl (not shown). According to some embodiments, the UV-C lamps may be directed to illuminate at least the upper seat surface 1442. According to some embodiments, the one or more recessed portions 1460 may include reflective pocket supports 1432 in the one or more support liners 1430. According to some embodiments, the reflective pocket supports 1432 may be plated plastic or additional thin metal stamped parts.

According to some embodiments, the plurality of UV-C lamps 1450 may be integrated circuit chips that are individually mounted in the recessed portion 1460. The individual UV-C chips may be connected. For example, the UV-C chips may be connected with a harness of printed film circuit. According to some embodiments, the UV-C chip may be connected with a harness via a Daisy-chain. According to some embodiments, the harness may be part of the one or more support liners 1430. According to some embodiments, the harness may be the one or more support liners 1430.

According to some embodiments, the inner liner 1410 may include a UV-C light transparent layer 1470 configured to cover the one or more recessed portions 1460 and enclose the one or more support liners 1430 in the hollow portion of the lid 1405. The UV-C transparent layer 1470 may include a plurality of lenses. The plurality of lenses may include a diamond shaped cuts for greater light diffusion. According to some embodiments, the UV-C transparent layer 1470 may be spaced at least about 0.05 inches, about 0.08 inches, about 0.1 inches, or about 0.12 inches away from the upper seat surface 1442. According to some embodiments, the UV-C transparent layer 1470 may be spaced at most about 0.5 inches, about 0.4 inches, about 0.3 inches, or about 0.2 inches away from the upper seat surface 1442. According to some embodiments, the UV-C transparent layer 1470 may be spaced about 0.05-0.5 inches, about 0.08-0.4 inches, about 0.1-0.3 inches, or about 0.12-0.2 inches away from the upper seat surface 1442.

Figure 15A:
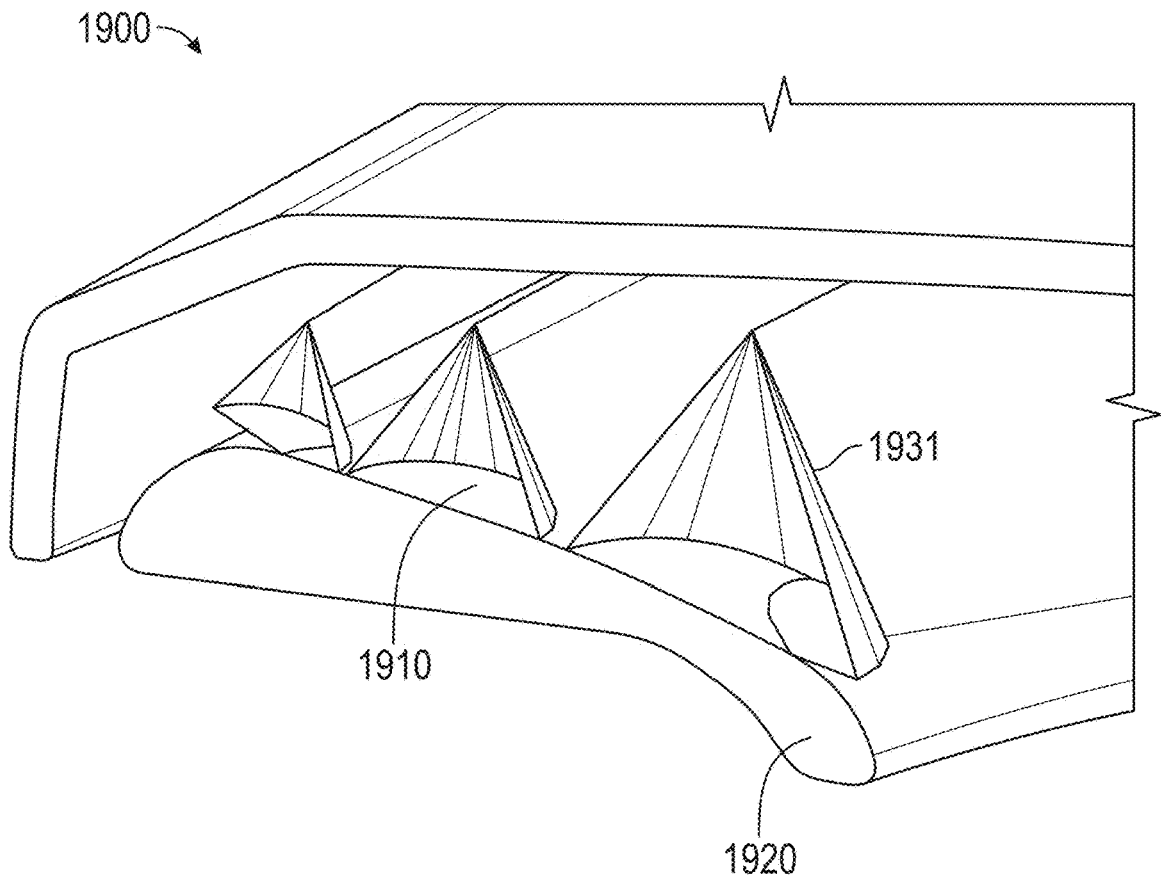
FIGS. 15A and 15B shows examples of UV-C light coverage on a seat of a seat assembly, according to some embodiments.
Figure 15B:
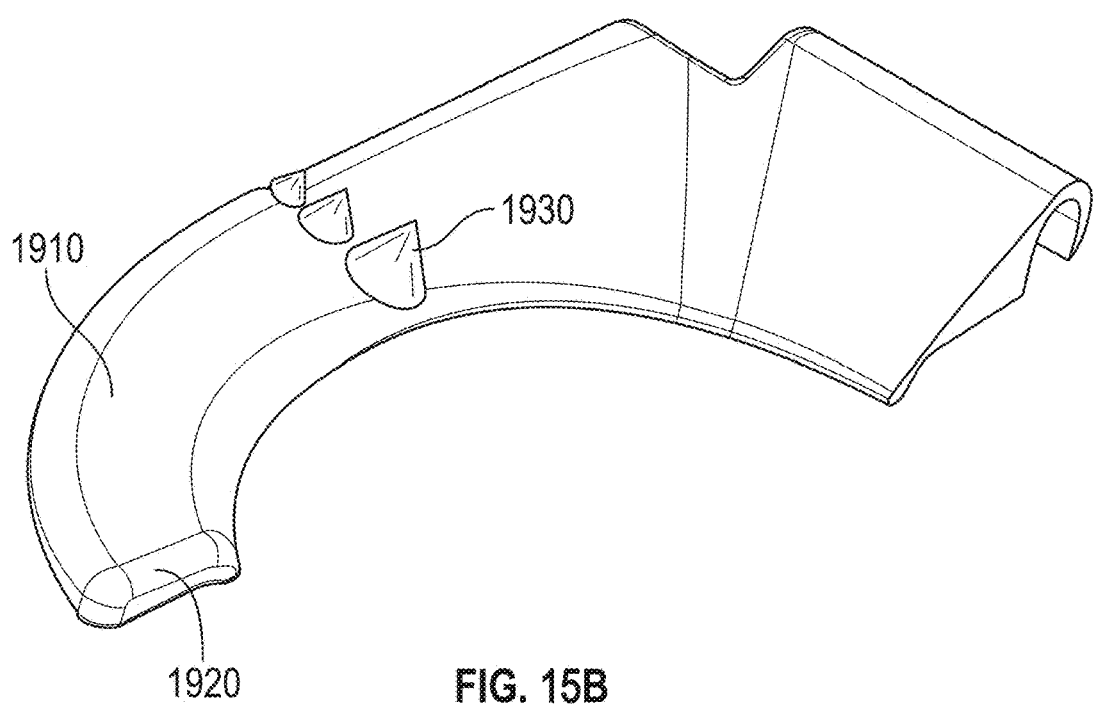

FIGS. 15A and 15B shows examples of UV-C light coverage on a seat of a seat assembly, according to some embodiments. In the example of FIG. 15, a lid 1500 includes UV-C lamps (not shown) that illuminate an upper seat surface 1510 of a seat 1540. According to some embodiments, each of the UV-C lamps illuminate the upper seat surface 1510 by at least about 90 degrees, about 100 degrees, or about 110 degrees of illumination. According to some embodiments, each of the UV-C lamps illuminate the upper seat surface 1510 by at most about 150 degrees, about 140 degrees, or about 130 degrees of illumination. According to some embodiments, each of the UV-C lamps illuminate the upper seat surface 1510 by at most about 90-150 degrees, about 100-140 degrees, or about 110-130 degrees of illumination. The degree of illumination is represented in FIGS. 15A and 15B by illumination cones 1531. As indicated by the illumination cones 1531, UV-C light is directed towards the seat 1540. According to some embodiments, the UV-C lamps may be arranged in a plurality of rows configured to illuminate the upper seat surface 1510. According to some embodiments, the UV-C lamps may be integrated chips configured to provide a cone of illumination 1531. According to some embodiments, the UV-C lamps may be positioned in a recessed portion of the lid 1500 (as described in FIGS. 14A and 14B).

Figure 16A:
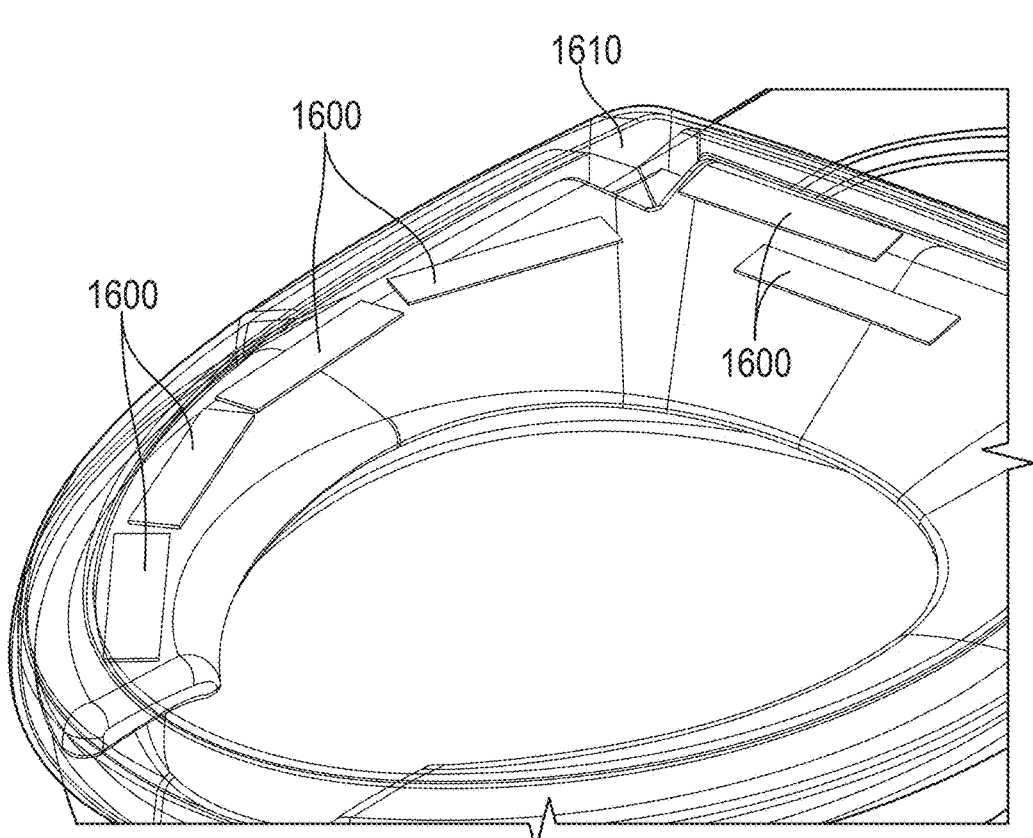
FIGS. 16A and 16B respectively show a top view (see-through for illustrative purposes) and a bottom view of a plurality of UV-C lamps, according to some embodiments.
Figure 16B:
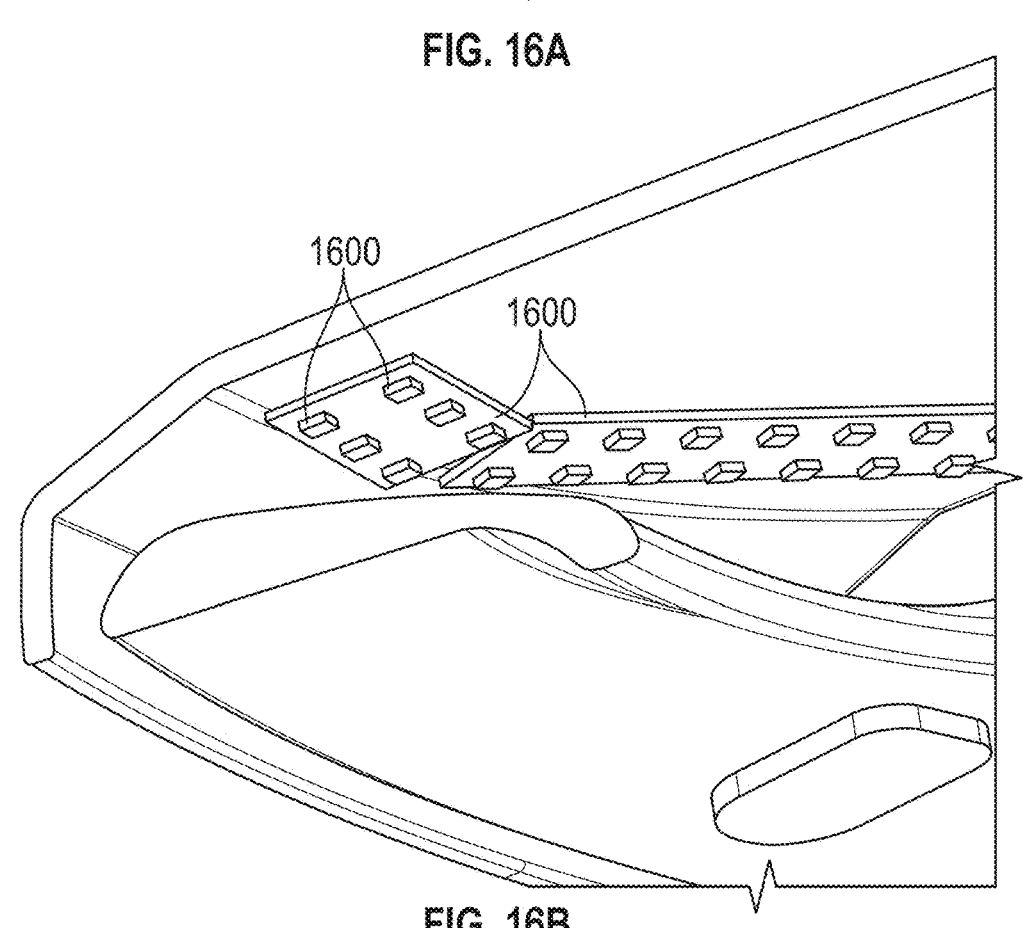

According to some embodiments, the plurality of UV-C lamps may be integrated chips that are mounted to one or more circuit boards. According to some embodiments, the plurality of UV-lamp may include the one or more circuit boards. FIGS. 16A and 16B respectively show a top view (see-through for illustrative purposes) and a bottom view of a plurality of UV-C lamps, according to some embodiments. In the example of FIG. 16A, a plurality of circuit boards 1600 mounted to an underside of lid 1610 are shown. In the example of FIG. 16B, a plurality of UV-C chips 1620 are shown on the plurality of circuit boards 1600. The plurality of circuit boards 1600 ease assembly and reduce harness complexity. For example, a plurality of UV-C chips may be mounted to a first circuit board and a second plurality of UV-C chips may be mounted to a second circuit board.

Figure 17A:
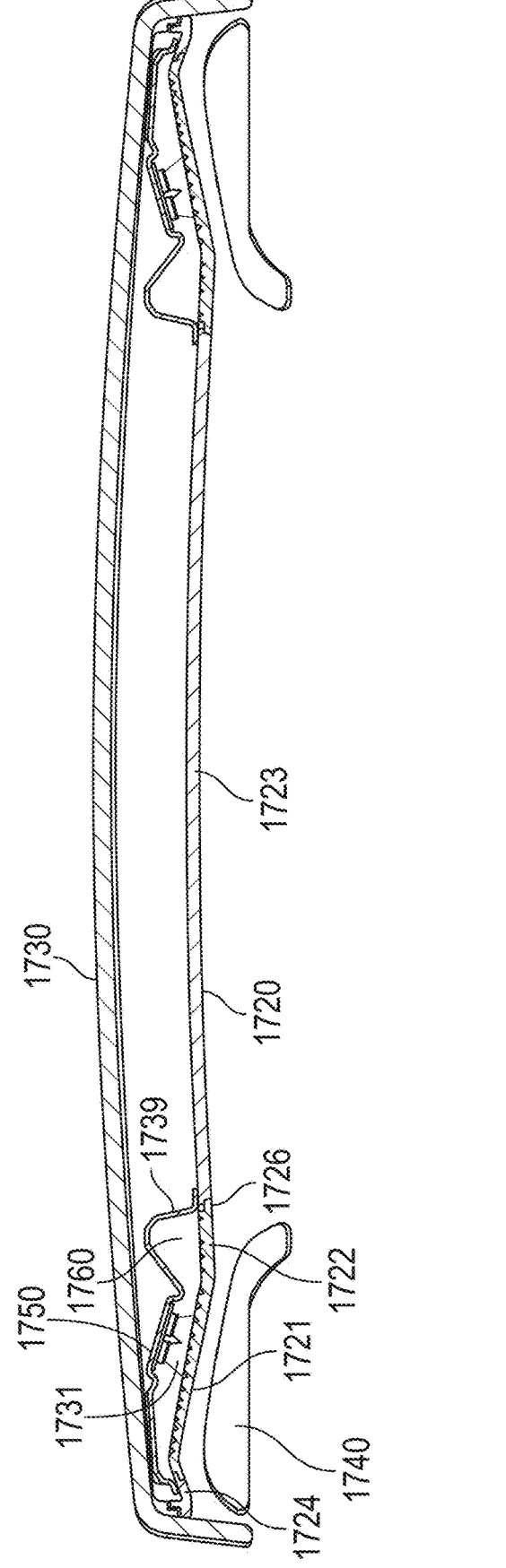
FIGS. 17A-17D show examples of a plurality of UV-C lamps positioned in a lid, according to some embodiments.
Figure 17B:
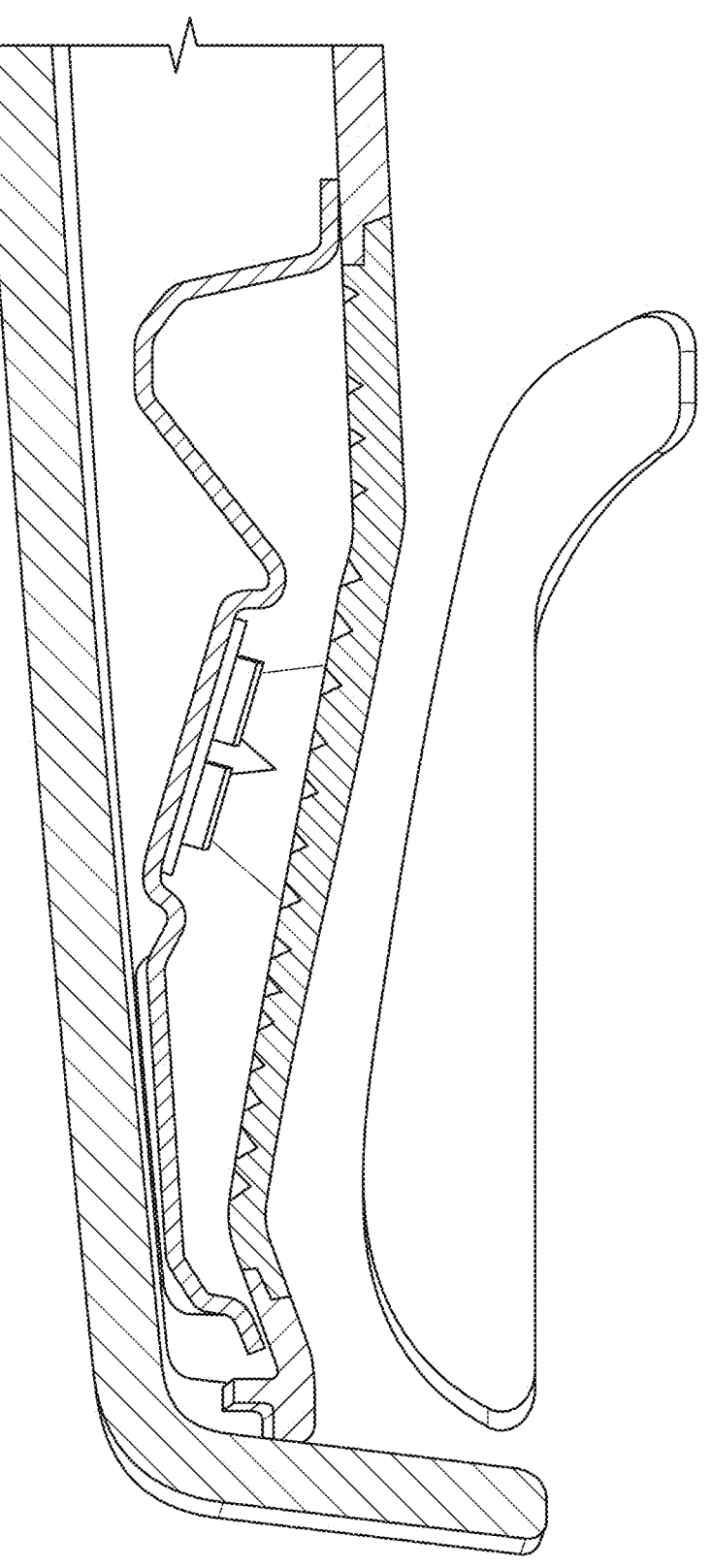

According to some embodiments UV-C chips mounted on a plurality of circuit boards may be positioned in one or more recessed portions of a lid. According to some embodiments, a plurality of UV-C lamps may be positioned in a lid to provide maximum seat coverage. FIGS. 17A-17D show examples of a plurality of UV-C lamps positioned in a lid, according to some embodiments. In the example of FIG. 17A, a seat assembly 1700 includes a lid 1710 that includes an inner liner 1720, an outer liner 1730, and one or more support liners 1739, according to some embodiments. A plurality of UV-C lamps 1750 may be positioned in a recessed portion 1760 of the lid 1710. The one or more liners 1739 may be configured to support the UV-C lamps 1750 at an optimal distance away from a UV-C transparent layer 1722 of the inner liner 1720. The UV-C transparent layer 1722 may be configured to form a surface of the inner liner 1720. According to some embodiments, the UV-C transparent layer 1722 may be flush with a first joint 1724 of a shaped surface portion 1721 of the inner liner 1720 and a second joint 1726 that joins the shaped surface portion 1721 and a core portion 1723 of the inner liner 1720. FIG. 17B shows a zoomed-in view of a portion of the lid in FIG. 17A.

Figure 17C:
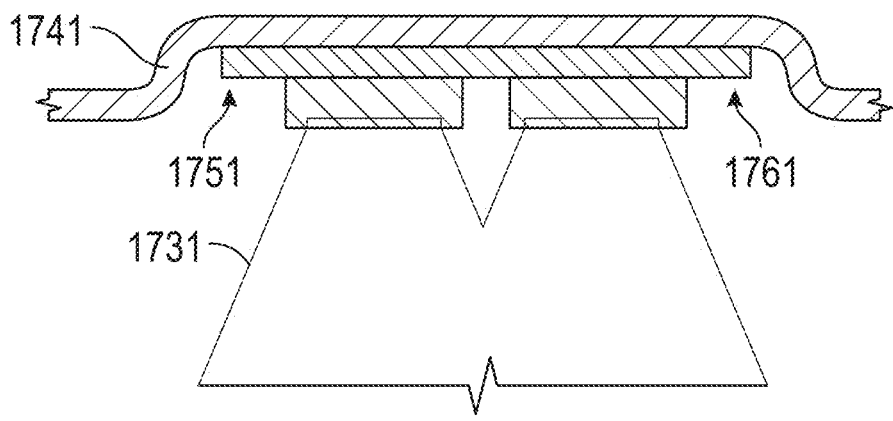

In the example of FIG. 17C, a lid 1702 includes a plurality of UV-C lamps 1751 mounted to one or more support liners 1741 in one or more recessed portions 1761 of the lid 1701. In the example of FIG. 4C, the plurality of UV-C lamps 1751 are exposed in the one or more recessed portions 1761.

In some embodiments, a cleaning cycle of a toilet seat assembly depicted in any of FIG. 14A, 14B, 15A, 15B, 16A, 16B, 17A, 17B, 17C, or 17D may be configured to automatically initiate when the toilet lid assumes a closed lid position. For example, a toilet seat assembly according to some embodiments described herein can include a controller configured to automatically initiate a cleaning cycle by turning on the UV-C lights to disinfect the toilet seat. The controller may automatically initiate the disinfection/cleaning cycle upon detecting that the toilet lid is in a closed lid position, for example. In some embodiments, a cleaning cycle of a toilet seat assembly depicted in any of FIG. 14A, 14B, 15A, 15B, 16A, 16B, 17A, 17B, 17C, or 17D may be configured to manually initiate upon receiving a user input. For example, a user might press a button, trigger a pedal, or trigger a motion sensor to initiate a disinfection/cleaning cycle.

Figure 17D:
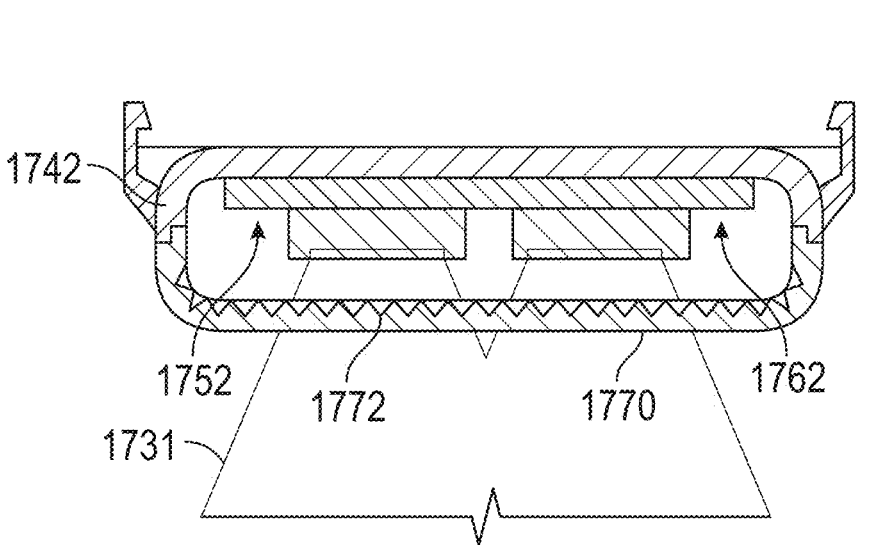

In the example of FIG. 17D, a lid 1702 includes a plurality of UV-C lamps 1752 mounted to one or more support liners 1742 in one or more recessed portions 1762 of the lid 1702. In contrast to the example of FIG. 4C, FIG. 4D shows that the plurality of UV-C lamps 1752 are in the one or more recessed portions 1762 and covered by a UV-C transparent layer 1770. According to some embodiments, an additional lens could be packaged with each UV-C lamp for greater light diffusion within the one or more recessed portions 1762 or additional lens could be inserted into the lid 1702 with a flush mounted flange. According to some embodiments, the UV-C transparent layer may include diamond shaped cuts or lenses 1772 to increase light diffusion. As shown respectively in the examples of FIG. 14A-14B, 15A-15B, 120A-D, illumination cones 1431, 1531, and 2031 are directed respectively towards seat 1140, 1240, and 1740.

Figure 18A:
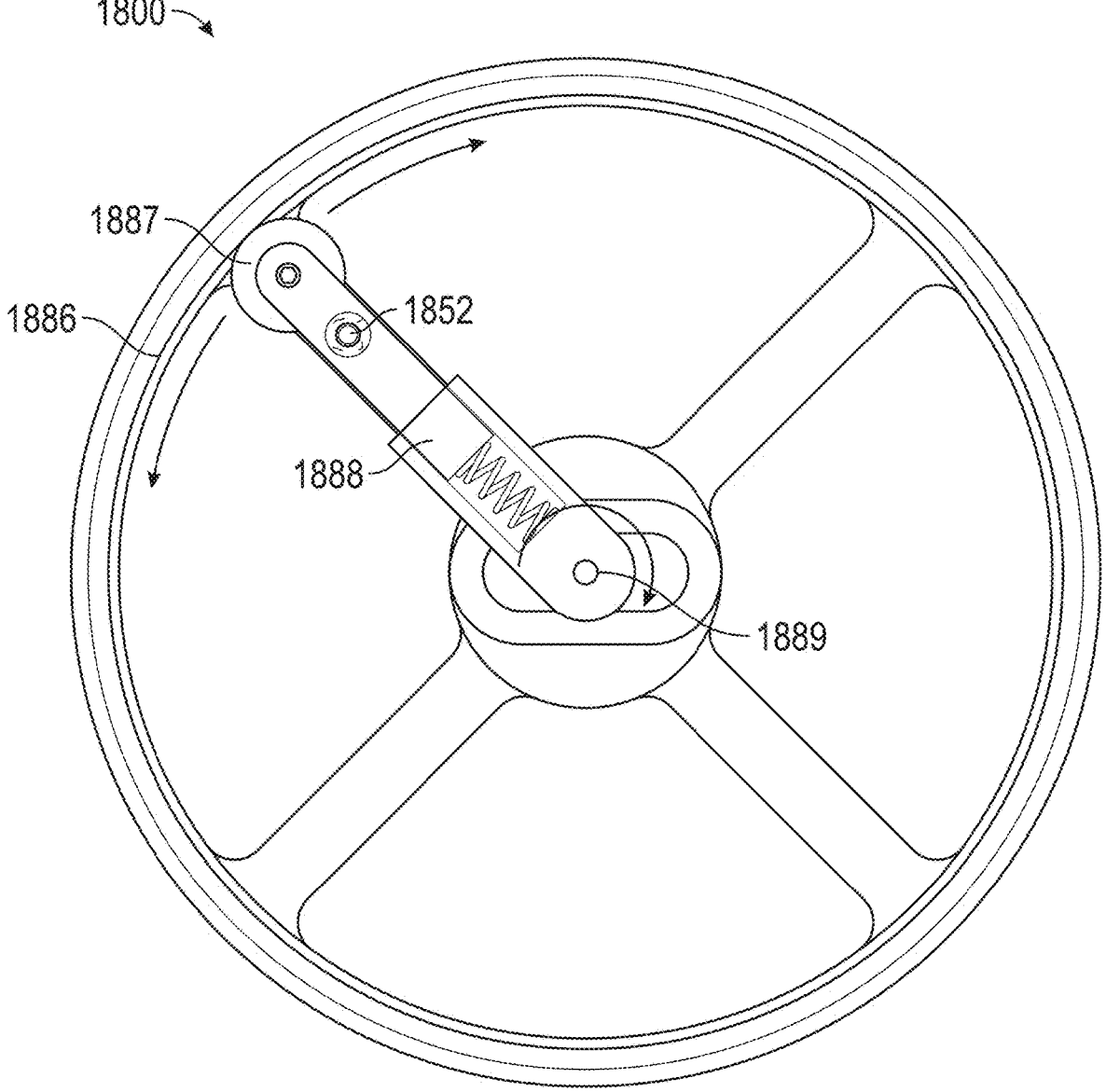
FIGS. 18A-18E show examples of a dynamic toilet seat assembly with one or more UV-C lights configured to travel around the perimeter of a toilet seat, according to some embodiments.

In some embodiments, a toilet seat according to some embodiments may include dynamic UV-C lamp mechanism. For example, FIG. 18A shows a mechanism 1800 by which the UV-C lamps can travel 360 degrees such that the surface of the toilet seat is treated with UV-C light. Such a mechanism can reduce the total number of UV-C lamps used. This may be particularly cost-effective, since UV-C LEDs are quite expensive. Further, UV-C light scatters relatively quickly after only traveling a short distance though the atmosphere. A typical UV-C LED will only lethally affect a small area from about 1 inch to about 3 inches in diameter. Given the relatively large surface area of a toilet seat, it would take a considerable amount of UV-C LEDs to cover the full area of the seat. Therefore, an embodiment with dynamic UV-C would require a much fewer number of LEDs to cover the entire target area. Embodiments using fewer UV-C LEDs dynamically would have a slightly longer cycle time but would be more cost effective.

In some embodiments, a dynamic UV-C light mechanism includes one or more arms projecting radially from a central location (with respect to a track) to the track. The track may be in a shape that is complementary to the shape of a toilet seat and located on the lid of the toilet seat assembly. The arms each comprise one or more UV-C lights at a distal end. The one or more lights are configured to direct UV-C light in the direction of the upper surface of the toilet seat when the toilet lid is in a closed lid position. In some embodiments, the UV-C light (or lamp, LED) may direct light towards the surface of the toilet seat in a direction that is perpendicular to the planar surface of the toilet seat. In some embodiments, the UC-V light may direct light towards the surface of the toilet seat at an angle that is less than or greater than 90 degrees (or perpendicular) to the planar surface of the toilet seat. In some embodiments, directing light at an angle to the planar surface of the toilet seat can generate a larger target area, or the area within which the surface of the toilet seat is treated with the UV-C light.

In some embodiments, a cleaning cycle of the dynamic UV-C light mechanism may be configured to automatically initiate when the toilet lid assumes a closed lid position. In some embodiments, a cleaning cycle of the dynamic UV-C light mechanism may be configured to manually initiate upon receiving a user input. In some embodiments, a cleaning cycle may comprise a single 360 degree rotation of the one or more arms. In some embodiments, a cleaning cycle may comprise two or more 360 degree rotations of the two or more arms. In some embodiments, a cleaning cycle may comprise less than a 360 degree rotation. For example, an embodiment comprising two arms may achieve a full cleaning cycle after a 180 degree rotation.

As shown in FIG. 18A, dynamic UV-C mechanism 1800 includes a track 1886, a wheel 1887, an arm 1888, a UV-C lamp 1852 located in arm 1888, and a motor 1889.

Utilizing a simple motor drive 1889 connected to a telescopic/spring-loaded arm 1888 that is aligned with cam track 1886, the simple circular motion can be transformed to match the oval shape of the toilet seat. The mechanism (including track 1886) may be housed within a toilet seat lid or a toilet bowl. In an embodiment in which the UV-C light comes from underneath the toilet seat (e.g., the mechanism is located within the toilet bowl), the toilet seat may be transparent such that the UV-C light can refract on the top surface of the toilet seat. (Note that materials that are transparent to UV-C light may be opaque to visible light, and vice versa.)

Figure 18B:
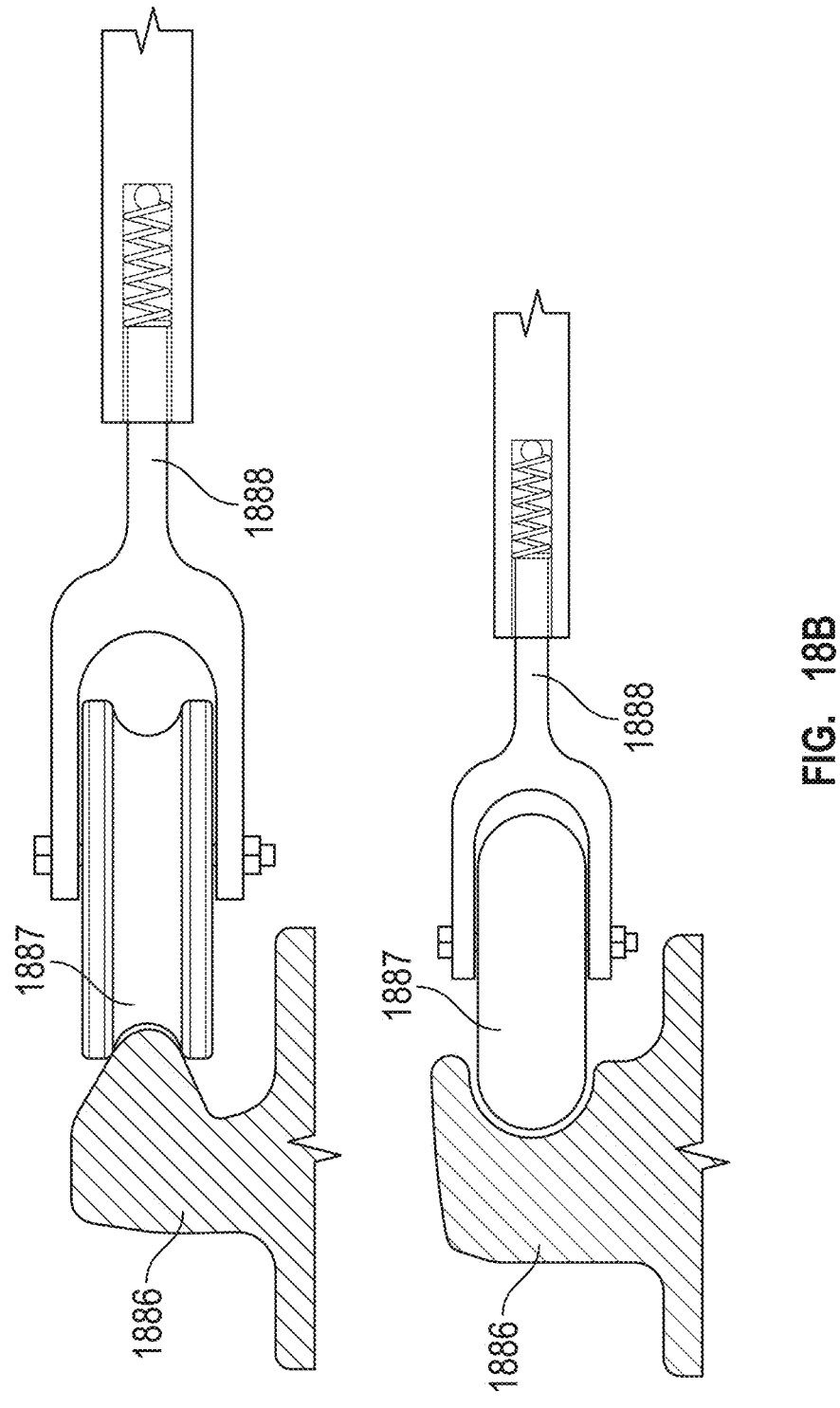

As shown, the dynamic UV-C light mechanism of FIGS. 18A and 18B shows a spring loaded and/or telescopic arm. The spring can apply pressure to keep the cam follower (i.e., wheel 1887) fully engaged with the track even when subjected to lateral shock loading.

In some embodiments, track 1886 may be built into a toilet seat lid or a toilet bowl. The UV-C lamp 1852 may be located in an arm 1888 that is configured to pivot at a central location. The central location may be central with respect to the toilet seat liner and/or the track 1886. In some embodiments, the arm may be driven by a motor 1889 (e.g., DC motor, servo motor). At the distal end of arm 1888 (i.e., the end furthest from the central location from which the arm 1888 pivots) is a wheel 1887 that is configured to roll along an interior surface of the track 1886.

In some embodiments, the arm 1888 may be spring-loaded. In some embodiments, the arm 1888 may be telescoping. In some embodiments, the arm 1888 may be telescoping and spring-loaded. In some embodiments, the arm 1888 may include any type of linear motion mechanism such as linear bearings and shaft, rack and pinion, accordion, 4-bar linkage, etc. Because most toilet seats are oblong or elliptical in shape, they do not have a constant radius. Thus, an arm 1888 with telescoping and/or spring-loaded capabilities can reach completely rotate around a toilet seat having a variable radius. This ensures that one or more UV-C lamps 1852 can reach the surface of the toilet seat to adequately sanitize the surface of the toilet seat.

FIG. 18B shows two side views of a dynamic UV-C mechanism, according to some embodiments. Each side view shows a different geometry by which the wheel 1887 might mate with the track 1886. As shown in the top side view, the track 1886 can include a male connection and the wheel 1887 can include a female connection. Stated differently, track 1886 can comprise a rounded protrusion configured to next within a rounded carve-out of wheel 1887. When coupled, the wheel 1887 is configured to slide circumferentially along an interior of track 1886 without uncoupling.

As shown in the bottom side view, the track 1886 can include a female connection and the wheel 1887 can include a male connection. Stated differently, wheel 1887 can include a standard rounded wheel shape that is configured to nest within a carve-out of the track 1886. When coupled, the wheel 1887 is configured to slide circumferentially along an interior of track 1886 without uncoupling.

The cam follower (i.e., wheel 1887) can take the form of several geometries including a fully rotational wheel, a static low-friction lobe, roller pin and slot, and have convex or concave geometry that complements the cam track geometry, etc. Other mechanisms for dynamic LED travel can include a belt or drive chain that pulls/pushes the LEDs around the oval toilet seat. Others can include using electromagnetism, or other powered methods such as using energy from the water supply pressure, electrical, chemical, solar, etc. In order for the wires that supply power to the UV-C light sources on the moment arm a simple electrical slip ring can be utilized.

Figure 18C:
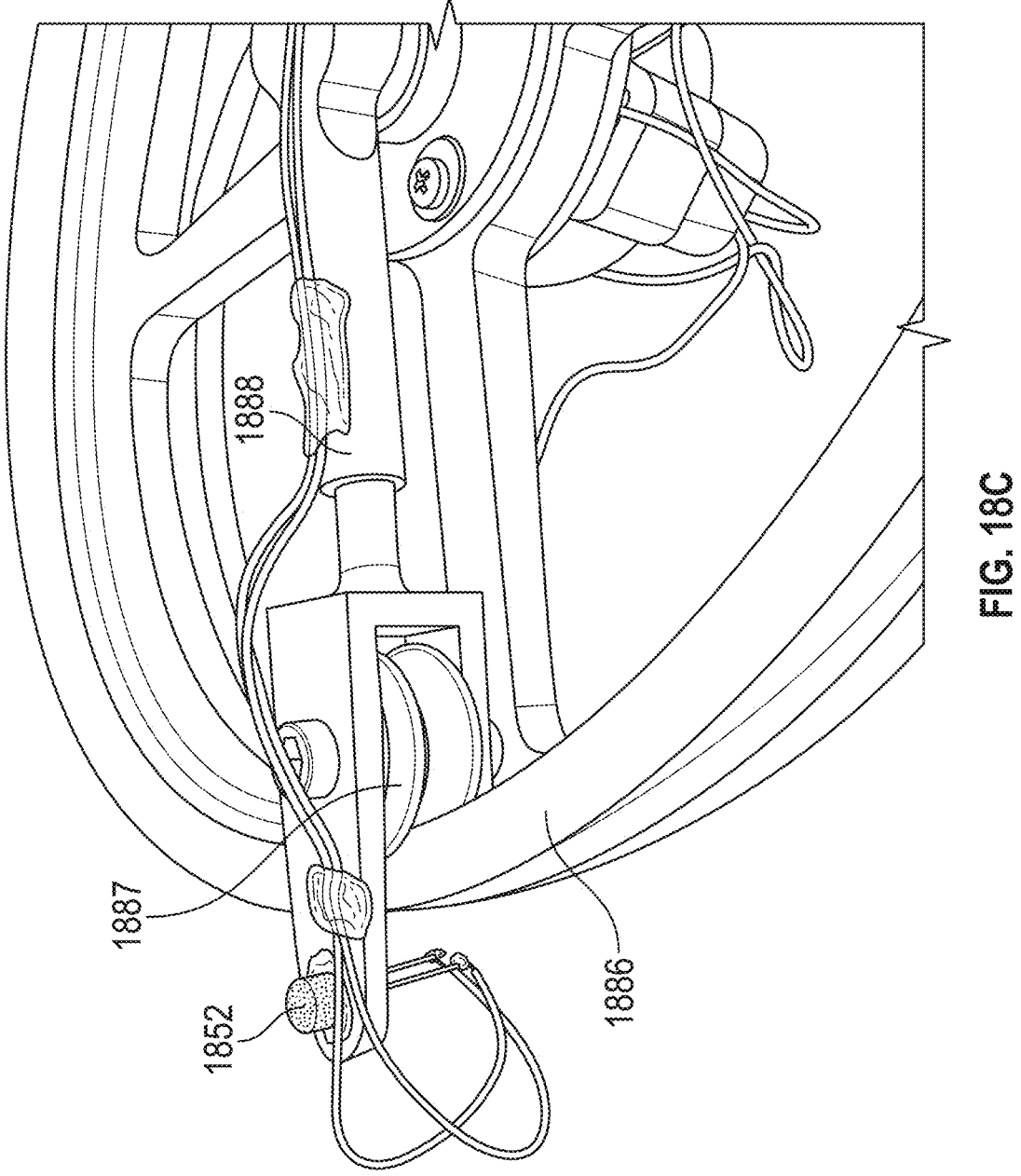

FIG. 18C shows an image of a dynamic UV-C light mechanism according to some embodiments. The image shows a portion including track 1886, wheel 1887, UV-C light 1852, and arm 1888.

Figure 18D:
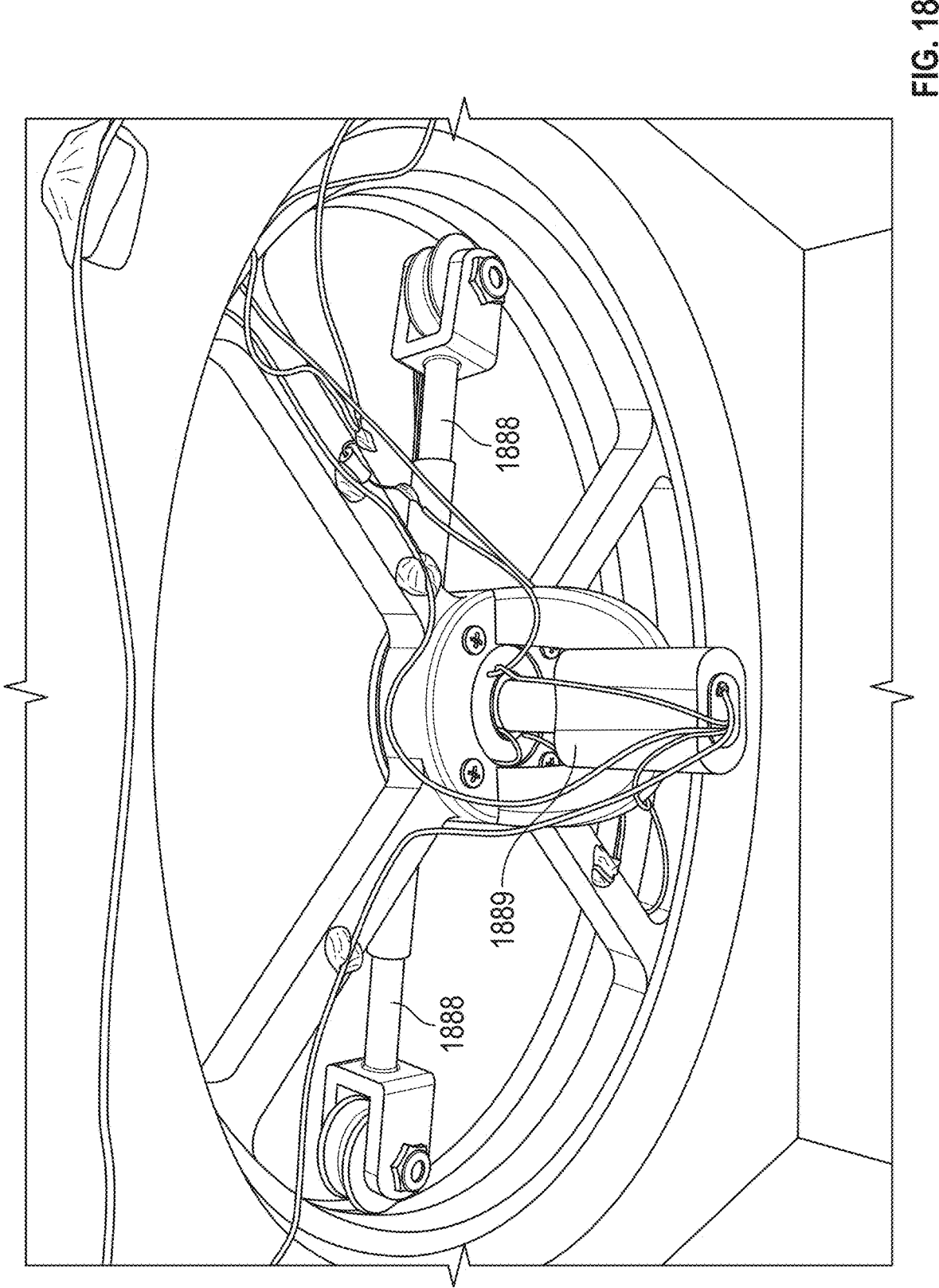

FIG. 18D shows another image of a dynamic UV-C light mechanism according to some embodiments. This particular image is a bottom view of a dynamic UV-C light mechanism. The portion shown includes motor 1889 and two arms 1888. Note that the dynamic UV-C light mechanisms described herein can include one, two, three, four, five, six, or more arms. The distal end of each arm 1888 may include one or more UV-C lamps. In some embodiments, a distal end of an arm 1888 may include one, two, three, four, or more UV-C lights.

Figure 18E:
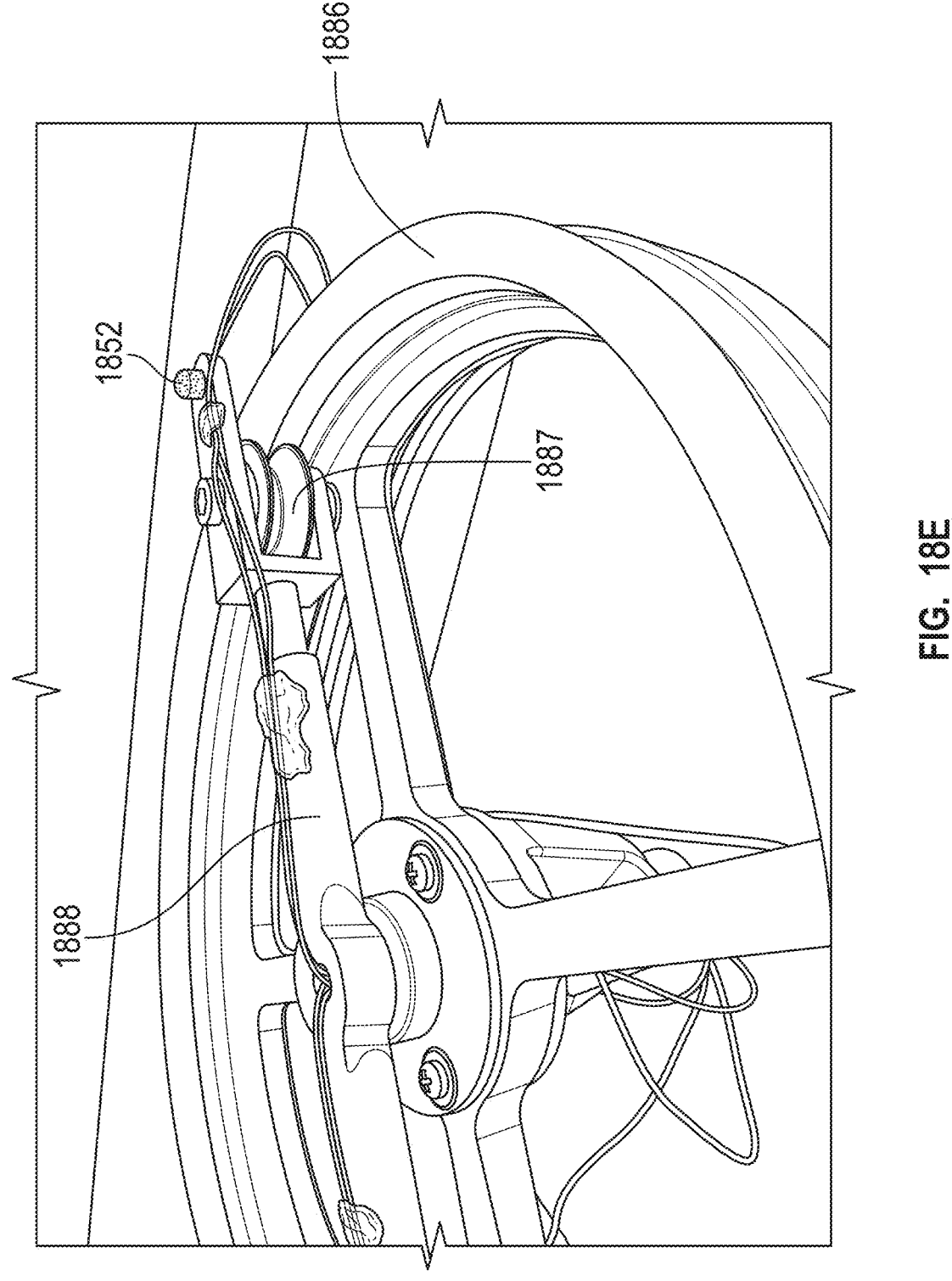

FIG. 18E shows a close up image of a dynamic toilet seat assembly according to some embodiments. Shown is arm 1888, wheel 1887, UV-C light 1852, and track 1886.

Figure 19A:
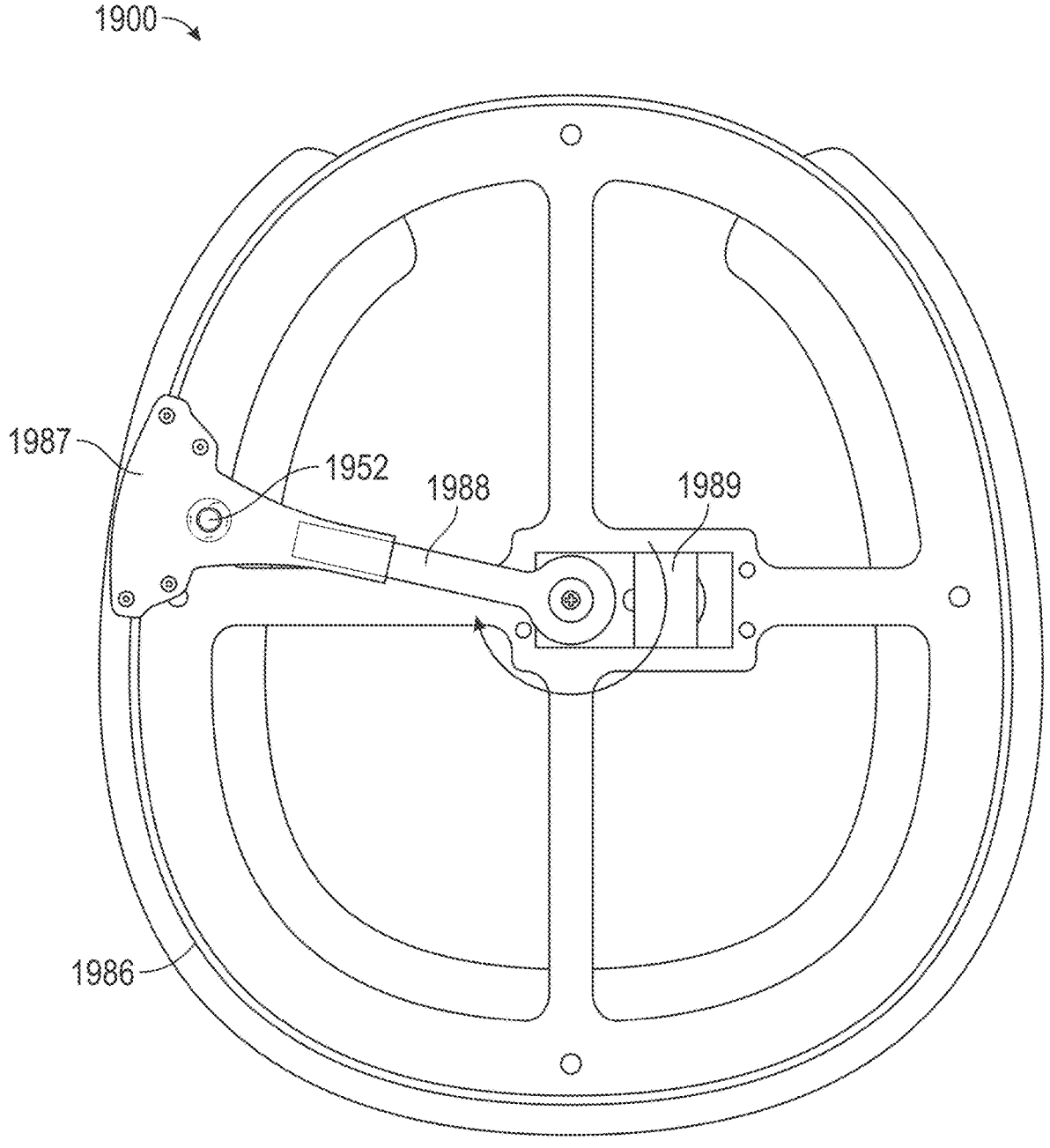
FIGS. 19A and 19B show examples of a dynamic toilet seat assembly with one or more UV-C lights configured to travel around the perimeter of a toilet seat, according to some embodiments.

FIG. 19A shows another embodiment of a dynamic UV-C light mechanism 1900 for a toilet seat. Similar to the mechanism 1800 of FIGS. 18A and 18B, mechanism 1900 of FIG. 19 shows a track 1986, along which sliding mechanism 1987 is configured to slide along. Mechanism 1900 also includes a motor 1989 (e.g., DC motor, servo motor) located at a point from which arm 1988 is configured to pivot. UV-C lamp/LED 1952 may be located within sliding mechanism 1987 or arm 1988. In some embodiments, as explained with respect to arm 1888 of FIGS. 18A and 18B, arm 1988 may include a mechanism by which its length may adjust depending on the radius of the mechanism 1900. For example, arm 1988 may be fitted with a telescope, spring, linear bearings and shaft, rack and pinion, accordion, and/or 4-bar linkage mechanism.

Unlike the mechanism 1800, the sliding mechanism 1987 of mechanism 1900 encompasses track 1986 such that it slides along both an interior surface and an exterior surface of track 1986 simultaneously.

Figure 19B:
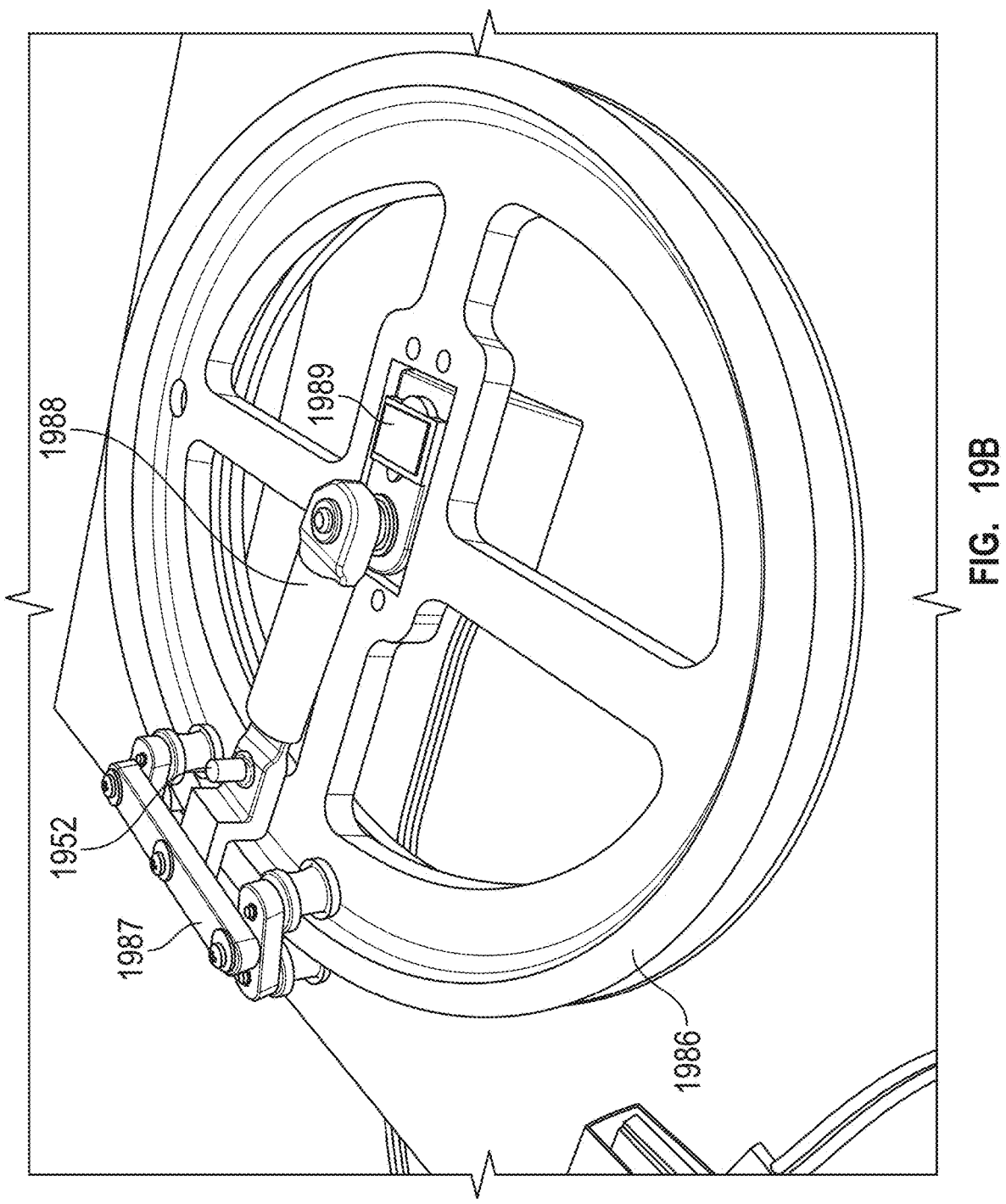

FIG. 19B provides an image of a dynamic toilet seat assembly comprising a mechanism 1900 that encompasses track 1986 such that mechanism 1900 slides along both an interior surface and an exterior surface of track 1986 simultaneously.

Figure 20A:
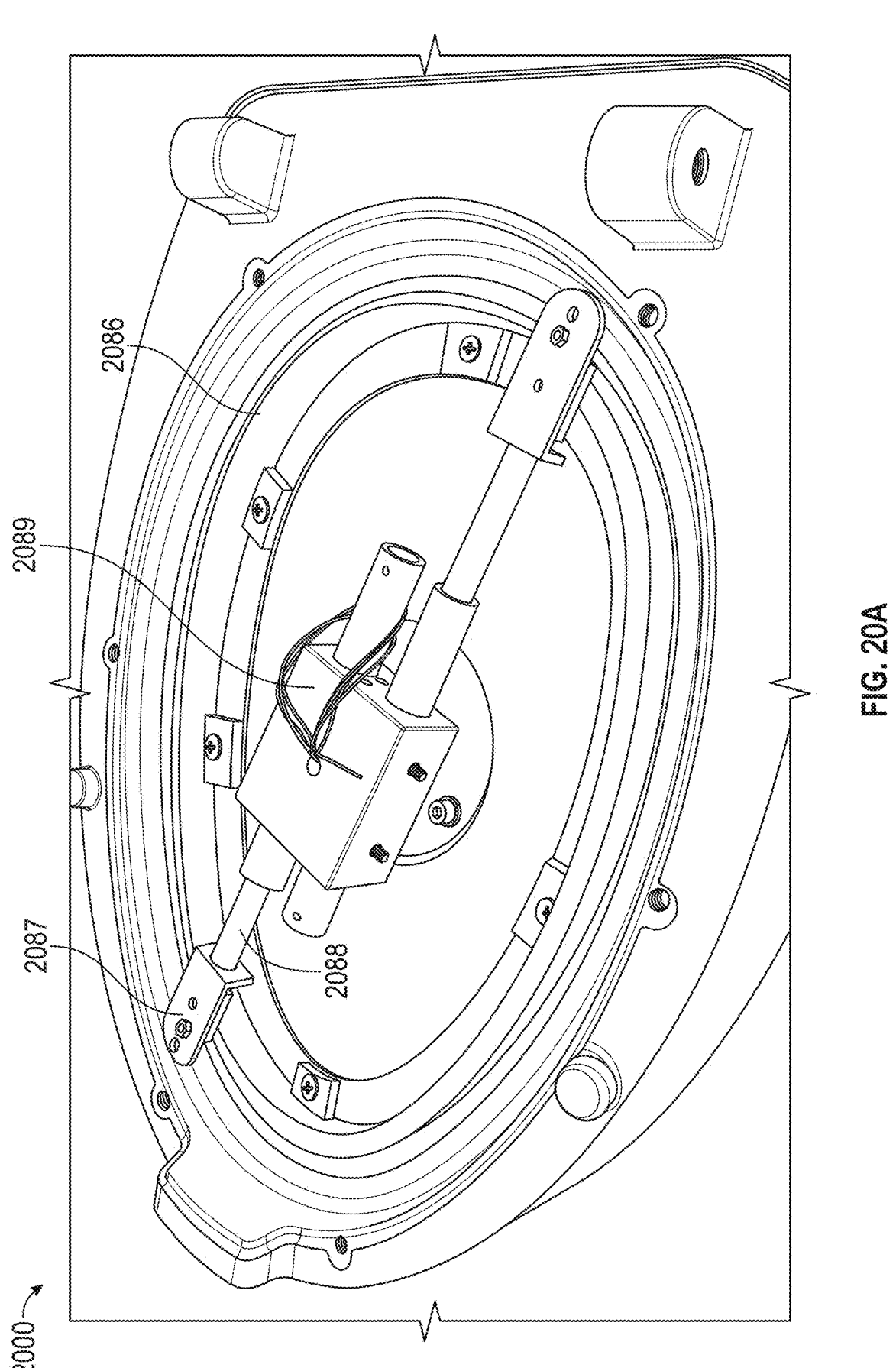
FIGS. 20A-20C show an example of a dynamic toilet seat assembly with one or more UV-C lights configured to travel around the perimeter of a toilet seat, according to some embodiments.
Figure 20B:
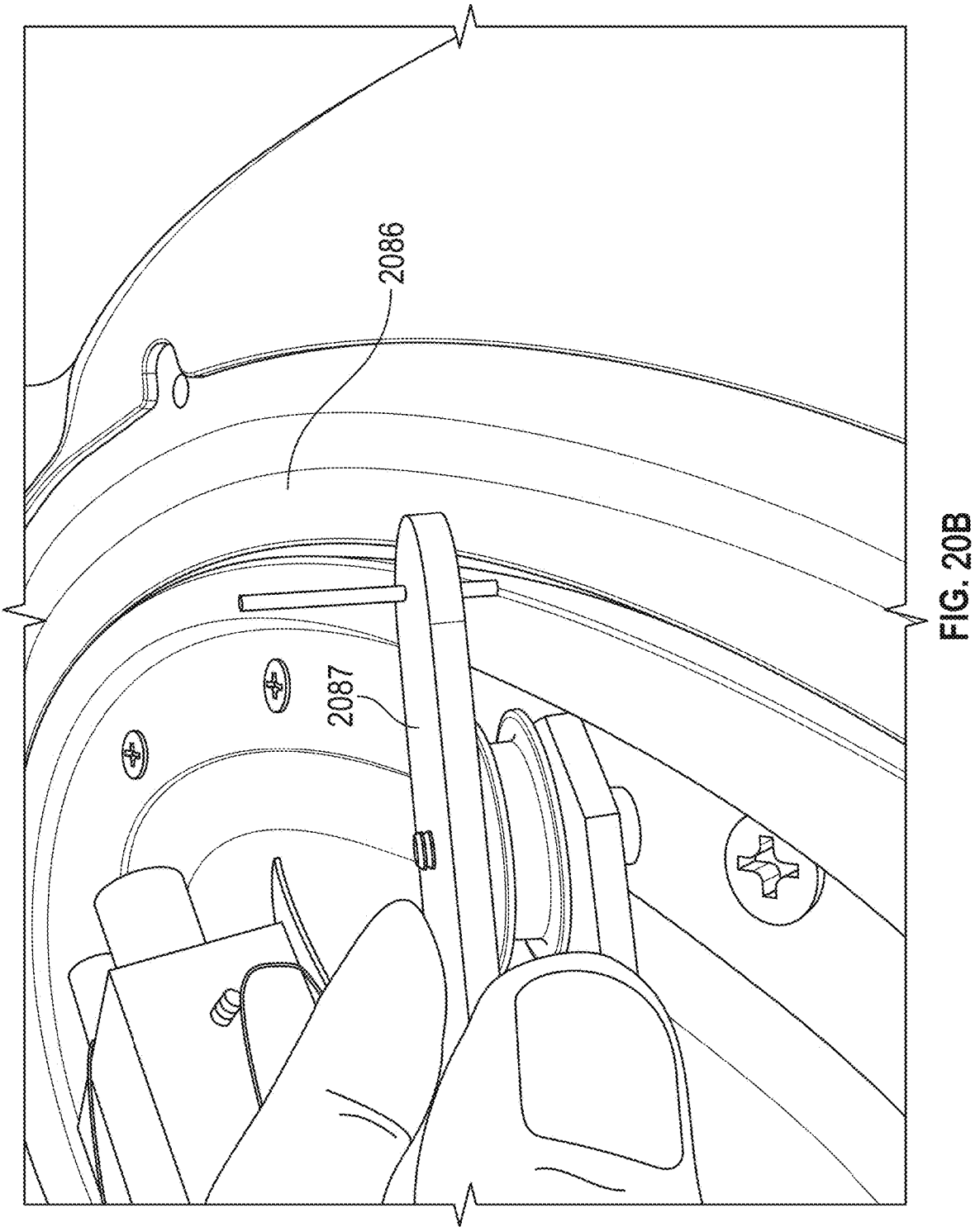
Figure 20C:
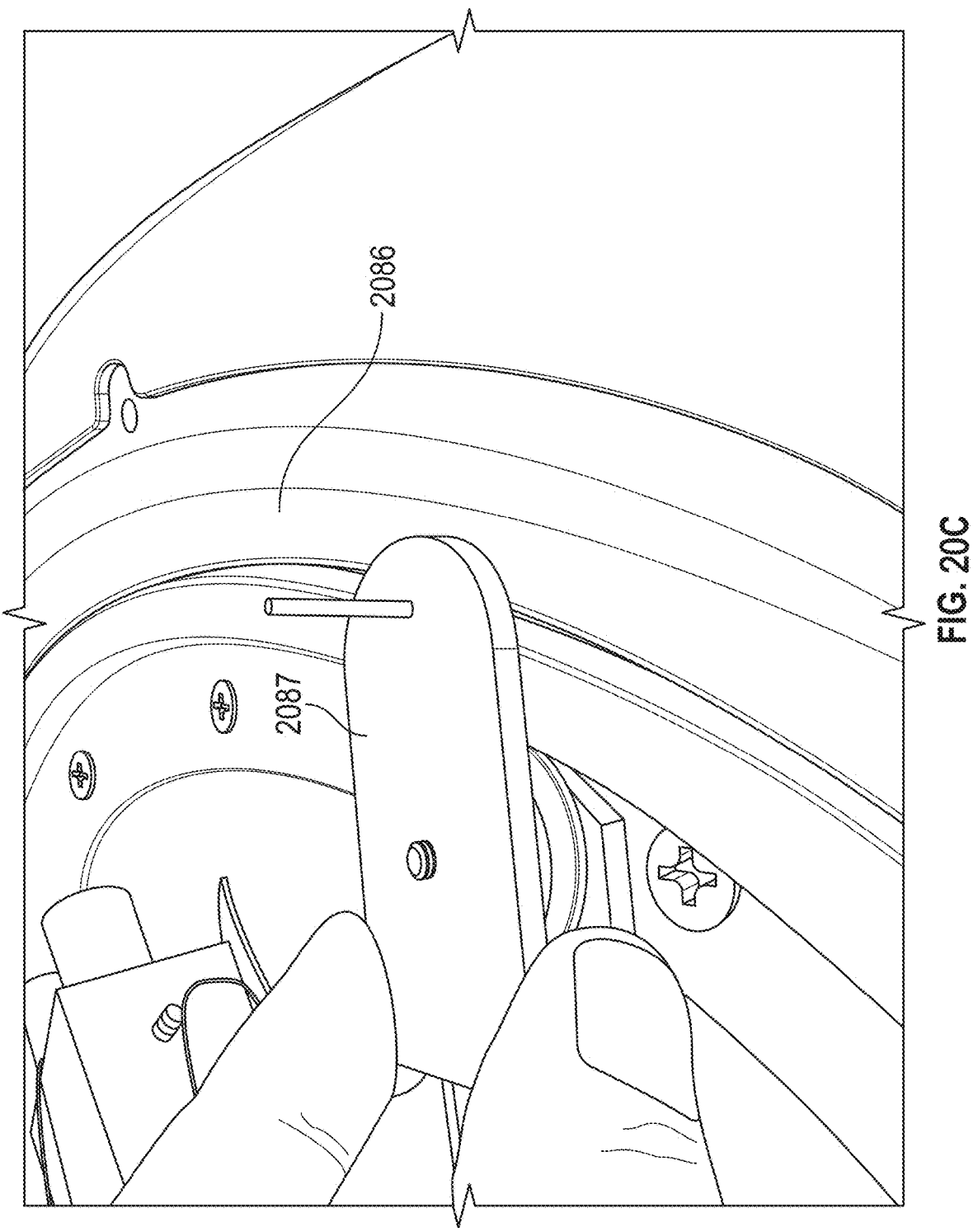

FIG. 20A-20C show an embodiment of a dynamic toilet seat assembly 2000 comprising a track 2086 that is recessed within the lid of the toilet seat assembly 2000. In this embodiment, the track 2086 is recessed into the lid of the toilet seat assembly, and the distal end 2087 (or mechanism 2087) moves along track 2086 using a pin and/or roller bearing. The connection here (e.g., pin and/or roller bearing) is shown in closer detail in FIGS. 20B and 20C. The dynamic UV-C mechanism is configured to rotate circumferentially such that the toilet seat surface is treated by the one or more UV-C lights. As with the embodiments shown and described with respect to FIGS. 18A-18E and 19A and 19B, the arm(s) of dynamic toilet seat assembly may be telescoping and/or spring-loaded such that the arm(s) can rotate around an oval-shaped toilet seat assembly.

In some embodiments of a dynamic toilet seat assembly, only one arm is included. In some embodiments, two arms are included. In some embodiments, three, four, five, or six arms are included. In some embodiments, more arms can ensure that the toilet seat is sufficiently cleaned with only a single rotation of the mechanism.

Figure 21:
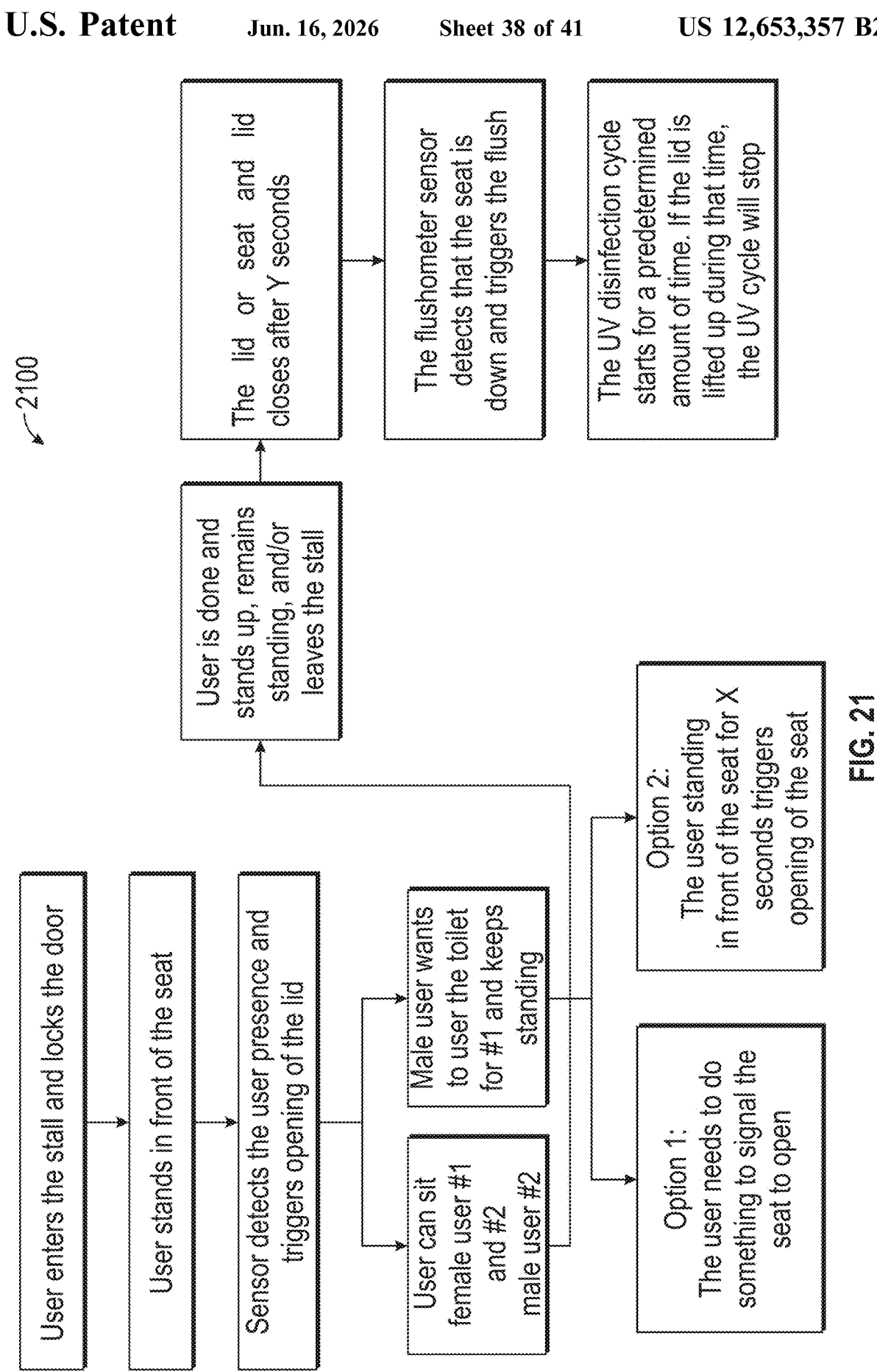
FIG. 21 shows a flowchart that describes a method of controlling a toilet that includes a seat assembly that include a lid and a seat, according to some embodiments.

FIG. 21 shows a flowchart that describes a method 2100 of using a toilet that includes a seat assembly that include a lid and a seat, according to some embodiments. According to some embodiments, the method 2100 may implemented with seat assemblies shown in FIGS. 14A-14B, 15A-15B, 16A-16B, and 17A-17D.

According to some embodiments, the X seconds of method 2100 may be at least about 5 seconds, 10 seconds, or 15 seconds. According to some embodiments, the X seconds of method 2100 may be at most about 60 seconds, about 50 seconds, or about 40 seconds. According to some embodiments, the X seconds of method 2100 may be at about 5-60 seconds, about 10-50 seconds, or about 15-40 seconds.

According to some embodiments, the Y seconds of method 2100 may be at least about 5 seconds, about 10 seconds, or about 15 seconds. According to some embodiments, the Y seconds of method 2100 may be at most about 60 seconds, about 50 seconds, or about 40 seconds. According to some embodiments, the Y seconds of method 2100 may be at about 5-60 seconds, about 10-50 seconds, or about 15-40 seconds.

According to some embodiments, the predetermined amount of time of method 2100 may be at least about 20 seconds, about 30 seconds, or about 45 seconds. According to some embodiments, the predetermined amount of time of method 2100 may be at most about 120 seconds, about 100 seconds, or about 80 seconds. According to some embodiments, the predetermined amount of time of method 2100 may be about 20-120 seconds, about 30-100 seconds, or about 45-80 seconds.

FIG. 22 illustrates a flowchart of an exemplary method 2200 for controlling an automatic toilet seat assembly of a toilet and reducing an amount of toilet plume entering air outside of the toilet, according to some embodiments. According to some embodiments, a controller of method 2200 may be configured to initiate flushing only when the lid is in the closed lid position. According to some embodiments, the method 2200 can be implemented for example in seat assemblies 200, 300, 400, 500, 600*a*, and 600*b*. According to some embodiments, the method 2200 can be implemented for seat assemblies shown in FIGS. 14A-14B, 15A-15B, 16A-16B, and 17A-17D.

At step 2210, a first presence of a user may be detected. At step 2220, a toilet lid of the toilet seat assembly may be moved to an open lid position with respect to a toilet bowl and a toilet seat after detecting the first presence of the user. At step 2230, a first action of the user may be detected and it may be determined whether to move the toilet seat from a closed seat position to an open seat position with respect to the toilet bowl. According to some embodiments, the first action of the user may include, for example, moving towards the seat assembly, standing in close proximity to the seat assembly, hand gesturing over the seat assembly. According to some embodiments, the first action may include movement associated with use of the toilet seat in the closed seat position or the user indicating that the user will not use the toilet seat in the closed seat position. At step 2240, in accordance with determination of whether to move the toilet seat, the toilet seat may be moved to the open seat position or maintaining the toilet seat in the closed seat position. At step 2250, a second action of the user may be detected. According to some embodiments, the second action of the user may include, for example, moving away from the seat assembly, moving from a sitting position to a standing position, and hand gesturing over the seat assembly. At step 2260, the toilet lid may be moved to a closed lid position with respect to the toilet bowl after detecting the second action of the user. At step 2260, the toilet lid may be detected in the closed lid position. At step 2270, the toilet when the toilet lid is in the closed lid position may be automatically flushed, wherein the amount of toilet plume entering air outside of the toilet during the automatic flushing is reduced compared a toilet with a conventional lid in the closed position.

FIG. 23 illustrates a flowchart of an exemplary method 2300 for controlling an automatic toilet seat assembly of a toilet and reducing an amount of toilet plume entering air outside of the toilet, according to some embodiments. According to some embodiments, the method 2300 may be configured to disinfect at least a seat of the toilet seat assembly. According to some embodiments, a controller of method 2300 may be configured to initiate flushing and disinfection only when the lid is in the closed lid position. According to some embodiments, the method 2300 can be implemented for seat assemblies shown in FIGS. 14A-14B, 15A-15B, 16A-16B, and 17A-17D. According to some embodiments locations of one or more sensors for detecting in method 2300 may be located in one or more positions as shown in FIGS. 6A and 6B.

At step 2310, a first presence of a user may be detected. At step 2320, a toilet lid of the toilet seat assembly may be moved to an open lid position with respect to a toilet bowl and a toilet seat after detecting the first presence of the user. At step 2330, a first action of the user may be detected and it may be determined whether to move the toilet seat from a closed seat position to an open seat position with respect to the toilet bowl. According to some embodiments, the first action of the user may include, for example, moving towards the seat assembly, standing in close proximity to the seat assembly, hand gesturing over the seat assembly. According to some embodiments, the first action may include movement associated with use of the toilet seat in the closed seat position or the user indicating that the user will not use the toilet seat in the closed seat position. At step 2340, in accordance with determination of whether to move the toilet seat, the toilet seat may be moved to the open seat position or maintaining the toilet seat in the closed seat position. At step 2350, a second action of the user may be detected. According to some embodiments, the second action of the user may include, for example, moving away from the seat assembly, moving from a sitting position to a standing position, and hand gesturing over the seat assembly. At step

2360, the toilet lid may be moved to a closed lid position with respect to the toilet bowl after detecting the second action of the user. At step 2360, the toilet lid may be detected in the closed lid position. At step 2370, the toilet when the toilet lid is in the closed lid position may be automatically flushed, wherein the amount of toilet plume entering air outside of the toilet during the automatic flushing is reduced compared a toilet with a conventional lid in the closed position. At step 2380, the toilet seat may be disinfected by turning on a plurality of UV-C lamps when the toilet lid is in the closed lid position, wherein the UV-C lamps are mounted in the toilet lid.

Figure 24:
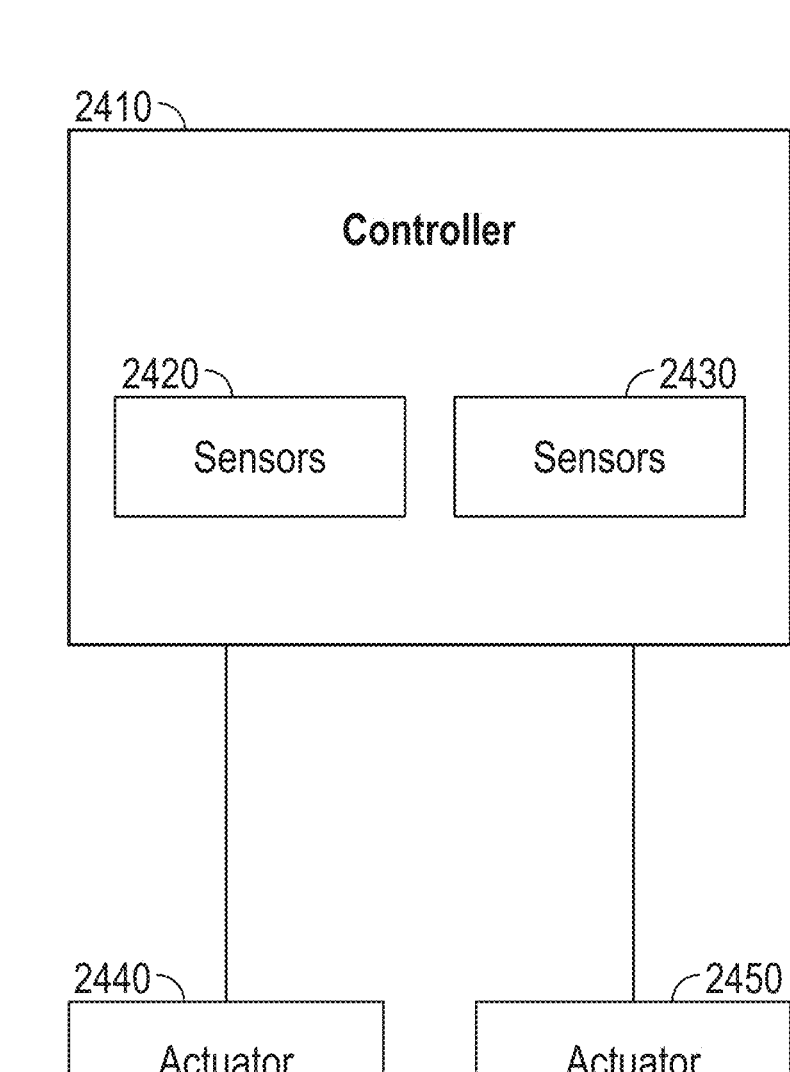
FIG. 24 shows an exemplary control system that can control one or more of automatic actions of a seat assembly and toilet, according to some embodiments.

FIG. 24 shows an exemplary control system 2400 that can control one or more of automatic actions of a seat assembly and toilet, according to some embodiments. For example, the control system 2400 may be configured to automatically close and open a lid, automatically close and open a seat, automatically flush a toilet when the lid is detected to be in a closed lid position, automatically disinfect one or more of the seat and the bowl when the lid is detected to be in a closed lid position, and automatically stop disinfecting before the lid is to an open lid position. According to some embodiments, the control system 2400 may include a controller 2410 that includes one or more sensors 2420, 2430 and one or more actuators 2440, 2450. The one or more actuators 2440, 2450 may be configured to automatically move one or more of the lid and the seat. According to some embodiments, the one or more actuators 2440, 2450 may be configured to actuate automatic flushing of the toilet when a lid is in a closed lid position or has moved from an open lid position to a closed lid position. According to some embodiments, the one or more actuators 2440, 2450 may be configured to actuate automatic flushing of the toilet. According to some embodiments, the one or more actuators 2440, 2450 may be configured to turn on a plurality of UV-C lamps (such as 1450, 1620, 1750, 1751, 1752) to disinfect one or more of the toilet seat, toilet bowl, and part of the toilet lid. According to some embodiments, the one or more actuator 2440, 2450 may be configured to disinfect at least an upper seat surface of a seat. According to some embodiments, the one or more sensors may be, for example, one or more sensors 650*a*, 650*b*. According to some embodiments, the controller 2410 may be configured to determine an action of a user based on detection from the one or more sensors 2420, 2430. According to some embodiments, the methods 2100-2300 can be implemented by the control system 2400. Methods 2100-2300 may be repeated for multiple uses of the toilet. The methods 1800-2000 may be repeated for subsequent users of the toilet. According to some embodiments, the control system 2400 may be mounted on a seat assembly such as 200, 300, 400, 500, 600*a*, and 600*b* described herein. According to some embodiments, the control system 2400 may be mounted on a seat assembly such as seat assemblies shown in FIGS. 14A-14B, 15A-15B, 16A-16B, and 17A-17D.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

Embodiments

Embodiment 1. A toilet seat assembly comprising:

a toilet seat comprising an inner rim around a central opening of the toilet seat and a contoured upper seat surface that extends between the inner rim and an outer rim of the toilet seat; and a lid hinged to the toilet seat and movable between an open lid position and a closed lid position with respect to a toilet bowl and the toilet seat;

wherein the lid comprises an inner liner that comprises a shaped surface portion and a core portion, the shaped surface portion is shaped to correspond to the contoured upper seat surface of the toilet seat, and the core portion is joined to the shaped surface portion, and in the closed lid position the shaped surface portion of the lid covers the upper seat surface of the toilet seat, and the core portion of the lid covers the central opening of the toilet seat;

a plurality of UV-C lamps positioned in one or more recessed portions of the shaped surface portion of the inner liner of the lid and configured to direct UV-C light towards the seat surface when the lid is in the closed lid position.

Embodiment 2. The seat assembly of embodiment 1, wherein the lid is hollow between an outer liner and the inner liner, and the outer liner covers the shaped surface portion and the core portion of the inner liner forming a hollow portion of the lid.

Embodiment 3. The seat assembly of embodiment 1 or 2, wherein the lid comprises one or more support liners mounted between the outer liner and the inner liner on an internal surface of the inner liner, and walls of the one or more recessed portions are formed by the one or more support liners, and the plurality of UV-C lamps are mounted to the one or more support liners in the one or more recessed portions.

Embodiment 4. The seat assembly of any of embodiments 1-3, wherein the one or more recessed portions of the shaped portion of the inner liner extends into the hollow portion of the lid towards the outer liner, and the inner liner comprises a UV-C light transparent layer configured to cover the one or more recessed portions and enclose the one or more support liners in the hollow portion of the lid.

Embodiment 5. The seat assembly of any of embodiments 1-4, wherein the UV-C transparent layer is spaced from about 0.05 to about 0.5 inches away from the seat surface.

Embodiment 6. The seat assembly of any of embodiments 1-4, wherein the UV-C light transparent layer comprising a plurality of lenses.

Embodiment 7. The seat assembly of embodiment 6, wherein each lens of the plurality of lenses comprises diamond shaped cuts.

Embodiment 8. The seat assembly of any of embodiments 3-7, wherein the one or more support liners comprises one or more reflective pockets between the plurality of UV-C lamps.

Embodiment 9. The seat assembly of any of embodiments 1-8, wherein the lid comprises an edge portion configured for covering a sidewall of the toilet seat, covering a front opening in the toilet seat, and blocking at least a portion of light from the plurality of UV-C lamps when the lid is in the closed lid position.

Embodiment 10. The seat assembly of any of embodiments 1-9, wherein when the lid is in the closed lid position, the edge portion of the inner liner directs at least a portion of toilet plume leaving the toilet bowl and entering air outside of the toilet bowl in a downward direction.

Embodiment 11. The seat assembly of any of embodiments 1-10, wherein the plurality of UV-C lamps are integrated circuit chips.

Embodiment 12. The seat assembly of any of embodiments 1-11, wherein the plurality of UV-C lamps are integrated circuit chips connected via a harness of printed film circuit.

Embodiment 13. The seat assembly of any of embodiments 1-12, wherein the plurality of UV-C lamps are integrated circuit chips, and a first set of the plurality of UV-C lamps include a first circuit board that contacts the shaped surface portion of the inner liner and a second set of the plurality of UV-C lamps include a second circuit board that contacts the shaped surface portion of the inner liner.

Embodiment 14. The seat assembly of any of embodiments 1-13, wherein the plurality of UV-C lamps comprises a set of UV-C lamps configured to provide an illumination cone from about 90 degrees to about 150 degrees directed towards the upper seat surface.

Embodiment 15. The seat assembly of any of embodiments 1-14, wherein the lid is a two-component lid comprising an outer liner and the inner liner, the outer liner is joined to the inner liner.

Embodiment 16. The seat assembly of embodiment 15, wherein the lid comprises a hollow portion between the outer liner and the inner liner.

Embodiment 17. The seat assembly of any of embodiments 1-16, wherein the upper seat surface is inclined downward from the outer rim of the toilet seat to the inner rim of the toilet seat towards the central opening.

Embodiment 18. The seat assembly of any of embodiments 1-17, wherein a lid-to-seat clearance between the shaped surface portion of the lid and the upper seat surface of the toilet seat is on average from about 0.05 to about 0.5 inches when the lid is in the closed lid position.

Embodiment 19. The seat assembly of any of embodiments 1-18, wherein a seat-to-bowl clearance between a bottom surface of the toilet seat and an upper rim of the toilet bowl is on average from about 0.05 to about 0.5 inches when the lid is in the closed lid position and the toilet seat is in the closed seat position.

Embodiment 20. The seat assembly of any of embodiments 1-19, wherein the lid in the closed position is configured to allow a reduced mass of air that enters the toilet during a flush by from about 20% to about 80% compared to a conventional mass of air that enters a conventional toilet during a flush when a conventional lid of the conventional toilet is in an open position, wherein the conventional toilet is configured to flush from 0.8 gallons to 1.6 gallons per flush.

Embodiment 21. The seat assembly of embodiment 20, wherein the reduced mass of air is from about 3 grams to about 18 grams of air.

Embodiment 22. The seat assembly of embodiment 20, wherein the reduced mass of air is configured to reduce an amount of toilet plume that leaves the toilet bowl and enters air outside of the toilet bowl after flushing.

Embodiment 23. The seat assembly of any of embodiments 1-22, wherein the inner rim of the seat extends completely around the central opening of the seat.

Embodiment 24. The seat assembly of any of embodiments 1-23, wherein a cleaning cycle of the toilet seat assembly occurs when light from the plurality of UV-C lamps is directed towards the seat surface, and the cleaning cycle is automatically initiated when the toilet lid assumes the closed lid position.

Embodiment 25. The toilet seat assembly of any of embodiments 1-24, wherein a cleaning cycle of the toilet seat assembly occurs when light from the plurality of UV-C lamps is directed towards the seat surface, and the cleaning cycle is manually initiated by a user.

Embodiment 26. A toilet seat system comprising:

the toilet seat assembly of embodiment 1;

a first control system comprising one or more first sensors configured to detect a user and a position of the lid; and a controller configured to determine an action of the user, automatically move the lid between the open lid position and the closed lid position based on the action of the user determined by the controller, automatically flush the toilet when the lid is in detected to be in the closed lid position; and automatically disinfect the toilet seat by turning on a plurality of UV-C lamps when the lid is in the closed lid position;

wherein an amount of toilet plume entering air outside of the toilet bowl during the automatic flushing is reduced compared a toilet with a conventional lid in the closed position.

Embodiment 27. The toilet seat system of embodiment 24, wherein the controller is configured to automatically flush the toilet only when the lid is in the closed lid position.

Embodiment 28. The toilet seat system of embodiment 24, wherein the lid comprises an outer liner configured to cover the shaped surface portion and the core portion of the inner liner, and the one or more sensors are positioned on one or more of the outer liner and the inner liner.

Embodiment 29. The toilet seat system of any of embodiments 26-28, wherein the controller is configured to disinfect the toilet seat by turning on a plurality of UV-C lamps upon receiving a manual input by a user.

Embodiment 30. A method of controlling the toilet seat assembly of embodiment 24 and reducing an amount of toilet plume entering air outside of a toilet, the method comprising:

detecting a first presence of a user;

moving a toilet lid of the toilet seat assembly from a closed lid position to an open lid position with respect to a toilet bowl after detecting the first presence of the user;

detecting a first action of the user and determining whether to move the toilet seat from a closed seat position to an open seat position with respect to the toilet bowl;

in accordance with determination of whether to move the toilet seat, moving the toilet seat to the open seat position or maintaining the toilet seat in the closed seat position;

detecting a second action of the user;

moving the toilet lid to a closed lid position with respect to the toilet bowl after detecting the second action of the user;

detecting that the toilet lid is in the closed lid position;

automatically flushing the toilet when the toilet lid is in the closed lid position, wherein the amount of toilet plume entering air outside of the toilet during the automatic flushing is reduced compared a toilet with a conventional lid in the closed position; and disinfecting the toilet seat by turning on a plurality of UV-C lamps when the toilet lid is in the closed lid position, wherein the UV-C lamps are mounted in the toilet lid.

Embodiment 31. The method of embodiment 30, wherein the toilet seat comprises an inner rim around a central opening of the toilet seat and a contoured upper seat surface that extends between the inner rim and an outer rim of the toilet seat and the toilet lid comprises an inner liner that comprises a shaped surface portion and a core portion, the shaped surface portion of the lid is shaped to correspond to the contoured upper seat surface of the toilet seat, wherein in the closed lid position the shaped surface portion of the lid covers the upper seat surface of the toilet seat, and the core portion of the lid covers the central opening of the toilet seat, and wherein the plurality of UV-C lamps are positioned in one or more recessed portions of the shaped surface portion of the inner liner of the lid and configured to direct UV-C light towards the seat surface when the lid is in the closed lid position.

Embodiment 32. The method of embodiment 30 or 31, wherein the lid comprises an outer liner and the lid is hollow between the outer liner and the inner liner, and wherein the outer liner covers the shaped surface portion and the core portion of the inner liner forming a hollow portion of the lid.

Embodiment 33. The method of embodiment 32, wherein the lid comprises one or more support liners mounted between the outer liner and the inner liner on an internal surface of the inner liner, and the walls of the one or more recessed portions are formed by the one or more support liners, and the plurality of UV-C lamps are mounted to the one or more support liners in the one or more recessed portions.

Embodiment 34. The method of embodiment 33, wherein the one or more recessed portions of the shaped portion of the inner liner extends into the hollow portion of the lid towards the outer liner, and the inner liner comprises a UV-C light transparent layer configured to cover the one or more recessed portions and enclose the one or more support liners in the hollow portion of the lid.

Embodiment 35. The method of embodiment 34, wherein the UV-C transparent layer is spaced from about 0.05 to about 0.5 inches away from the seat surface.

Embodiment 36. The method of embodiment 34, wherein the UV-C light transparent layer comprising a plurality of lenses.

Embodiment 37. The method of embodiment 36, wherein each lens of the plurality of lenses comprises diamond shaped cuts.

Embodiment 38. The method of any of embodiments 33-37, wherein the one or more support liners comprises one or more reflective pockets between the plurality of UV-C lamps.

Embodiment 39. The method of any of embodiments 30-38, wherein the lid comprises an edge portion configured for covering a sidewall of the toilet seat, covering a front opening in the toilet seat, and blocking at least a portion of light from the plurality of UV-C lamps when the lid is in the closed lid position.

Embodiment 40. The method of embodiment 39, wherein when the lid is in the closed lid position, the edge portion of the inner liner directs at least a portion of toilet plume leaving the toilet bowl and entering air outside of the toilet bowl in a downward direction.

Embodiment 41. The method of any of embodiments 30-40, wherein the plurality of UV-C lamps are integrated circuit chips, and a first set of the plurality of UV-C lamps include a first circuit board that contacts the shaped surface portion of the inner liner and a second set of the plurality of UV-C lamps include a second circuit board that contacts the shaped surface portion of the inner liner.

Embodiment 42. The method of any of embodiments 30-41, wherein the plurality of UV-C lamps comprises a set of UV-C lamps configured to provide an illumination cone from about 90 degrees to about 150 degrees directed towards the upper seat surface.

Embodiment 43. The method of any of embodiments 31-42, wherein the upper seat surface is inclined downward from the outer rim of the toilet seat to the inner rim of the toilet seat towards the central opening.

Embodiment 44. The method of any of embodiments 31-43, wherein a lid-to-seat clearance between the shaped surface portion of the lid and the upper seat surface of the toilet seat is on average from about 0.05 to about 0.5 inches when the lid is in the closed lid position.

Embodiment 45. The method of any of embodiments 31-44, wherein a seat-to-bowl clearance between a bottom surface of the toilet seat and an upper rim of the toilet bowl is on average from about 0.05 to about 0.5 inches when the lid is in the closed lid position and the toilet seat is in the closed seat position.

Embodiment 46. The method of any of embodiments 31-45, wherein the lid in the closed position is configured to allow a reduced mass of air that enters the toilet during a flush by from about 20% to about 80% compared to a conventional mass of air that enters a conventional toilet during a flush when a conventional lid of the conventional toilet is in an open position, wherein the conventional toilet is configured to flush from 0.8 gallons to 1.6 gallons per flush.

Embodiment 47. The method of embodiment 46, wherein the reduced mass of air is from about 3 grams to about 18 grams of air.

Embodiment 48. The method of embodiment 47, wherein the reduced mass of air is configured to reduce an amount of toilet plume that leaves the toilet bowl and enters air outside of the toilet bowl after flushing.

Embodiment 49. The method of any of embodiments 30-48, wherein the plurality of UV-C lamps are integrated circuit chips.

Embodiment 50. The method of any of embodiments 30-49, wherein the plurality of UV-C lamps are integrated circuit chips connected via a harness of printed film circuit.

Embodiment 51. The method of any of embodiments 30-50, comprising detecting a second presence of a user, and after detecting the second presence of the user, repeating moving the toilet lid, detecting the first action, moving the toilet to the open seat position or maintaining the toilet seat in the closed seat position, detecting the second action of the user, moving the toilet lid to the closed lid position, detecting the toilet lid in the closed lid position, automatically flushing the toilet, and disinfecting the toilet seat.

Embodiment 52. The method of embodiment 51, wherein the detecting the second presence of the user during disinfection of the toilet seat is configured to stop disinfection of the toilet seat prior to moving the toilet lid from the closed lid position to the open lid position.

Embodiment 53. The method of any of embodiments 30-52, wherein the second action of the user includes the user moving away from the toilet.

Embodiment 54. A toilet lid configured to cover a contoured upper seat surface of a toilet seat and a central opening of the toilet seat, the contoured upper seat surface extends between an inner rim and an outer rim of the toilet seat, the lid comprising:

an inner liner that comprises a shaped surface portion and a core portion, the shaped surface portion is shaped to correspond to the contoured upper seat surface of the toilet seat, and the core portion is joined to the shaped surface portion; and a plurality of UV-C lamps positioned in one or more recessed portions of the shaped surface portion of the inner liner of the lid and configured to direct UV-C light towards the seat surface when the lid is in the closed lid position;

wherein in the closed lid position the shaped surface portion of the lid covers the upper seat surface of the toilet seat, and the core portion of the lid covers the central opening of the toilet seat; and wherein the lid is hinged to the toilet seat and movable between an open lid position and a closed lid position with respect to a toilet bowl and the toilet seat.

Embodiment 55. The lid of embodiment 54, wherein the lid is hollow between an outer liner and the inner liner, and the outer liner covers the shaped surface portion and the core portion of the inner liner forming a hollow portion of the lid.

Embodiment 56. The lid of embodiment 55, wherein the lid comprises one or more support liners mounted between the outer liner and the inner liner on an internal surface of the inner liner, and walls of the one or more recessed portions are formed by the one or more support liners, and the plurality of UV-C lamps are mounted to the one or more support liners in the one or more recessed portions.

Embodiment 57. The lid of embodiment 56, wherein the one or more recessed portions of the shaped portion of the inner liner extends into the hollow portion of the lid towards the outer liner, and the inner liner comprises a UV-C light transparent layer configured to cover the one or more recessed portions and enclose the one or more support liners in the hollow portion of the lid.

Embodiment 58. The lid of embodiment 57, wherein the UV-C transparent layer is spaced from about 0.05 to about 0.5 inches away from the seat surface.

Embodiment 59. The lid of embodiment 57, wherein the UV-C light transparent layer comprising a plurality of lenses.

Embodiment 60. The lid of embodiment 59, wherein each lens of the plurality of lenses comprises diamond shaped cuts.

Embodiment 61. The lid of embodiment 56, wherein the one or more support liners comprises one or more reflective pockets between the plurality of UV-C lamps.

Embodiment 62. The lid of any of embodiments 54-61, wherein the lid comprises an edge portion configured for covering a sidewall of the toilet seat, covering a front opening in the toilet seat, and blocking at least a portion of light from the plurality of UV-C lamps when the lid is in the closed lid position.

Embodiment 63. The lid of embodiment 62, wherein when the lid is in the closed lid position, the edge portion of the inner liner directs at least a portion of toilet plume leaving the toilet bowl and entering air outside of the toilet bowl in a downward direction.

Embodiment 64. The lid of any of embodiments 54-63, wherein the plurality of UV-C lamps are integrated circuit chips.

Embodiment 65. The lid of any of embodiments 54-64, wherein the plurality of UV-C lamps are integrated circuit chips connected via a harness of printed film circuit.

Embodiment 66. The lid of any of embodiments 54-65, wherein the plurality of UV-C lamps are integrated circuit chips, and a first set of the plurality of UV-C lamps include a first circuit board that contacts the shaped surface portion of the inner liner and a second set of the plurality of UV-C lamps include a second circuit board that contacts the shaped surface portion of the inner liner.

Embodiment 67. The lid of any of embodiments 54-66, wherein the plurality of UV-C lamps comprises a set of UV-C lamps configured to provide an illumination cone from about 90 degrees to about 150 degrees directed towards the upper seat surface.

Embodiment 68. The lid of any of embodiments 54-67, wherein the lid is a two-component lid comprising an outer liner and the inner liner, the outer liner is joined to the inner liner.

Embodiment 69. The lid of embodiment 68, wherein the lid comprises a hollow portion between the outer liner and the inner liner.

Embodiment 70. The lid of any of embodiments 54-69, wherein the upper seat surface is inclined downward from the outer rim of the toilet seat to the inner rim of the toilet seat towards the central opening.

Embodiment 71. The lid of any of embodiments 54-70, wherein a lid-to-seat clearance between the shaped surface portion of the lid and the upper seat surface of the toilet seat is on average from about 0.05 to about 0.5 inches when the lid is in the closed lid position.

Embodiment 72. The lid of any of embodiments 54-71, wherein a seat-to-bowl clearance between a bottom surface of the toilet seat and an upper rim of the toilet bowl is on average from about 0.05 to about 0.5 inches when the lid is in the closed lid position and the toilet seat is in the closed seat position.

Embodiment 73. The lid of any of embodiments 54-72, wherein the lid in the closed position is configured to allow a reduced mass of air that enters the toilet during a flush by from about 20% to about 80% compared to a conventional mass of air that enters a conventional toilet during a flush when a conventional lid of the conventional toilet is in an open position, wherein the conventional toilet is configured to flush from 0.8 gallons to 1.6 gallons per flush.

Embodiment 74. The lid of embodiment 73, wherein the reduced mass of air is from about 3 grams to about 18 grams of air.

Embodiment 75. The lid of embodiment 73, wherein the reduced mass of air is configured to reduce an amount of toilet plume that leaves the toilet bowl and enters air outside of the toilet bowl after flushing.

Embodiment 76. The lid of any of embodiments 54-75, wherein the inner rim of the seat extends completely around the central opening of the seat.

Embodiment 77. A toilet seat system comprising:
the lid of embodiment 51;
a first control system comprising one or more first sensors configured to detect a user and a position of the lid; and
a controller configured to determine an action of the user, automatically move the lid between the open lid position and the closed lid position based on the action of the user determined by the controller, automatically flush the toilet when the lid is in detected to be in the closed lid position; and automatically disinfect the toilet seat by turning on a plurality of UV-C lamps when the lid is in the closed lid position;

wherein an amount of toilet plume entering air outside of the toilet bowl during the automatic flushing is reduced compared a toilet with a conventional lid in the closed position.

Embodiment 78. The toilet seat system of embodiment 77, wherein the controller is configured to automatically flush the toilet only when the lid is in the closed lid position.

Embodiment 79. The toilet seat system of embodiment 77 or 75, wherein the lid comprises an outer liner configured to cover the shaped surface portion and the core portion of the inner liner, and the one or more sensors are positioned on one or more of the outer liner and the inner liner.

Embodiment 80. The toilet seat system of any of embodiments 77-79, wherein the controller is configured to disinfect the toilet seat by turning on the plurality of UV-C lamps upon receiving a manual input by a user.

Embodiment 81. A toilet seat assembly comprising:
a toilet seat comprising an inner rim around a central opening of the toilet seat and a contoured upper seat surface that extends between the inner rim and an outer rim of the toilet seat;
a lid hinged to the toilet seat and movable between an open lid position and a closed lid position with respect to a toilet bowl and the toilet seat; and
a dynamic UV-C light mechanism comprising:
a track complementary in shape to the upper seat surface of the toilet seat and positioned on an underside of the lid, such that the track faces the upper seat surface of the toilet seat when the lid is in the closed lid position;
one or more UV-C lamps configured to travel around a perimeter of the track and configured to direct light towards the seat surface when the lid is in a closed lid position.

Embodiment 82. The toilet seat assembly of embodiment 81, wherein the dynamic UV-C light mechanism comprises one or more arms, each arm of the one or more arms configured to pivot at a proximal end from a central location within the track, wherein each arm extends from its proximal end at the central location to a distal end, the distal end in contact with the track and configured to move 360 degrees around the track.

Embodiment 83. The toilet seat assembly of embodiment 82, wherein the one or more UV-C lamps are located at the distal end of each of the one or more arms.

Embodiment 84. The toilet seat assembly of embodiment 82 or 83, wherein the one or more arms is configured to couple to the track using a pin.

Embodiment 85. The toilet seat assembly of embodiment 82 or 83, wherein the one or more arms is configured to couple to the track using a roller bearing mechanism.

Embodiment 86. The toilet seat assembly of embodiment 82 or 83, wherein the one or more arms comprises a wheel at the distal end of each arm that is configured to roll along an interior surface of the track.

Embodiment 87. The toilet seat assembly of any of embodiments 82-86, wherein the one or more arms is telescoping.

Embodiment 88. The toilet seat assembly of any of embodiments 82-87, wherein the one or more arms is spring-loaded.

Embodiment 89. The toilet seat assembly of any of embodiments 81-88, wherein a cleaning cycle of the dynamic UV-C light mechanism is automatically initiated when the toilet lid assumes its closed lid position.

Embodiment 90. The toilet seat assembly of any of embodiments 81-89, wherein a cleaning cycle of the dynamic UV-C light mechanism is manually initiated by a user.

Embodiment 91. The toilet seat assembly of any of embodiments 81-90, wherein the dynamic UV-C light mechanism comprises a motor configured to cause the one or more UV-C lamps to rotate around the track.

Embodiment 92. The toilet seat assembly of any of embodiments 81-91, wherein the one or more UV-C lamps are integrated circuit chips.

Embodiment 93. The toilet seat assembly of any of embodiments 81-92, wherein the one or more UV-C lamps are integrated circuit chips connected via a harness of printed film circuit.

The invention claimed is:

1. A toilet seat assembly comprising:
a toilet seat comprising an inner rim around a central opening of the toilet seat and a contoured upper seat surface that extends between the inner rim and an outer rim of the toilet seat; and
a lid hinged to the toilet seat and movable between an open lid position and a closed lid position with respect to a toilet bowl and the toilet seat;
wherein the lid comprises an inner liner that comprises a shaped surface portion and a core portion, the shaped surface portion is shaped to correspond to the contoured upper seat surface of the toilet seat, and the core portion is joined to the shaped surface portion, and in the closed lid position the shaped surface portion of the lid covers the upper seat surface of the toilet seat, and the core portion of the lid covers the central opening of the toilet seat;
a plurality of UV-C lamps positioned in one or more recessed portions of the shaped surface portion of the inner liner of the lid and configured to direct UV-C light towards the seat surface when the lid is in the closed lid position;
wherein the lid comprises an outer edge portion extending at least to a bottom surface of the toilet seat and configured for covering a sidewall of the toilet seat, covering a front opening in the toilet seat, and blocking at least a portion of light from the plurality of UV-C lamps when the lid is in the closed lid position;
wherein a UV-C transparent layer of the inner liner is spaced from about 0.05 to about 0.5 inches away from the seat surface when the lid is in a closed position.

2. The seat assembly of claim 1, wherein the lid is hollow between an outer liner and the inner liner, and the outer liner covers the shaped surface portion and the core portion of the inner liner forming a hollow portion of the lid.

3. The seat assembly of claim 1, wherein the lid comprises one or more support liners mounted between the outer liner and the inner liner on an internal surface of the inner liner, and walls of the one or more recessed portions are formed by the one or more support liners, and the plurality of UV-C lamps are mounted to the one or more support liners in the one or more recessed portions.

4. The seat assembly of claim 1, wherein the one or more recessed portions of the shaped portion of the inner liner extends into the hollow portion of the lid towards the outer liner, and the inner liner comprises the UV-C light transparent layer configured to cover the one or more recessed portions and enclose the one or more support liners in the hollow portion of the lid.

5. The seat assembly of claim 1, wherein the UV-C transparent layer comprises a plurality of lenses.

6. The seat assembly of claim 5, wherein each lens of the plurality of lenses comprises diamond shaped cuts.

7. The seat assembly of claim 3, wherein the one or more support liners comprises one or more reflective pockets between the plurality of UV-C lamps.

8. The seat assembly of claim 1, wherein when the lid is in the closed lid position, the edge portion directs at least a portion of toilet plume leaving the toilet bowl and entering air outside of the toilet bowl in a downward direction.

9. The seat assembly of claim 1, wherein the plurality of UV-C lamps are integrated circuit chips.

10. The seat assembly of claim 1, wherein the plurality of UV-C lamps are integrated circuit chips connected via a harness of printed film circuit.

11. The seat assembly of claim 1, wherein the plurality of UV-C lamps are integrated circuit chips, and a first set of the plurality of UV-C lamps include a first circuit board that contacts the shaped surface portion of the inner liner and a second set of the plurality of UV-C lamps include a second circuit board that contacts the shaped surface portion of the inner liner.

12. The seat assembly of claim 1, wherein the plurality of UV-C lamps comprises a set of UV-C lamps configured to provide an illumination cone from about 90 degrees to about 150 degrees directed towards the upper seat surface.

13. The seat assembly of claim 1, wherein the lid is a two-component lid comprising an outer liner and the inner liner, the outer liner is joined to the inner liner.

14. The seat assembly of claim 13, wherein the lid comprises a hollow portion between the outer liner and the inner liner.

15. The seat assembly of claim 1, wherein the upper seat surface is inclined downward from the outer rim of the toilet seat to the inner rim of the toilet seat towards the central opening.

16. The seat assembly of claim 1, wherein a lid-to-seat clearance between the shaped surface portion of the lid and the upper seat surface of the toilet seat is on average from about 0.05 to about 0.5 inches when the lid is in the closed lid position.

17. The seat assembly of claim 1, wherein a cleaning cycle of the toilet seat assembly occurs when light from the plurality of UV-C lamps is directed towards the seat surface, and the cleaning cycle is automatically initiated when the toilet lid assumes the closed lid position.

18. The toilet seat assembly of claim 1, wherein a cleaning cycle of the toilet seat assembly occurs when light from the plurality of UV-C lamps is directed towards the seat surface, and the cleaning cycle is manually initiated by a user.

* * * * *